United States Patent [19]

Gillespie

[11] Patent Number: 5,482,834
[45] Date of Patent: Jan. 9, 1996

[54] EVALUATION OF NUCLEIC ACIDS IN A BIOLOGICAL SAMPLE HYBRIDIZATION IN A SOLUTION OF CHAOTROPHIC SALT SOLUBILIZED CELLS

[75] Inventor: David H. Gillespie, Glenmore, Pa.

[73] Assignee: Hahnemann University, Philadelphia, Pa.

[21] Appl. No.: 6,190

[22] Filed: Jan. 19, 1993

Related U.S. Application Data

[63] Continuation of Ser. No. 299,150, Dec. 30, 1988, abandoned, which is a continuation-in-part of Ser. No. 859,003, May 2, 1986, abandoned, which is a continuation-in-part of Ser. No. 594,308, Mar. 28, 1984, abandoned, which is a continuation-in-part of Ser. No. 378,711, May 17, 1982, Pat. No. 4,483,920.

[51] Int. Cl.$^6$ .............................. C12Q 1/68; C12N 11/00; C12N 15/00; C07H 21/00

[52] U.S. Cl. ............................... 435/6; 435/174; 435/179; 435/810; 435/820; 536/24.3; 935/78

[58] Field of Search .................................. 435/6, 41, 174, 435/179, 810, 820; 935/78; 534/24.3

[56] References Cited

U.S. PATENT DOCUMENTS

| | | | |
|---|---|---|---|
| 4,483,920 | 11/1984 | Gillespie et al. | 435/91 X |
| 4,851,330 | 7/1989 | Kohne | 435/31 X |
| 5,225,326 | 7/1993 | Bresser et al. | 935/78 X |
| 5,298,417 | 3/1994 | Cancedda et al. | 435/240.1 |

FOREIGN PATENT DOCUMENTS

| | | |
|---|---|---|
| 586790A1 | 3/1994 | European Pat. Off. . |
| 60-162875 | 7/1985 | Japan . |
| 2139349 | 11/1984 | United Kingdom . |

OTHER PUBLICATIONS

Thompson, et al., Analytical Biochemistry, vol. 163, 1987, pp. 281–291.
Cox et al., FEBS Letters, 155:73–80 (1980).
Gillespie et al., J. Mol. Biol. 12:829–842 (1965).
Bresser et al., Analytical Biochem. 129:357–364 (1983).
Lillie et al., *The Journal of Investigative Dermatology*, "Growth of Stratified Squamous Epithelium on Reconstituted Extracellular Matrices: Long–Term Culture", 2:100–109 (1988).

*Primary Examiner*—David M. Naff
*Attorney, Agent, or Firm*—Seidel, Gonda, Lavorgna & Monaco

[57] ABSTRACT

Nucleic acid components in a biological sample are detected and/or quantified utilizing a process wherein the sample is first solubilized with a chaotropic salt solution. In a preferred embodiment, cells and nucleic acid components therein are solubilized in the chaotropic salt solution and the solution is incubated with a labelled nucleic acid probe at 20° to 40° C. in the absence of formamide to cause molecular hybridization between the probe and solubilized nucleic acid components, and the molecular hybridization is detected. The chaotropic salt is selected from quanidine thiocyanate, alkali metal perchlorates, alkali metal iodides, alkali metal trifluoroacetates, alkali metal trichloroacetates and alkali metal thiocyanates. The probe may be in solution or immobilized. RNA detected or quantitated may be ribosomal RNA or genomic RNA, and in one embodiment the RNA is HIV viral RNA. When detecting DNA, the solution containing solubilized cells and DNA is heated to at least 45° C. to denature the DNA before hybridization.

16 Claims, 19 Drawing Sheets

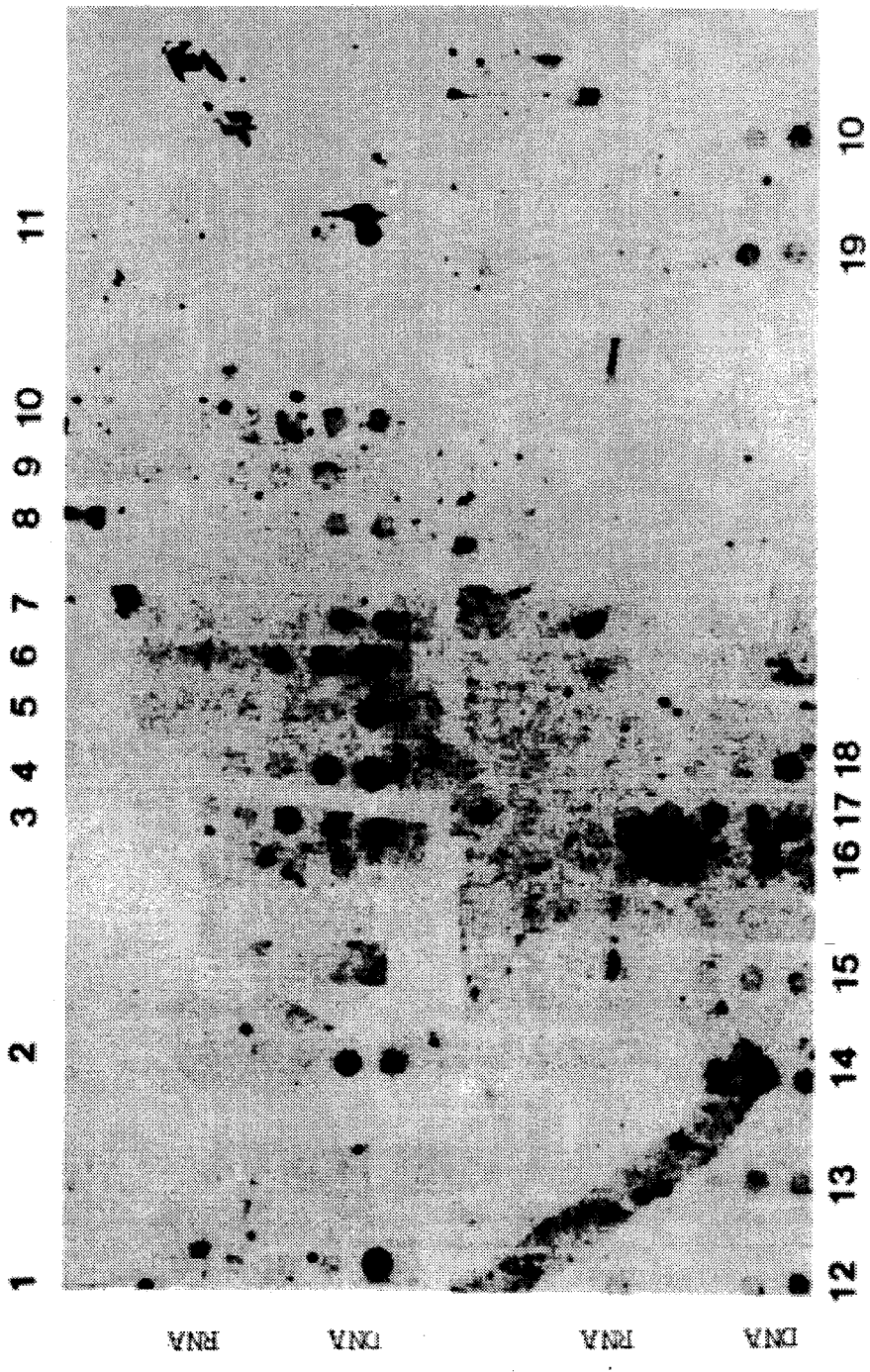

COMPETITIVE REVERSE PROBING

AIDS

EVALUATION OF NUCLEIC ACIDS IN A BIOLOGICAL SAMPLE HYBRIDIZATION IN A SOLUTION OF CHAOTROPHIC SALT SOLUBILIZED CELLS

This application is continuation of application Ser. No. 07/299,150, filed Dec. 30, 1988, now abandoned, which is a continuation-in-part of application Ser. No. 06/859,003, filed May 2, 1986, now abandoned, which is a continuation-in-part of application Ser. No. 06/594,308, filed Mar. 28, 1984, now abandoned, which is a continuation-in-part of application Ser. No. 06/378,711, filed May 17, 1982, now U.S. Pat. No. 4,483,920.

FIELD OF THE INVENTION

This invention relates to the fields of analytical chemistry and medicine, and in particular relates to a novel method for evaluating nucleic acids in a biological sample wherein said nucleic acids are made available for evaluation by chaotropic solubilization. The nucleic acids are evaluated by means of molecular hybridization with a complementary nucleic acid probe, in the chaotropic solution.

1. General Considerations

Tissues of patients are customarily examined for "markers" which may indicate a disease state. Marker evaluation can be an important part of a patient's initial diagnosis as well as provide a continued measurement of a patient's response to treatment and future prognosis. Conventional tissue markers include cell morphology and metabolism, the presence of certain enzymic activities or proteins or other molecules of biological import, the accumulation or disappearance of such molecules, etc. Recently, gene structure has provided a marker for certain diseases (Geever et: al., PNAS 78:5081–5085, 1981; Orkin et al, N. Eng. J. Med. 299:166–1721 1981, Chang and Kan, PNAS 76:2886–2889, 1979; Philips et al., PNAS 77:2853–2856, 1980).

Until this invention, however, it has been relatively difficult to easily and economically measure primary gene activation, i.e., the accumulation of specific message RNA molecules (RNA transcription). Existing procedures generally employ an appropriate "probe," usually a radiolabelled DNA molecule of known nucleotide sequence, to measure a quantity of specific (complimentary) message RNA sequence by a process called "molecular hybridization" (Gillespie, D., Methods Enzymology 12 B:641–668, 1968). Such procedures usually require first purifying message RNA from cells or tissues, a costly and laborious process. Then, molecular hybridization of the purified RNA to the probe is effected, and can be aided by immobilizing the RNA on a solid surface (Gilham, P. T., Biochemstry 7:2809–2813, 1968; Ponian, M. S., et al., Biochemistry 10:424–427, 1971; Wagner, A. F. et al., BBRC 45:184–189, 1971; Sheldon, R. et al., PNAS 69:417–421, 1972; Saxinger, W. C. et al., PNAS 69:2975–2978, 1972; Noyes, B. E. and Stark, G. R., Cell 5:301–310, 1975; Alwine, J. C. et al., PNAS 74:5350–5354, 1977; Thomas P. S., PNAS 77:5201–5205). In any case, RNA purification apart from immobilization is required by these procedures.

Alternatively, cells can be deposited on microscope slides or a like surface and molecular hybridization can be performed upon the message RNA in the cells, a technique called "in situ molecular hybridization" (Pardue, M. L. and Gall, J. G., PNAS 64:600–604, 1969; Brahic, M. and Haase, A. T., PNAS 75:6125–6129, 1978; Angerer, L. M. and Angerer, R. C., Nuc. Ac. Res. 9:2819–2840, 1981). However, this process can be time-consuming and unreliable and is only useful when the assay can be performed upon single cells.

2. Description of the Background Materials

A. DNA Immobilization in NaCl.

Following is a brief overview of the history of attempts to immobilize DNA on solid supports.

Since 1977 our ability to manipulate DNA and our knowledge of its structure has advanced in enormous leaps. This has been made possible primarily because of the technology of DNA immobilization and, more recently, because of the ability to sequence DNA. Since the original work on the binding of purified, single-stranded DNA to nitrocellulose (NC) membrane by Nygaard and Hall (Biophys. Biochem. Res. Comm. 12:98–104, 1963) and by Gillespie and Spiegelman (J. Mol. Biol. 12:829–842, 1965), DNA-NC has been exploited in an array of imaginative and elegant ways.

One of the most imaginative extensions was devised by Grunstein and Hogness (Proc. Nat. Acad. Sci. USA 72:3961–3965, 1975) who discovered how to blot colonies of whole cells onto NC in such a way that only their DNA stuck to the membrane, providing a DNA image of the original colony of the membrane. This "colony lift" technique permitted the rapid screening of recombinant organism and advanced the present state of gene cloning by some 5–10 years. However, this method and others based on the same principle (e.g. Scotto et al, Hepatology 3:279–284, 1983) are not quantitative because the conditions used to cause DNA denaturation (NaOH) interfere with DNA immobilization.

One of the most elegant extensions of DNA immobilization was invented by Southern (J. Mol. Bio. 98:503–517, 1975). He deduced a means to transfer to NC DNA which had been purified and then fractionated according to size in agarose gels. He was able to produce a DNA image of the gel-fractionated DNA on NC, which could then be probed for selected sequences. The "Southern transfer" or "Southern blot" is probably the most important technique we have available today for comparative gene structure analysis, short of DNA sequencing.

B. RNA Immobilization in NaCl.

Following is a brief overview of the history of attempts to immobilize RNA on solid supports.

In early DNA immobilization work, Gillespie and Spiegelman (J. Mol. Biol., 12:829–842, 1965) categorically reported that RNA would not bind to NC. Some years later, DeLarco and Guroff (Biochem. Biophys. Res. Comm. 50:486–492, 1973) corrected this erroneous conclusion by immobilizing RNA to NC, using very concentrated NaCl solutions to do this. They thought. that only certain RNA molecules stuck to NC, specifically RNA molecules bearing a terminal tract of adenosine residues, the so-called "poly(A) tail." All RNA molecules with sufficiently long poly(A) (herein also referred to as "poly (A)-plus RNA") tails could bind to NC in concentrated NaCl. As far as we know, all of these polyadenylated RNA molecules were message RNA, capable of coding for proteins. RNA molecules lacking poly(A) (herein also referred to as "poly(A)-minus RNA") did not appear to interact with NC in concentrated NaCl. Most of this poly(A)-minus RNA is ribosomal RNA and transfer RNA, which are noncodogenic RNA species, although a few percent of the poly(A)-minus RNA is "tailless" message RNA. Therefore, the concentrated-NaCl method for binding purified RNA to NC was selective for message RNA but it did not include all message RNA species.

In the mid and late 1970s several supports for immobilizing mRNA were described (see Seed B. Genetic Engi-

*neering* 4:91–102, 1982 for review). These were papers of various kinds which displayed reactive groups to which pure RNA could be covalently attached. These papers were not selective for mRNA, or even for RNA, since DNA and proteins could also be attached to the reactive groups. However, these did have the advantage that all RNA molecules, not a select population, could be immobilized on them.

In 1979, Pat Thomas reported an important observation. She noted that denatured RNA of all kinds could be immobilized onto NC in concentrated NaCl solutions (*Proc. Nat. Acad. Sci. USA* 77:5201–5205, 1980). She exploited this observation by developing the RNA-analogue of the Southern transfer, a method quite naturally dubbed the "Northern Transfer." Pat Thomas' work introduced a new explanation for the DeLarco/Guroff results; namely, that the RNA which bound to NC in concentrated NaCl did not do so through its long poly(A) tail, but because it was naturally more denatured than RNA with short or not terminal poly(A).

Unfortunately, the Northern transfer methodology has not lent itself to the immobilization of mRNA from whole cells or other natural biological sources. White and Bancroft (*J. Biol. Chem.* 257:8659–8572, 1982) were able to develop a method for immobilizing total RNA from cytoplasmic extracts based on Pat Thomas' denaturation procedure but it has not become popular, probably because of the enormous problem presented by protein coimmobilization and the nagging question of how much denatured DNA would co-immobilize. A minor advance was made when it was learned that in NaCl, sodium dodecyl sulfate suppresses DNA-NC and protein-NC interactions but does not interfere with mRNA-NC interactions (Bresser et al., *DNA* 2:243–254, 1983), but the techniques based on selectively-through-detergents have also fallen short of reliable quantitation and all are restricted to the use of small amounts of cellular material.

All of the procedures described above depended on NaCl-promoted interactions between NC and DNA or RNA. In all these cases the nucleic acid had to be "fixed" to the NC by baking at high temperature. Consequently, RNA adsorbed to NC was biologically inactive—it could not be reverse transcribed or translated.

Gillespie et al., U.S. Pat. No. 4,483,920, issued on Nov. 20, 1984, describe a method for directly immobilizing an mRNA from cells onto filter paper wherein cellular mRNA is solubilized with a chaotropic salt, immobilized on a filter which selectively binds mRNA, with an optional baking step.

The thus immobilized target mRNA is then hybridized with a labeled DNA probe.

Cox et. al., *FEBS LETTERS*, Vol. 155, No. 1, 73–80 (May, 1983) describe a single-step procedure for the isolation of a particular mRNA from crude lysates of *Physarum polycephalum*, exposed by solubilization with, among others, quanidinium isothiocyanate by hybridization to complementary DNA which has been immobilized by binding to aminotriophenol paper. Thus not just the poly(A)-tails, but the coding region of the mRNA was isolated by molecular hybridization in the crude quanidinium isothiocyanate lysate.

Strayer et al., *PNAS*, Vol. 80, pp. 4770–4774 (August, 1983) disclose liquid-liquid molecular hybridization of chaotropically solubilized DNA where the hybridization is effected in the chaotropic solution. The duplex regions lowered the buoyancy of the DNA complex in direct proportion to the length ratio of the double-stranded to singles-stranded elements, thus permitting analysis of the DNA by means of a NaI gradient.

Kohne, International Application No. WO 84/02721, published Jul. 19, 1984, disclosed a method for quantitating and detecting RNA-containing organisms comprising solubilizing the nucleic acid of said organism and probing the solubilized nucleic acid with a labeled probe complementary to the nucleic acid, said hybridization effected in solution, without purifying the sample RNA. At page 34, Kohne suggests using a chaotropic agent as the solubilizing agent. Kohne utilizes an "in solution" hybridization, i.e., both the probe and the sample RNA were in solution.

Cox et al., European Patent Application Publication No. 0 127 327 A1, published on Dec. 5, 1984, disclose an assay for nucleic acids comprising chaotropically solubilizing cellular nucleic acid and performing a molecular hybridization in the chaotropic solution utilizing labeled probe complementary to the target nucleic acid. While all the examples disclosed by Cox et al. are directed to heterogeneous hybridization utilizing immobilized, labeled probe, at page 7, line 18, Cox et al. do suggest that the hybridization might be "homogenous." No homogeneous hybridization parameters are disclosed.

However, prior to the effective date of this invention, a need had continued to exist for a means for evaluating the nucleic acid of a biological sample that permitted molecular hybridization between a labeled nucleic acid probe complementary to the sample nucleic acid and the sample nucleic acid which did not require a prior purification and/or immobilization of the solubilized sample nucleic acid.

More importantly, a need had continued to exist for a method for evaluating cellular nucleic acids which is adapted for clinical use. Such a method must retain the accuracy and sensitivity of the technical procedure cited above when used in the research laboratory. However, clinical adaptation additionally demands speed, simplicity/reliability, economy, versatility and automatability.

Speed—An ideal clinical test should be carried out in 30 min., i.e., during an outpatient's visit to the doctor's office. Minimally, a gene diagnosis test should be more rapid than competing culture, immunological or biochemical tests. Practically, a 2–3 hour goal for completion of a gene diagnosis test has been set by most commercial houses.

Simplicity/Reliability—A clinical test should be able to be performed by a laboratory technician with a high school degree. The method should not be perturbed by ordinary fluctuations in temperature, time, volumes, sample composition, etc., expected in a clinical laboratory. The method should be simple enough to automate.

Economy—A gene diagnosis test adapted to the clinic must be as economical as the test it replaces in the clinical market, typically under ten dollars per test.

Versatility—A gene diagnosis method should be applicable to the wide range of "dirty" clinical samples including blood, urine, solid tissues, stools, swabs, etc., containing viruses, cells, microorganisms, etc.

Automatability—All or portions of gene diagnosis procedures will be done by machine in clinical laboratories. Such a procedure will have a minimum of steps and will be performed at near ambient temperatures without corrosive or toxic solvents or solutes. Such a procedure will avoid cumbersome methods such as centrifugation and gel electrophoresis.

Clinical adaptability demands that all of the above qualities be added to laboratory-grade accuracy and sensitivity. To our knowledge, the prior art does not anticipate how this is to be done.

C. Measurement of HIV Load in Patients

AIDS patients were found to have antibodies which cross-react with HTLV-I (Essex et al., *Science* 220:859

(1983)). Later, a new virus, HIV or HTLV III/LAV (AIDS virus) was discovered (Barre-Sinoussi et al., *Science* 220:868 (1983); Povovic et al., ibid .224:497 (1984)), and it was shown that AIDS patients have antibodies against various proteins of AIDS virus (Sarngadharan et al., *Science* 224:506 (1984); Kalyanaraman et al., *Science* 225:321 (1984)). AIDS patients carry AIDS virus DNA sequences in cells (Hahn et al., *Nature* 312:166 (1984); Shaw et al., *Science* 227:177 (1985)) and in brain cells (Shaw et al., *Science* 227:177 (1985)). Very few lymphocytes may contain AIDS virus (Hahn et al., *Nature* 312:166 (1984); Shaw et al., *Science* 226:1165 (1984); Shaw et al., *Science* 227:177 (1985)). The virus is cytopathic to T helper cells but may be carried by other blood cells without cell lysis (D. Morgan and J. Levy, personal communication).

Recent estimates suggest that 1 lymphocyte in $10^4$ or fewer may be infected. AIDS virus isolates from different individuals can exhibit genomic diversity (Wong-Staal et al., *Science* 229:759 (1985)). The AIDS virus is genetically related to lentivirus (Chiu et al., *Nature* 317:366 (1985)) and, like lentiviruses, is cytopathic, at least in T4 cells. Since lentiviruses can escape immune surveillance, Chiu et al. "emphasize the challenge that these rapidly evolving retroviruses present in prevention and control of their associated disease."

Many laboratories and commercial firms are attempting to measure HIV nucleic acids in AIDS patients. Cherman, Gallo, Volsky and others have prepared clones of HIV genes for use as probes. Measurements of HIV nucleic acids have been made following purification of RNA or DNA from cells infected with virus in vitro and from blood cells, but the techniques are neither rapid nor simple enough to use routinely on clinical samples. Detection of HIVRNA has been done by in situ hybridization following deposition of blood cells on microscope slides (Shaw et al., *Science* 227:177 (1985)). This approach is being exhibited by ENZO Biochemicals, ONCOR and DuPont in the form of commercially available kits or probes; however, it is clear that this approach will not offer the simplicity or reliability required of a clinically valuable HIV test. There is no convincing evidence that in situ hybridization can measure HIV quantitatively nor that a confirmatory test exists for cases of apparently positive detection. "Dot blots" have been used to measure virus RNA or DNA in infected cells, without nucleic acid purification. RNA can be selectively immobilized from lysed cells in NaI, GuSCN, formaldehyde/SDS or SDS; however, the efficiency of RNA immobilization is variable. Hybridization to immobilized nucleic acids RNA is relatively slow. A further defect of immobilization of nucleic acids from crude lysates is that the coimmobilization of proteins interferes with hybridization. All in all, these immobilization approaches, whether using lysates or purified nucleic acids, have lacked the sensitivity required of a clinically valuable HIV assay. Cetus has employed the strategy of target amplification, but presently this can only be performed with purified nucleic acids and presently requires a DNA target.

The current tests for detection of HIV virus is a coculture procedure. Mononuclear blood cells from AIDS patients are coculture with sensitive indicator cells, usually PHA stimulated lymphocytes from normal volunteer. After 1–3 weeks of coculture, virus released into the medium is assayed by measuring reverse transcriptase or viral antigen. The sensitivity of the present coculture tests is not known. Variation in the isolation frequency of successive cultures or certain patients has been observed. This variation might be related to the susceptibility of different donor preparations of human lymphocytes to infection with HIV (T. Folks et al., *J. Immunol.* 136:4049 (1985)). It is not yet possible to quantitate virus load with the coculture assay.

Work is in progress at Abbot and DuPont and elsewhere to develop a direct test for HIV antigens in serum of ARC/AIDS patients. Assays performed at Abbott on ARC/AIDS samples showed only 50% positivity by the direct assay. It can be anticipated, additionally, that direct antigen tests will be complicated by the simultaneous presence of small or amounts of antibodies in ARC/AIDS patients which form complexes with the antigen and are cleaved from the blood (J. Goudsmit et al., *The Lancet*, Sat 26 July, p. 177–180 (1986)).

SUMMARY OF THE INVENTION

The present invention provides a significant improvement in disease diagnosis. The invention is based on a method for immobilizing mRNA from a biological source which is simple, fast, and accurate. Broadly, the method relates to a process for immobilizing RNA, said process comprising the steps of:

A. dissolving a biological source containing RNA by contacting said biological source with a chaotropic salt solution; and B. filtering the thus dissolved biological source through a filter material which selectively immobilizes said mRNA.

The invention is quite advantageous relative to existing methodology which, as previously mentioned, requires a purification step and, separately, then requires a immobilization step. By the present invention a biological source containing RNA, such as cells, is first dissolved in a chaotropic salt solution which forms a solution of the mRNA and the rest of the cellular matter. By then filtering the solution of cellular material through a filter selectively immobilizes the mRNA, the rest of the cellular material is accordingly dispensed with by passing through the filter. Thus a great advantage of the invention is that the immobilization step is also inherently the purification step. No separation of the purification step from the immobilization step is required.

The fact that the immobilization step is also the purification step represents an important advance so far as simplifying and improving existing methods is concerned. Ordinarily biological samples must be purified extensively in order to remove co-immobilizing contaminants so that immobilization of a desired component can take place at all. In the present invention, however, the use of a chaotropic salt solution to dissolve biological samples results in the component of interest, RNA (or DNA as hereinafter explained) being selectively immobilized on an immobilizing filter material.

By "selectively immobilizing" RNA from a dissolved source of RNA such as cells or bacteria, it is meant that the majority of extraneous (i.e. non-RNA) material passes through the immobilization filter, although co-immobilization of some small fraction of non-RNA material is probably unavoidable. Simply passing the dissolved (i.e., in a chaotropic solution) source of RNA provides as much, if not more, purification than existing procedures employing separate purification steps. The essential steps, in the present invention are (A) and (B) above, although the invention can advantageously be rendered even more effective by the inclusion of auxiliary (i.e., non-essential) process steps, as hereinafter described.

A "chaotropic" salt is one which dissolves a biological source of RNA (such as cells and bacteria) and renders the RNA therein in a form suitable for selective immobilization, primarily by interrupting weak intramolecular forces generally known as van der Waal's attractions. Van der Waal's attractions, for example, are primarily responsible for holding fatty (e.g., lipid bilayer type) cellular membranes together. Chaotropic salts also solvate other types of biological molecules such as proteins. Chaotropic salts perform several functions simultaneously which make them particularly suitable for use in the present invention:

1. they dissolve cells and cellular components or other mRNA sources;
2. they tend to denature nucleic acids;
3. they allow selective nucleic acid binding to a suitable immobilizing surface.

Chaotropic salts form a reasonably select subset within all known salts. Certainly, not all salts are chaotropic and, therefore, are not suitable for use in the present invention. Chaotropic efficacy is characterized physically by a biological source substantially completely dissolving in chaotropic salt solution. Dissolution, for purposes of the invention, can be measured in terms of the amount of visible light scattered by particulate (i.e., undissolved) material. A chaotropic salt generally dissolves a biological sample to produce a substantially clear solution (although the solution may be colored). "Dissolution" may be defined as a reduction by a factor of at least about 2 in the optical density of visible light (e.g., measured at 600 millimicrons) measured for a chaotropically dissolved biological sample, relative to the optical density measured for an identical sample suspended in 5% glycerol in water. "Dissolution," for any specific salt may be operationally determined by mixing (mechanically as known in the art) one milligram of cells for each milliliter of solution at a predetermined salt concentration. For operational purposes of determining whether a salt is chaotropic, the predetermined concentration is 5 molar, although for use with actual samples the concentration can be varied to suit the nature of the biological source from which the sample is derived. If the salt is chaotropic, mixing results in "dissolution" as indicated by at least about a 2-fold reduction, relative to a suspension in 5% glycerol in water, of scattered light measured in a standard turbidimeter. A numerical illustration of this may be found in Example 7.

Specific chaotropic salts which have been tested and found suitable for use in the present invention include sodium trifluoroacetate, sodium trichloroacetate, sodium perchlorate, guanidine thiocyanate and potassium thiocyanate. In chaotropic salts having a alkali metal cation (e.g., sodium trichloroacetate), substituting a different alkali metal cation (e.g., potassium trichloracetate) makes little if any difference in chaotropic behavior.

The concentration of specific chaotropic salt sufficient to effect substantially complete dissolution of a biological source will vary depending on the specific salt and on the nature and concentration of the biological source employed. Typical concentrations of the chaotropic salt are on the order of 5 molar (see Example 6), although other salt concentrations may differ somewhat. For example, a preferred NaI solution is saturated (at 25° C.), as hereinafter described. Concentration adjustments represent routine optimization within the scope of the invention. The chaotropic salt must be in a concentration sufficient to effect substantially complete dissolution of the biological source or sample.

The term "biological source" refers to material from any living organism, but excludes purified chemicals (or biochemicals). "Biological source" particularly contemplates biological samples extracted from humans. The inventor has tested the invention using separated cells, pieces of tissue, stool, body fluids (e.g., blood, lymph, urine, saliva, etc.), bacteria, viruses, yeast, and sub-fractions (such as separated nuclei or cytoplasm) of many of the previous sources with good results. Thus, by the term "biological sample" is intended any and all of the above.

Selectively immobilizing filter materials as known in the art may be used in the invention. Preferred are those materials comprising nitrocellulose and any of the filter materials classified under the broad term "nylon." These filter materials are widely known to those skilled in the art and readily commercially available. Nitrocellulose, for example, is available as BA85 (Schleicher and Schull) and HAWP (Millipore). Nylon filters are available as Biodyne (trademark of Pall), Gensscreen (trademark of New England Nuclear), and Zetapore or Zetaprobe (trademarks of A M F Curio). Note the preceding are exemplary only. Suitable filters are available from literally dozens of commercial sources. Filter pore size is generally non-critical, 0.45M being typical. Larger or smaller pore sizes may be employed as desired.

Any "biological source" or "biological sample" which is generally a natural product (as opposed, for example, to a clean standard) will also contain DNA. By a simple procedural variation, it has been discovered that the DNA can be selectively immobilized to the exclusion of even the mRNA. By first heating a (DNA-containing) biological sample (or other source) to a temperature of at least 45° C., maintaining the temperature for a period of time sufficient to denature DNA (usually about 20 minutes) and filtering through the immobilizing filter, DNA is selectively immobilized while most other biological constituents, including mRNA, pass through. Typically the biological sample is heated to an even higher temperature of at least 75° C. to achieve DNA denaturation as quickly and as completely as possible. Thus the present invention also provides a method of selectively immobilizing DNA, comprising the steps of:

A. contacting a biological source containing DNA with a chaotropic salt solution to dissolve said source;

B. heating the thus dissolved source to a temperature of at least 45° C., followed by C. filtering said source through a filter material which selectively immobilizes said DNA.

Advantageously, a dissolved DNA-containing sample should be filtered while hot, although immobilization may still be effected once the sample has cooled, e.g., to room temperature. It is preferred to heat the dissolved source (step (B)) to as high a temperature as possible, usually at least 75° and more typically 85°–100° in order to ensure quick and complete DNA denaturation and mRNA degradation.

Once immobilized, specific RNA sequences among all the immobilized RNA can be quantitated by using a labeled DNA or RNA probe which is complementary to and hybridizes with that specific RNA sequence. In effect the probe (and label) also become immobilized, and quantity of hybridized probe (i.e., as measured by quantitating the label) is directly related to the quantity of specific RNA to which the probe hybridizes. Thus the invention also provides a method of quantitating a specific RNA sequence, comprising:

A. contacting a biological source containing RNA with a chaotropic salt solution to dissolve said source;

B. contacting the thus dissolved source with a filter which selectively immobilizes said RNA;

C. hybridizing said immobilized RNA with a labeled probe complementary to said specific RNA sequence; and D. determining the amount of said RNA based on said label.

DNA may be quantitated in a like manner, except that the procedure involves the heating step previously described. Thus the invention also provides a method for quantitating a specific DNA sequence, comprising:

A. contacting a biological source containing DNA with a chaotropic salt solution to dissolve said source;

B. heating the thus dissolved source to a temperature of at least 45° C., followed by C. contacting the thus dissolved source with a filter which selectively immobilizes said DNA;

D. hybridizing said immobilized DNA with a labeled probe complementary to said specific DNA sequence; and E. determining the amount of said specific DNA sequence based on said label.

The present invention further provides a kit suitable for effecting immobilization of a nucleic acid being selected from the group consisting of RNA and DNA, said kit separately comprising:

A. a filter comprising a material which selectively immobilizes said nucleic acid; and B. a chaotropic salt.

The present invention further provides a kit suitable for measuring the amount of any specific RNA or DNA sequence in a biological source, said kit comprising:

A. a filter comprising a material which selectively immobilizes said nucleic acid;

B. a chaotropic salt; and

C. a probe which comprises a nucleic acid complementary to said specific RNA or DNA sequence.

The invention further includes a novel method for selectively separating any specific RNA or DNA sequence from biological source, said method being identified as "reverse probing." One method of analyzing for, e.g., an RNA sequence of interest comprises immobilizing RNA from a biological sample, hybridizing the specific RNA sequence of interest to a labeled complementary probe, and quantitating the sequence of interest, as discussed above. Reverse probing is the opposite technique.

Regardless whether RNA or DNA in a nucleic acid-containing biological source is sought to be separated (and quantitated), the source is first dissolved in a chaotropic salt solution. If RNA is to be measured, a filter containing immobilized probe is subjected to the prehybridization procedure hereinafter discussed (see detailed discussion, Section 1F). Prehybridization will prevent the RNA from being immobilized directly by the filter material. If DNA is to be measured, the biological source dissolved in chaotropic solution is mixed with a detergent and the solution is also heated prior to hybridization. The detergent prevents the DNA from interacting directly with the filter material. Heating DNA denatures it so it can hybridize. Detergents such as those hereinafter mentioned are efficacious in this embodiment. Typically, an amount of detergent equivalent to 1 wt % based on the volume of the chaotropic solution (plus a dissolved source), i.e., W/V, is adequate. If the detergent is added as an aqueous solution, the volume should be kept as small as possible consistent with high hybridization rates. The solution of source as such is not filtered through the filter material, rather, it is incubated therewith at a temperature of about 37° C., typically for 20 hours, i.e., under conditions which promote hybridization.

The method for analytically determining the extent of hybridization (and therefore the amount of RNA or DNA sequence of interest in the source) is explained in Example 6.

Thus, the present invention provides a method for selectively separating any specific RNA sequence from a biological source containing said specific RNA sequence, comprising the steps of:

A. dissolving said biological source in a chaotropic solution; and

B. contacting said dissolved source with an immobilized, single-stranded, nucleic acid probe complementary to at least a portion of said RNA sequence, and incubating the source thus contacted at a temperature which promotes molecular hybridization and which maintains DNA in an undenatured state.

The present invention also provides a method for selectively separating a specific DNA sequence from a biological source, comprising the steps of:

A. dissolving a biological source containing said specific DNA sequence by contacting said source with a chaotropic salt solution containing a detergent;

B. heating the resulting solution to at least 45° C. to denature DNA; and

C. contacting said solution with an immobilized, single-stranded nucleic acid probe complementary to at least a portion of said specific DNA sequence and incubating the thus contacted source at a temperature promoting molecular hybridization.

The invention further includes a novel method for selectively separating any specific RNA or DNA from a biological source, said method being herein identified as "homogenous hybridization," "one-phase hybridization," or "liquid-liquid hybridization." By the term "homogeneous hybridization," "one-phase hybridization," or "liquid-liquid hybridization," the terms intended to be synonymous, is meant that both the labeled probe and the target (sample) nucleic acid are in solution during the molecular hybridization reaction between the two, with the molecular hybridization effected in the chaotropic solution.

Regardless of whether RNA or DNA in a nucleic acid-containing biological sample is sought to be separated for identification and/or quantification, the sample is first dissolved in a chaotropic salt solution. If RNA is to be identified and/or quantified, appropriate labeled nucleic acid probe (DNA or RNA) may be added directly to the chaotropic solution of RNA under conditions favorable for hybridization between the labeled probe and the sample RNA.

If DNA is to be measured, the biological sample is dissolved in chaotropic solution and the solution heated prior to hybridization. Heating DNA denatures the molecule, thereby presenting single stranded DNA suitable for hybridization with a suitable labeled probe. In this situation, detergents such as those utilized in the "reverse-probing" described above, are not required.

Typical methods for analytically determining the extent of hybridization (and therefore the amount of RNA or DNA sequence of interest in the sample) as above, is explained in Examples 10 and 15.

Accordingly, the present invention further provides a method for selectively separating a specific RNA sequence from a biological source containing said specific RNA sequence, or determining the presence or absence of said specific RNA sequence in the biological source, comprising the steps of:

A. dissolving said biological source in a chaotropic solution; and

B. contacting said dissolved source, in the chaotropic solution in which said dissolved source is dissolved, with a nucleic acid probe complementary to at least a portion of said RNA sequence, said nucleic acid probe in a soluble form, and incubating the sample thus contacted at a temperature which promotes molecular hybridization and which maintains DNA in an undenatured state.

The present invention further provides a method for selectively detecting and/or quantitating a specific DNA sequence from a biological sample, comprising the steps of:

A. dissolving a biological sample containing said specific DNA sequence by contacting such sample with a chaotropic salt solution;

B. heating the resulting chaotropic solution with sample DNA solubilized therein to at least 45° C. to denature said DNA; and C. contacting said solution containing said denatured sample with a labeled nucleic acid probe complementary to at least a portion of said specific DNA sequence and incubating the thus contacted sample at a temperature promoting molecular hybridization.

The present invention further provides a kit suitable for effecting sample preparation and homogeneous hybridization for evaluating nucleic acids being selected from the group consisting of RNA and DNA, said kit separately comprising:

A. A chaotropic salt;

B. Paraphernalia for conducting molecular hybridization; and

C. An assay for detecting and/or quantitating hybridized duplexes.

The present invention further provides a kit suitable for measuring the amount of specific RNA or DNA sequence, said kit comprising:

A. A chaotropic salt;

B. Paraphernalia for conducting molecular hybridization;

C. An assay for detecting and/or quantitating hybridized duplexes;

D. A probe which comprises a nucleic acid complementary to said specific RNA or DNA sequence; and E. Positive and negative control biological samples, dissolved in chaotrope.

As discussed above, this homogeneous hybridization provides the particular advantage that the analytical determination of type and/or contact of nucleic acid in a given sample is especially adapted for clinical application. The present invention, combining sample preparation and homogeneous hybridization in substantially the same chaotrope solution, is unique in its ability to retain the accuracy and sensitivity of the most advanced laboratory procedures while possessing the speed, simplicity, economy, versatile and automatability necessary for clinical adaption. For ease of understanding the invention and its novelty, the above parameters are summarized regarding the invention and cross-referenced to pertinent examples of experimentation.

Accuracy—Hybridization in chaotropes operates at 100% efficiency on purified nucleic acids (Example 10, FIG. 9B, upper curve) and operates with equal efficiency on nucleic acids in biological sources (Example 10, FIG. 9C). Hybridization in liquid can be described mathematically (Britten and Kohne, Science 161:529, 1968). The present invention performs hybridizations which conform to he mathematical model (Example 12, FIG. 11). At probe excess, there is a linear relationship between amount of target nucleic acid present and amount of probe hybridized and the proportionality constant is 1 (Example 10, FIG. 9B, upper curve). With lower amounts of probe, there is still a linear relation between amount of target nucleic acid present and amount of probe hybridized (Example 15, FIG. 12). All of these facts show that the present invention can provide an accurate evaluation of nucleic acids in a biological sample. Example 16 illustrates this in a practical way. (FIG. 13).

Sensitivity—Thirty fentograms of complementary target sequence was detected (Example 10). This level of sensitivity is state of the art at the moment.

Speed—Regardless of the paucity of target sequence, the invention provides a means for completing sample preparation/hybridization in 15 minutes for target DNA in bacteria (Example 10, FIG. 9D) and in 11 minutes for target DNA in human lymphocytes (Example 10). It follows that target RNA can be evaluated in 6 minutes, since the procedure is identical except that a 5 minute incubation is omitted, but this is not exemplified in the application. It is important to note that full accuracy and sensitivity is retained in these high-speed experiments. One reason the above-mentioned speed is possible is through the unexpected acceleration of hybridization afforded by chaotropes generally (Example 11, FIGS. 10A and 10B) and by GuSCN particularly (Example 11 and 12, FIGS. 10 and 11).

Simplicity—The present invention for evaluating target RNA in a biological sample requires only: 1) contacting a fluid or finely divided tissue with a strong chaotrope for about 1 minute then 2) adding a probe to about 1 ug/ml and incubating the mixture for about 5 minutes. This is exemplified in Examples 15 and 16, except that the hybridization step was prolonged because low amounts of probe were used. It will be obvious to those skilled in the art from Example 10 that had larger amounts of probe been used in Examples 15 and 16, hybridization could have been abbreviated. Further, the probe may be pre-mixed with the chaotrope and the two added simultaneously.

The procedure is simple enough for unskilled persons to perform and, in fact, has been performed in the inventor's laboratory by a junior high school student, a high school student, and a college undergraduate.

The procedure is not sensitive to perturbations of conditions expected in a clinical laboratory. The process is equally effective from 3–6.5M GuSCN when conducted at ambient temperature (Example 12, FIG. 11C) and using 3–4M GuSCN is equally efficient from 23°–30° C. (Example 12, FIGS. 11 A, B). Hybridizations can be conducted for 5 minutes or several days (See Example 11, FIGS. 10A, B and compare with Example 10, FIG. 9D).

That such an extraordinarily simple process would suffice for sample preparation and molecular hybridization was not anticipated by the prior art. Combinations of enzymes, detergents, organic solvents, reducing agents, etc., are usually used during sample preparation. Conditions are ordinarily changed and are quite specific for conducting molecular hybridization. Since target nucleic acids in biological samples are complexed to other macromolecules through many kinds of forces, including ionic bonds, hydrogen bonds and nonpolar bonds, it could not be anticipated that an exposure of a biological sample to a chaotrope would free said target nucleic acids to the extent that they could be probed accurately, efficiently and sensitively. Certainly, it could not be anticipated that such probing could proceed in substantially exactly the same solution used for sample processing. And finally, it could not be anticipated that the rate of the probing process would be accelerated by the chaotrope, providing a faster process.

It should be noted that the simplicity of the chaotrope process was obtained at no sacrifice of accuracy, sensitivity or speed.

Economy—The cost of the chaotrope procedure is lower than all other procedures known to the inventor. Holding such costs as probe costs, hybrid detection costs, sample collection device costs as equal among all systems, the cost of the chaotrope system is the cost of the chaotrope itself, a cost amounting to pennies or fractions thereof per assay. A manual gene diagnosis test using the chaotrope system has been estimated as costing under $1.50 to conduct. The cost of an automated test is not readily calculated, but given the simplicity of the present invention, should be relatively low.

Versatility—Clinical samples are commonly termed "dirty" when compared to research laboratory samples because of the high levels of impurities in such samples as stools, blood, urine, etc. The present invention has been tested across the spectrum of clinical samples and found to operate efficiently in all cases. The inventor is aware neither of prior art achieving this versatility nor of prior art anticipating this versatility. It was quite unexpected to the inventor.

It should be emphasized that, to the best of the inventor's experience, this versatility was obtained with no sacrifice in accuracy, sensitivity, speed, simplicity or economy. Consequently, the present invention unexpectedly embodied the best of all those characteristics which characterize a clinically applicable gene diagnosis process.

Automatability—Until such automation actually exists, it is difficult to argue which of several processes is easiest to automate. It will be obvious to those skilled in the art, however, that the simplicity of the present invention lends itself to automation.

The invention further provides a means for detecting and quantitating HIV nucleic acids in patients.

BRIEF DESCRIPTION OF THE DRAWINGS

FIG. 5 is a radioautograph showing detection of Hepatitis B virus DNA in human blood platelets;

9A=pure target DNA, radioautograph

9B=pure target DNA, graphical representation of scintillation counting target

9C=target DNA mixed with cells, radioautograph

9D=target DNA in bacteria, radioautograph

Figure 10A:
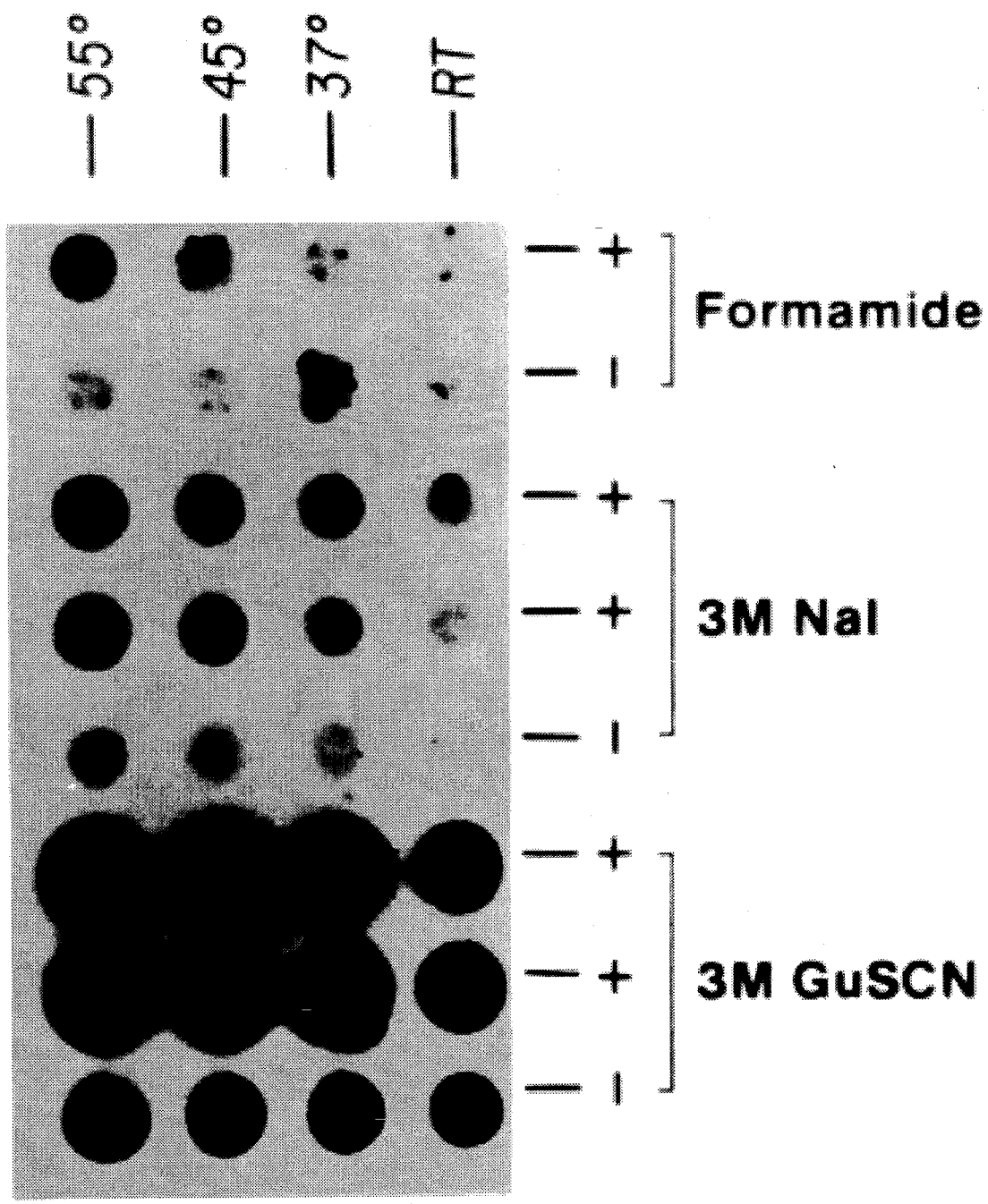
Figure 10B:
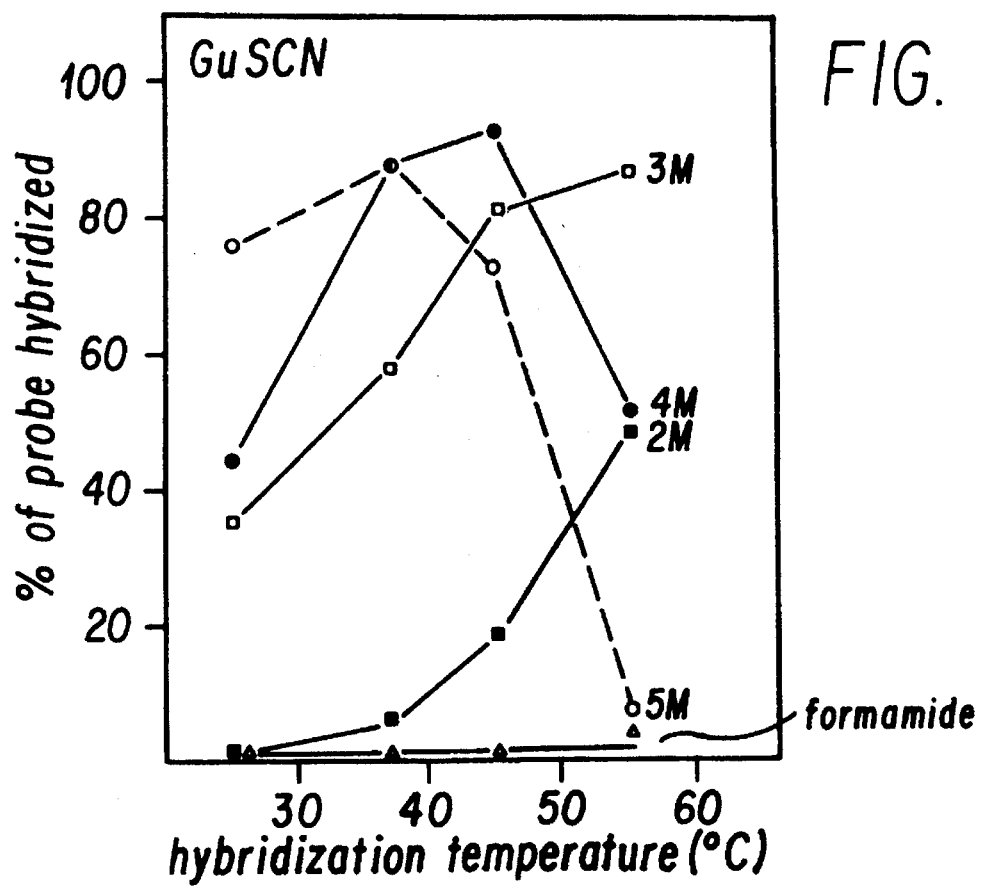
Figure 10C:
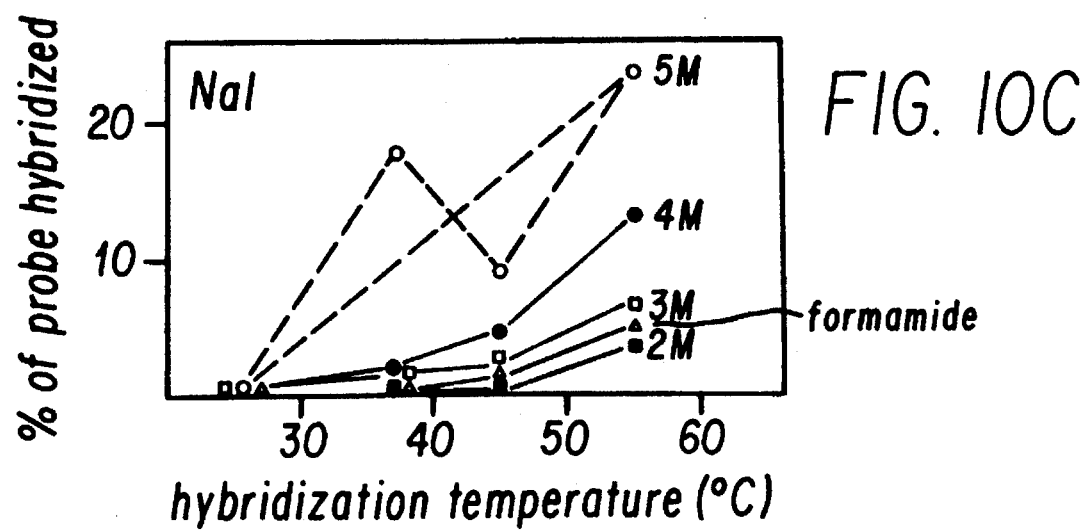
Figure 11B:
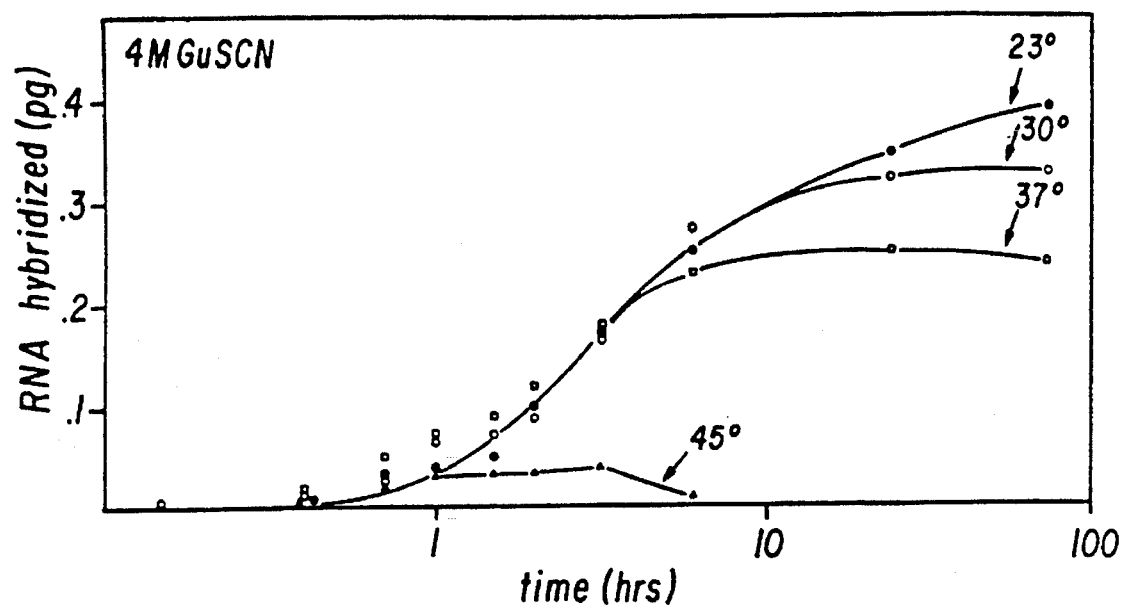
Figure 11A:
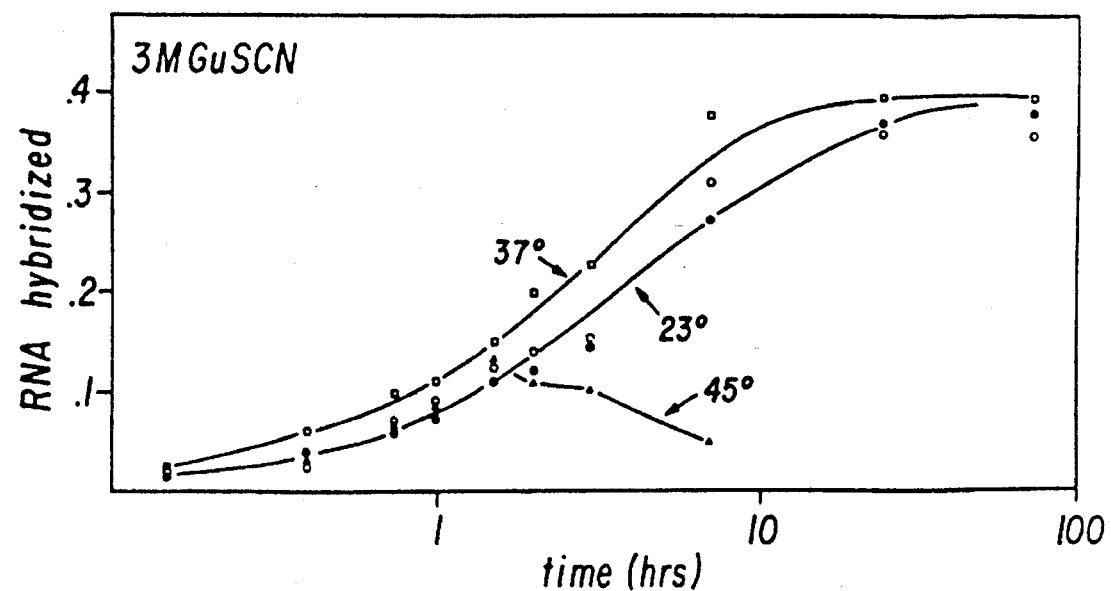
Figure 11C:
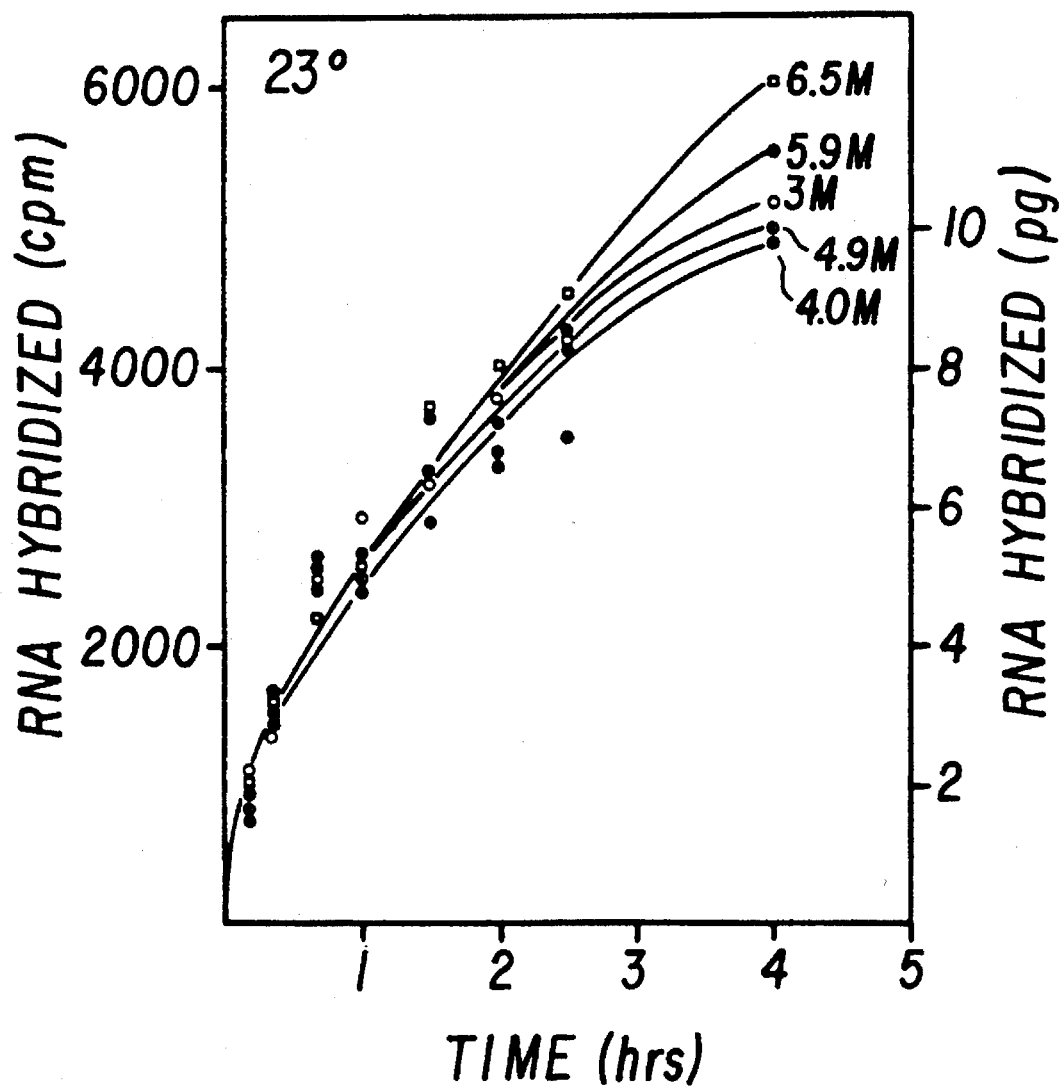

FIGS. 10A–10C represent the efficiency of the invention:

10A=comparison of hybridization in 3M GuSCN, or NaI, or in 50% formamide, radioautograph 10B,C=hybridization of various concentrations of GuSCN or NaI at different temperatures, graphical representation of scintillation counting FIGS. 11A–11C are graphical illustrations of the kinetics of hybridization in GuSCN:

11A=kinetics in 3M GuSCN at 23°, 37°, and 45° C.

11B=kinetics in 4M GuSCN at 23°, 30°, 37°, and 45° C.

Figure 12:
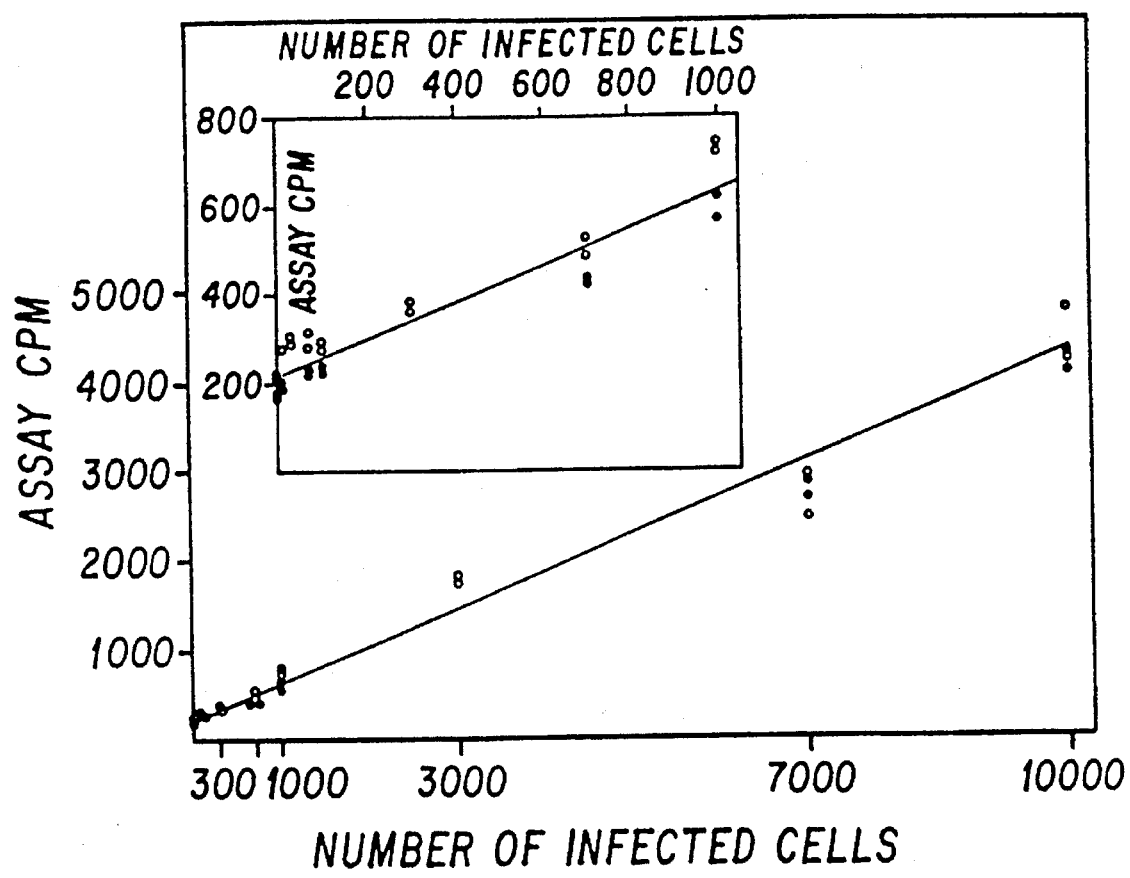

11C=kinetics in 3, 4, 4.9, 5.9, 6.5M GuSCN at 23° C.;

FIG. 12 is a graphical illustration of the relationship between the number of virus infected cells dissolved in GuSCN and hybridization values.

Figure 13:
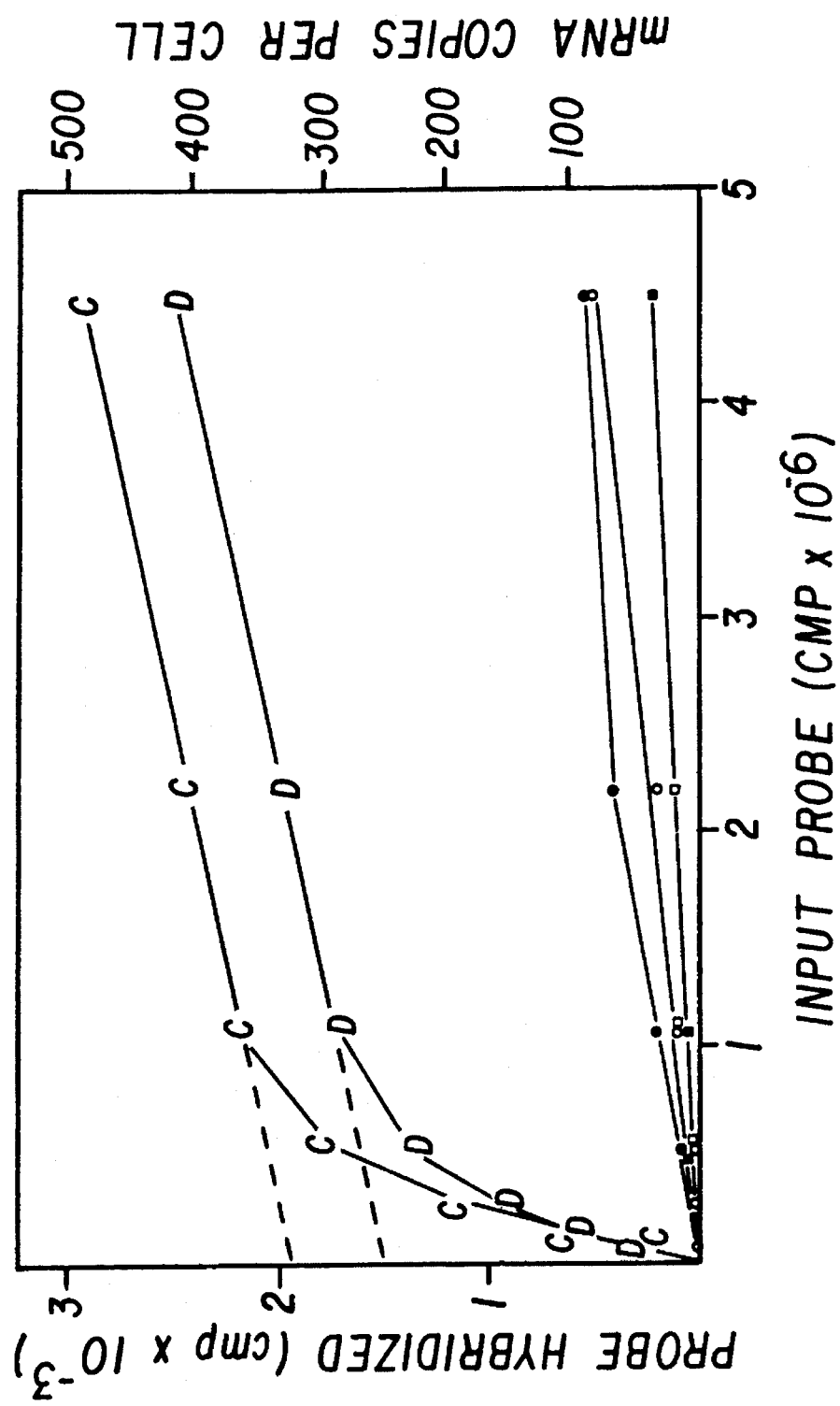
Figures 14A, 14B, 14C, 14D:
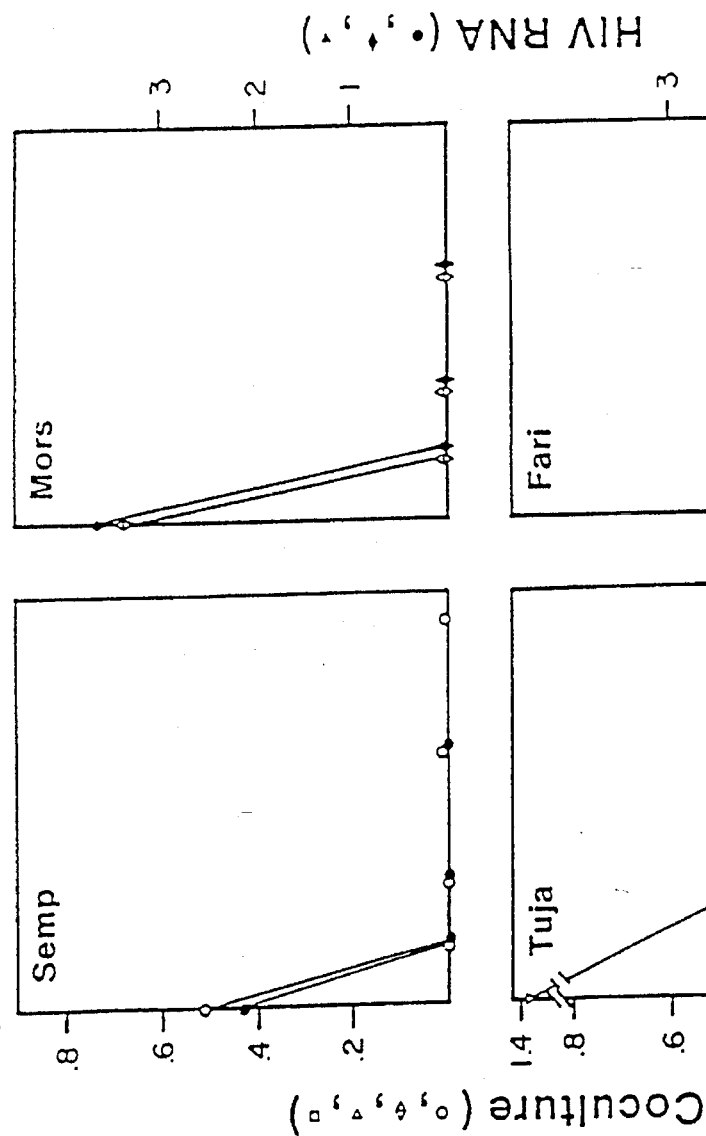

FIG. 13 is a graphical illustration of the relationship between the amount of probe used and hybridization values, demonstrating how to use saturation values to evaluate the number of target RNA molecules present in a biological sample.

FIGS. 14A, 14B, 14C and 14D. Coculture and HIV values obtained on four ARC patients with no detectable serum antigen prior to treatment.

Figure 15A:
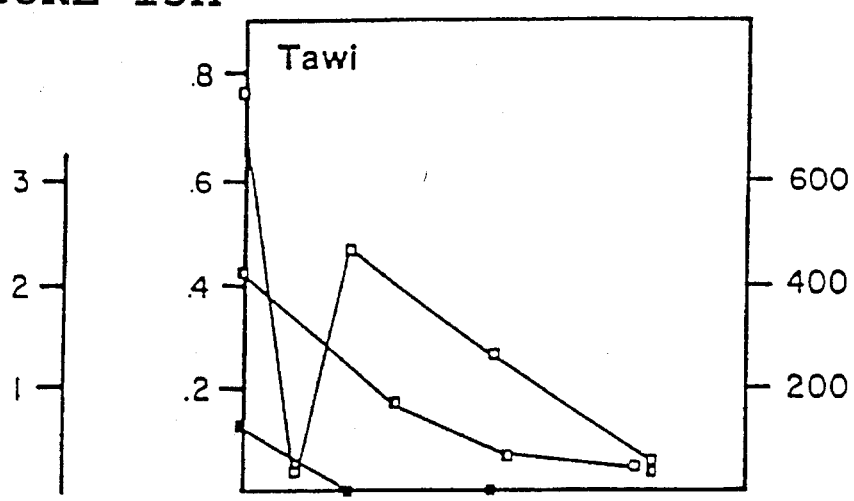
Figure 15B:
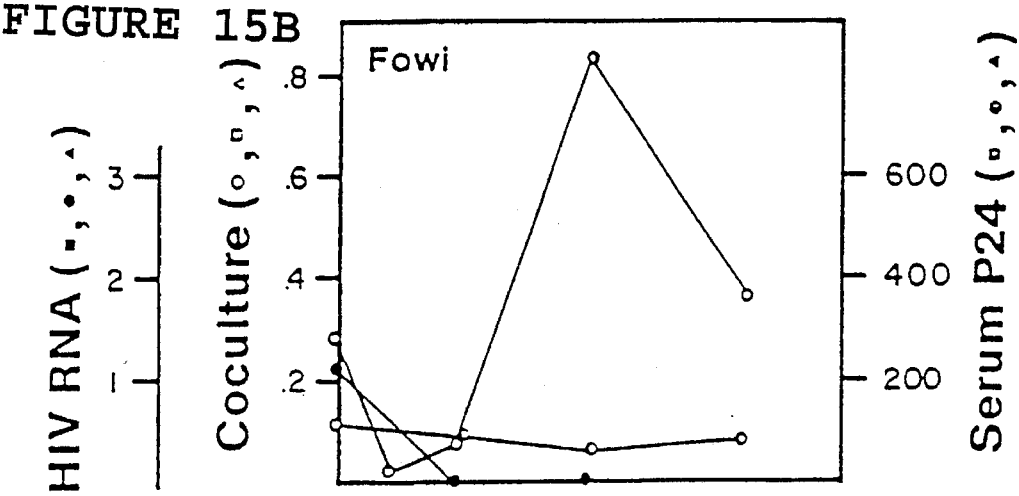
Figure 15C:
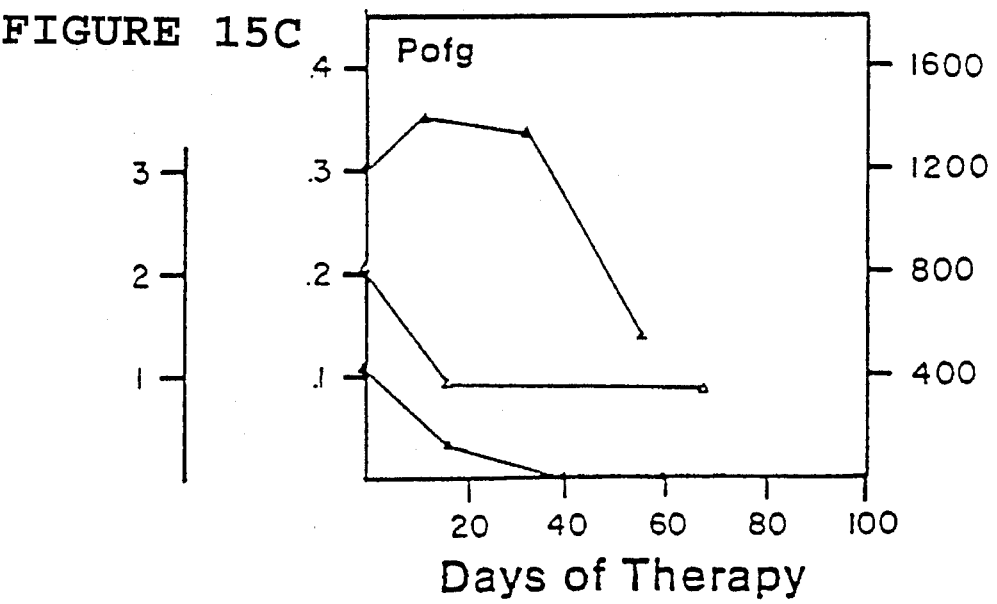

FIGS. 15A, 15B, and 15C. Coculture, hybridization, and antigen results obtained with three ARC patients who had detectable serum antigen prior to treatment.

Figure 16A:
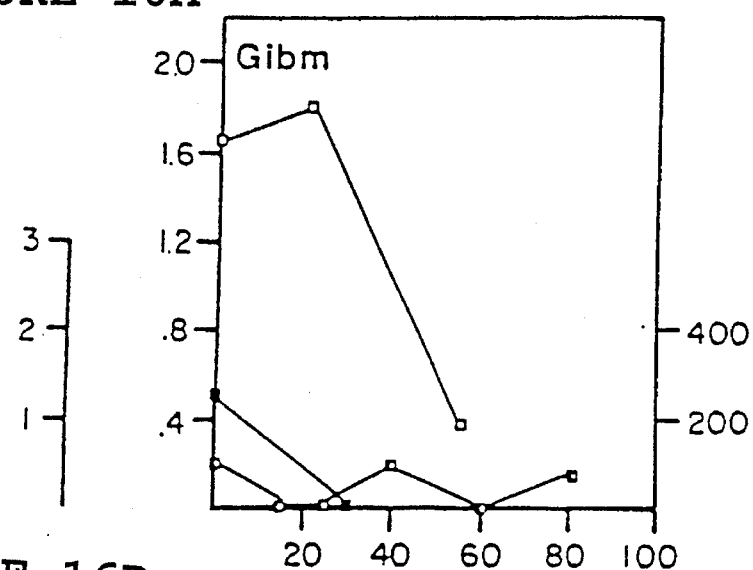
Figure 16B:
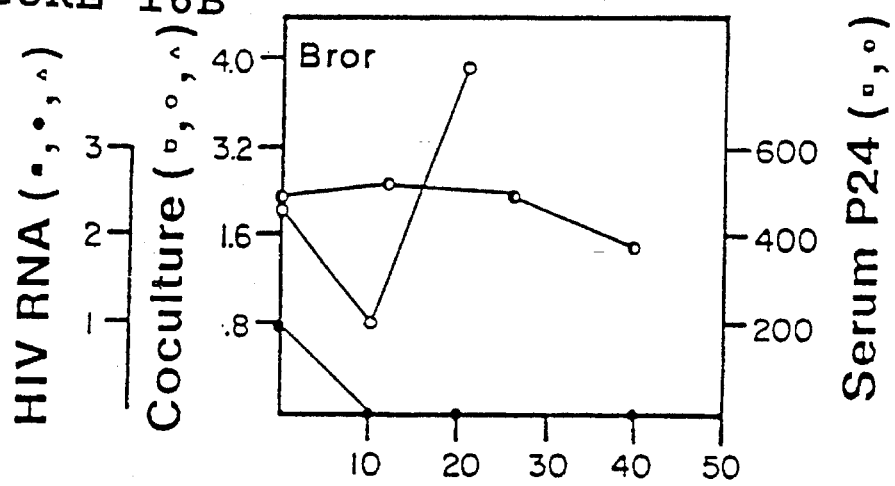
Figure 16C:
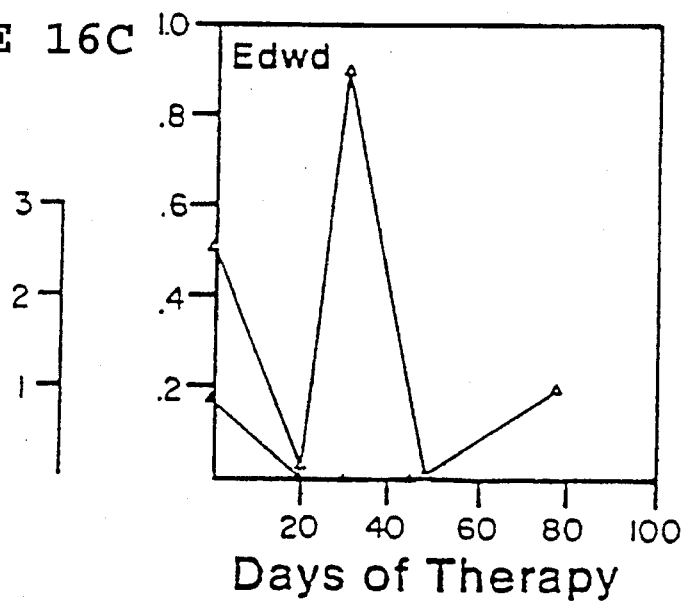

FIGS. 16A, 16B and 16C. Coculture, hybridization, and antigen results obtained with three AIDS patients.

DETAILED DISCUSSIONS

All temperatures stated herein are Centigrade unless otherwise indicated. "NC" refers to membranes containing nitrocellulose.

1. mRNA immobilization procedure for molecular hybridization with auxiliary steps (see Example 1)

Message RNA can be selectively immobilized from whole cells according to the following procedure:

(a) prepare biological source (b) deproteinize enzymatically (c) add detergents (d) add chaotropic salt (e) filter through immobilizing membrane (f) wash filter (e.g., soak filter in $H_2O$, $EtOH/H_2O$, acetic anhydride)

(g) perform molecular hybridization

Of the above steps, (d) and (e) are essential, as previously noted. Steps (a)–(c) and (f) represent auxiliary, non-essential procedures which, depending on the nature of the mRNA source, can be used to enhance the effectiveness of mRNA immobilization as hereinafter explained. Step (g) is the hybridization step which enables quantitation.

a. Biological Source Preparation

"Preparation" as used herein refers to manipulations required to get the mRNA source in a state suitable for mRNA immobilization while maintaining the primary structural integrity of nucleic acids, insofar as possible. Typical cell preparation manipulations can include removal of fluids from cell or tissue samples, removal of cells or particles from body fluids, preparation of subfractions from cells, fluids, etc. Some examples are illustrated below. Cells can be prepared by any convenient means, providing that care is taken to stabilize mRNA by preventing its structural degradation. Usually, this is accomplished by working with the sample on ice, wearing gloves throughout the procedure, and including cyclohexamide plus ribonuclease inhibitors in solutions which come in contact with cells. Cyclohexamide protects mRNA derived from cells by maintaining the mRNA within a natural structure on ribosomes. Ribonuclease inhibitors reduce the degradation of mRNA by ribonucleases. The ribonuclease inhibitor vanadyl ribonucleosides, prepared by the method of Berger and Birkenmeyer, is satisfactory but remains associated with NC. Vanadyl ribonucleosides will not interfere with molecular hybridization, but they will inhibit reverse transcription and translation of immobilized mRNA. The combination of 0.5 mM aurin tricarboxylic acid (Sigma Chemicals) plus 1 mM hydroxystilbamidine isothamine (Merrell) or 1 U/ml RNAs in (Promega Biotech) do not have this inhibitory action, but they may not be as potent ribonuclease inhibitors as vanadyl ribonucleosides.

If the sample contains mononuclear blood or bone marrow cells, these can be prepared by discontinuous density gradient centrifugation in Ficoll Hypaque (see Example 1). Monolayer cells grown in tissue culture can be released in the usual way with trypsin but this enzymatic treatment does not substitute for the later protease step. Solid tissues may be dissolved directly in a chaotropic salt solution or disassociated to single cells prior to immobilizing. This can be done enzymatically, with DNAase and collagenase (Slocum et al., *Cancer Res.* 41:1428–1434), but low speed blending or freezing and pulverizing can also be effective. A nearly infinite variety of source preparation steps can be imagined and, to the best of the inventors' knowledge, all of them are compatible with the present invention.

b. Deproteinization

Even though the bulk of proteinaceous material passes through NC after a biological sample has been dissolved in chaotropic salt solution, enough protein, depending on the nature and amount of the biological sample, may coimmobilize with mRNA so that it is sometimes advisable to degrade as much protein as early in the procedure before filtration as possible. This is conveniently done by adding proteolytic enzymes (called proteases) to prepared cells which are suspended as described above and incubating the cell suspension at 37° for 30 minutes, Proteinase K (Sigma), for example, can be used at about 200 ug/ml. Pronase B (RNAase-free, Calbiochem) is another example of a commercially useful protease, and should be used at 1 mg/ml after a stock 10 mg/ml solution is prepared and incubated for 30 minutes at 37° (Gillespie and Spiegelman, *J. Mol. Biol.* 12:829–842, 1965). If subcellular fractionation (see below) is desired, the protease step should be delayed.

Addition of detergents (c) and chaotropic salt (d)

The order of addition of detergents and chaotropic salt to a solution is not critical. Either can be added first, followed by the other, or they can be added together.

Detergents disrupt cells and help suppress protein and DNA immobilization from the chaotropic salt solution.

If the nature of the mRNA source is such that high amounts of protein and/or DNA are available, then addition of a detergent is advisable. Suitable detergents are well known to the art and commercially available. Preferred are non-ionic detergents such as polyoxyethylenes available commercially as the Brij series (Sigma) or the Tween series (Sigma). Weakly ionic detergents such a sodium lauryl sarcosinate and sodium desoxycholate also function well. Less preferred but usable if necessary are strongly anionic detergents such as sodium dodecyl sulfate and strongly cationic detergents such as cetyl trimethyl ammonium bromide. Mixtures of detergents can also be employed.

For example, to disrupt cells, add 1/20 vol (note "vol" whenever used herein refers to the sample volume at that point in the procedure) of 10% Brij 35 (Sigma) and mix the sample. Then add 1/20 vol of 10% sodium desoxycholate (Sigma) and mix the sample again. The amount of detergent which should be added is typically that given above but can depend on the nature of the sample (e.g., blood versus organ tissue) and may be adjusted by means of simple experiments or "trial runs," and is well within the scope of the invention.

Following detergent addition, if needed, add 1 vol of supersaturated chaotropic salt solution to make the cell extract approximately saturated with respect to the chaotropic salt. The strong salt solutions are easily prepared. Using NaI as an example, supersaturated NaI is conveniently prepared by dissolving NaI in hot water (at least 75° C.) in a ratio (W/V) of 2.5 gmNaI (Baker) to each ml of hot $H_2O$. The solution can be stored solid at room temperature, then melted by heating to at least 75° prior to use. A saturated NaI solution is prepared by adding about 1 vol of supersaturated NaI to an NaI-free solution, suspension, biological source, etc. A clear amber solution should result from the addition of 1 vol of supersaturated NaI to suspended cells, tissue sample, or body fluid. Dilutions can be made at this stage into saturated NaI. Similar procedures can be used with the other chaotropic salts, adjusting, of course, for different molecular weights and solubilities, and hence different W/Vs. Making the solution "saturated" in the chaotropic salt is a desirable procedure because of its ease, its reproducibility, and the efficacy of saturated solutions. Lesser concentrations can also be used if desired, however.

e. Filtration through a nucleic acid-immobilized membrane

Note that the terms "filter" and "membrane" are used interchangeably herein. Most membranes, including nitrocellulose (NC) and nylon, may be prepared for immobilizing nucleic acids by wetting them in RNAase-free $H_2O$, then soaking them for 5 minutes or more in RNAase-free 6×SSC. Some hydrophobic membranes may need to be prewet in an alcohol such as ethanol. Membranes can be stored in 6×SSC for several days, at least. In some way, exposure of membranes to a strong NaCl solution activates the membrane for interaction with nucleic acids dissolved in the chaotropic salt solution. Filtration can be performed through dry membranes but considerable lateral diffusion of mRNA occurs, and immobilization may not be quantitative.

Some nucleic acid immobilization procedures (i.e., for mRNA or DNA) will involve filtering several dilutions and/or multiple cell samples. For this reason, manifold devices containing 72–96 wells designed for filtration of large numbers of samples are optimal for the present invention. The Minifold I™ manufactured by Schleicher and Schuell, is particularly suitable because each well has a rather large surface area. The membrane is typically laid on the vacuum chamber of the device over a piece of blotting paper prewet in 6×SSC. The manifold plate is clamped over the membrane and the samples are filtered through the membrane under vacuum.

f. Washing RNA-containing membranes

The purpose of the washing steps is to remove NaI and non-nucleic acid molecules from the membrane. It is again emphasized that this step is auxiliary, the extent to which it is desirable being determined by the nature of the biological sample being assayed. To remove residual chaotropic salt as well as contaminants in the mRNA source the mRNA filter can b,a successively soaked in $H_2O$, 70% ethanol/30% $H_2O$ and acetic anhydride. The mRNA filter can be removed form the manifold assembly and placed directly in a tray containing 1–2 ml of $H_2O$ per $cm^2$ of membrane. Reasonable caution should be taken to exclude contact between ribonucleases and the mRNA filter, despite observations that mRNA immobilized on NC in chaotropic salt solution is remarkably resistant to ribonuclease A. Gloves should be worn, the mRNA filter should be handled with clean tweezers and RNAase-free $H_2O$ should be used. The mRNA filter is soaked for at least 5 minutes at room temperature, then the wash solution is changed. Multiple filters can be soaked in a single tray. Filters can be accumulated in the first water wash or, preferably, in the first ethanol wash. Overall, the filter should be soaked in three changes of water, three changes of 70% ethanol/30% $H_2O$, and once in acetic anhydride.

The acetic anhydride wash can be important for molecular hybridization experiments. Acetic anhydride acetylates basic proteins, minimizing the formation of nonspecific probe-protein complexes and, through a still unknown means, may enhance the molecular hybridization signal. Acetic anhydride is unstable in $H_2O$ so stock solutions cannot be made and stored. The acetic anhydride solution is conveniently made by adding 0.25 ml of pure acetic anhydride (Fisher Chemicals) to 100 ml of 0.1M triethanolamine (Fisher Chemicals). The solution is vigorously mixed, placed in a clean tray, and the mRNA filter is immediately added. The acetic anhydride soak should be prolonged for 10 minutes at room temperature.

mRNA filters can be removed from acetic anhydride and used immediately or they can be air-dried and stored refrigerated in zip-lock bags. When replicate samples are prepared, it is convenient to number and separate the replicates before storage. Stored filters should be well-dried to discourage microorganism growth. Whether they are used immediately or stored, the mRNA filters are now ready for molecular hybridization.

It should be noted that the concentrations of proteases, ribonuclease inhibitors, and detergents added in auxiliary steps (a), (b), and (c) can be varied depending on the nature of the biological source, and that the values cited herein are intended to be exemplary. Such variation represents routine optimization well within the capabilities of those skilled in the art.

g. Molecular hybridization of immobilized mRNA

One of the major uses for immobilized DNA or RNA is in determining the quantity of one or a few specific sequences which are present among the total nucleic acid population. Thus, among millions of genes immobilized from a typical mammalian cell, gene probing can detect the presence and determine the quantity of a single gene. And among hundreds to hundreds of thousands of mRNA species immobilized from various kinds of mammalian cells, gene probing can detect the presence and determine the quantity of a single mRNA. This is because, for the most part, each gene and each mRNA species possess a unique nucleotide sequence which can be uniquely and quantitatively recognized by a labeled gene probe through an interactive process called molecular hybridization. Molecular hybridization is a process which is well known in the field of molecular biology for 20 years (see Gillespie, D., and Spiegelman, S., *J. Mol. Biol.* 12:829–842, 1965; Gillespie, D., *Methods Enzymol.* 12B:641–668, 1968; Seed, B., *Genetic Engineering* 4:91–102, 1982; Lehninger, A. L., *Biochemistry Text* (Worth Publishers), pp. 882–883, 1975; Stryer, L., *Biochemistry Text* (Freeman and Co.), pp. 600–601, 1975). It involves the formation of hydrogen bonds between two nucleic acids with complementary nucleotide sequences such as is found in the opposite strands of any region of DNA (Watson, J. D., and Crick, F. H. C., *Nature* 71:737–738, 1953). Thus a labeled probe consisting of one DNA strand or its chemical equivalent (e.g., RNA or modified DNA or RNA of the same nucleotide sequence) can be used to detect and quantitate immobilized DNA or RNA with a complementary or nearly complementary nucleotide sequence.

Molecular hybridization is not, of course, part of the procedure for immobilizing mRNA. Rather, it is a procedural step which allows a specific immobilized mRNA sequence (among many others which would also be immobilized) to be determined. The hybridization is performed by pairing labeled DNA or mRNA (i.e., the probe), which is complementary (i.e., specific) to the mRNA sequence of interest, to the mRNA. Quantitation of the label is directly related to the quantity of the immobilized mRNA sequence of interest. Many labels are possible, such as those falling within the broad categories of radioactive, fluorescent, and enzymatic. For ease of exemplification, hybridization employing radioactive labels will be discussed, but this is not to be taken as limiting.

Many systems have been described for molecular hybridization using radioactive DNA probes. Commonly, the procedure is carried out in three steps: (a) soak the mRNA filter in a solution lacking probe which will minimize interactions between radioactive DNA (the probe) and the membrane ("prehybridization"); (b) incubate the mRNA filter in a solution containing probe which will encourage hybridization between radioactive DNA and mRNA ("hybridization"); and (c) wash away unhybridized probe ("posthybridization"). Commonly used prehybridization solutions which minimize interactions between radioactive DNA and NC generally contain the following ingredients: 0.2% bovine serum albumin (fraction IV, Sigma), 0.2% Ficoll (Type 400, Pharmacia), 0.2% polyvinylpyrollidone (Sigma), 50 ug/ml of low molecular weight DNA (e.g., sonicated salmon sperm DNA, Sigma) and 50 ug/ml of poly(A) (Collaborative Research). Presumably, all of these molecules occupy various sites on the NC which might attract the radioactive probe so that the only possible reactions left will occur during hybridization between the probe and immobilize mRNA. Prehybridization is conveniently accomplished by sealing one or more filters in a seal-a-meal (e.g., Sears) bag with about 1 ml/$cm^2$ of NC of a prehybridization solution containing the ingredients listed above. The sealed sack can then be incubated for several hours at the same temperature as will be used for hybridization.

For hybridization, the filter-containing sack is simply opened, drained, replaced with a small volume (0.1–0.2 ml/$cm^2$ NC) of hybridization solution and reincubated with gentle shaking. A preferred solution for hybridization of immobilized nucleic acid contains (final concentrations): 50% formamide, pH 7 (Flukka-Granite), 0.45M NaCl, 0.045M sodium citrate, 0.05M sodium phosphate, pH 7.0, 1% SDS (Sigma), and $10^6$–$10^7$ cpm/ml of DNA probe. Hybridization is normally conducted overnight at 42° in this solution, though temperatures as low as 20°–25° have been successfully used. Higher temperatures provide more specific hybridization.

The nature and amount of formamide are important. Formamide taken directly from the bottle which exhibits a high pH on pH paper will strip immobilized mRNA from its solid support. Similarly, very high concentrations of formamide, even very pure formamide of neutral pH, will remove mRNA from filters. It has not proven to be necessary to redistill or deionize formamide when conducting hybridization, but it is important to test the contents of each bottle periodically for pH and it is wise to pour from the stock formamide bottle, rather than pipette from it. Pure formamide can be stored in dark bottles at room temperature for a small number of weeks; prolonged storage should be at a lower temperature in darkness.

The nature of the DNA probe is also important. Many procedures are now available for the synthesis and purification of DNA probes and new procedures appear continually. The primary criteria for a satisfactory probe are that it be of sufficient chain length to support molecular hybridization (>20 nucleotides) and that it be relatively free of labeled material which will interact with the filter. In terms of probe synthesis, nick-translation can conveniently be accomplished through the use of commercial kits (Amersham) while oligonucleotide-primed copying of gel-purified, denatured DNA still requires individual components (Feinberg and Vogelstein, *Anal. Biochem.* 132:6–13, 1983). Two useful steps for purification of nick-translated DNA are molecular sieving through Sephadex G-100 (Pharmacia) followed by filtration through NC (Maniatis et al., *Molecular Cloning: A Laboratory Manual*, pp. 466–467, 1982). Purified probe is denatured at 100° for 10 minutes, chilled and added last to the hybridization solution.

For posthybridization, filters can be soaked a number of times in 10×SSC plus 0.1% SDS. The time and temperature requirements for these soaks varies with the nature of the probes and cellular samples. Usually three soaks of 30 minutes each at 42° is sufficient to remove unhybridized probe. For quantitation of rare mRNA, it may be necessary to undertake repeated soakings at elevated temperatures for longer times. In any event, these soaks should be followed by a 60 minute soak at 600 in 0.015M NaCl, 0.0015M sodium citrate and 1% SDS to remove the last traces of unhybridized probe and to remove probe which has made nonspecific hydrogen bonds with immobilized mRNA. As mentioned above, many systems have been developed for conducting molecular hybridization, including systems containing formamide, urea, ethanol, dimethylsulfoxide, guanidine hydrochloride or high temperatures. All of these systems have been successfully employed with mRNA or DNA immobilized with the present invention.

As will be apparent to one with ordinary skill in the art, procedures similar to those described above, modified appropriately with regard to the particular biological sample and particular RNA being sought (i.e., rRNA from a bacterial source, genomic RNA, mRNA, tRNA and hnRNA) are included within the scope of this invention.

2. DNA immobilization for molecular hybridization with auxiliary steps (See Example 1)

Denatured DNA can be selectively immobilized (even to the exclusion of mRNA) from a biological source such as whole cells according to the following immobilization procedure. Either linear or covalently closed circular DNA can be immobilized quantitatively (Bresser and Gillespie, *Anal. Biochem.* 129:357–364, 1983). The procedure is exactly that described for mRNA immobilization, except that a freeze-thaw step may be included to rupture cells, all detergents are omitted, a heat step is included to denature DNA and the filtration may be carried out with a hot solution. The procedure can include the following steps:

(a) Prepare cells (b) Deproteinize enzymatically, freeze-thaw (c) Add NaI, incubate for 20 minutes at 95°–100°

(d) Filter through a membrane, preferably while solution is still hot (e) Soak filter in $H_2O$, EtOH/$H_2O$, acetic anhydride (f) Perform molecular hybridization Steps (c) and (d) are essential to the immobilization procedure; steps (a), (b), and (e) are auxiliary, and can advantageously be used depending on the nature of the biological sample (i.e., the DNA source) to make the procedure even more efficacious.

a) Preparation of Cells. The procedure can be exactly as described for "mRNA Immobilization," above. Nuclease and protein synthesis inhibitors are not necessary but do not interfere. Cells do not need to be worked up quickly as in the case of mRNA immobilization; in fact, freezer specimens can be analyzed.

b) Deproteinization. See "mRNA Immobilization." Protease-digested cells are disrupted by cycles of freezing and thawing. A freezing bath containing methanol, ethanol, or acetone is brought out to −80° with dry ice. Cells are frozen by plunging the test tube containing them in the freezing bath until the entire suspension reaches minimum temperature, usually 5–10 minutes, until the inverted cone at the liquid surface forms and is completely frozen. The cells are thawed in a water bath maintained at room temperature. Three cycles of freeze-thaw should be used to ensure complete disruption of the cells. Other methods of cell lysis such as homogenization, high pressures, shear forces, etc. can be used with equal success.

c) Addition of chaotropic salt solution and incubation. One volume of supersaturated chaotropic salt solution is added to deproteinized, freeze-thawed cells. The solution is thoroughly mixed, then placed in a hot water bath maintained at 85°–1000° and held there for about 20 minutes, although lower temperatures (as low as 45°) can also be used. Higher temperatures are preferred to ensure quick and complete DNA denaturation. During this period DNA not only denatures, but mRNA is also degraded.

d) Filtration through membranes. Membranes are prepared as described for "mRNA Immobilization." The chaotropic solution used to dissolve the biological source is heated to a temperature of at least 45° C. and preferably at least 750° C., the hot chaotropic salt solution is then sampled from the test tube and an aliquot is filtered immediately. Typically an aliquot is removed from the chaotropic salt solution at a temperature as high as possible (without boiling or bumping), usually 85°–100° C. Using a dispenser such as a Finnpipette or a Pipetteman (Brinkman Instruments) and transferring the solution quickly from a hot bath to NC affixed to a vacuum manifold at room temperature maintains a solution temperature of over 50° during filtration, ensuring quantitative DNA immobilization.

e) Washing DNA-containing membranes. The wash procedure is identical to that described under "mRNA Immobilization."

f) Molecular hybridization of immobilized DNA. The hybridization procedure is identical to that described under "Standard mRNA Immobilization." Detergents can be included during molecular hybridization since DNA is not removed by detergents even though the presence of detergents discourages DNA-NC interactions.

3. mRNA Immobilization from subcellular fractions (See Example 1)

The subcellular immobilization procedure is compatible with several methods of subcellular fractionation. Detailed below is a typical protocol for mRNA immobilization from cytoplasmic and nuclear fractions prepared from detergent-lysed cells. The following procedure is exemplary. As before, steps (e) and (f) represent the core of the procedure:

a) Prepare cells b) Add detergents c) Separate nuclear and cytoplasmic components d) Deproteinize enzymatically e) Add 1 volume of saturated chaotropic salt solution f) Filter through NC g) Soak filter in $H_2O$, EtOH/$H_2O$, acetic anhydride h) Perform molecular hybridization a) Preparation of cells. Single cell suspensions are prepared exactly as described for "mRNA Immobilization." Ribonuclease inhibitors should be included and care should be exercised to minimize degradation in vivo.

b) Addition of detergents. The plasma and outer nuclear membranes are disrupted by the sequential addition of Brij 35 and DOC (Bresser et al., *DNA* 2:243–254, 1983). One-twentieth volume of 10% Brij 35 is added to prepared cells and the suspension is mixed and held on ice for 5 minutes. One-twentieth volume of DOC is added and the suspension is mixed. Steps should be conscientiously taken to prevent RNA degradation. Ribonucleases should be kept from all detergent solutions. Gloves should be worn continuously. The cell sample should be kept cold and the operations should be performed rapidly.

c) Separate cytoplasmic and nuclear fractions. Centrifuge disrupted cells for 20 minutes at 0° and 2500×g to pellet nuclei. Save the cytoplasm supernatant. Suspend the nuclear pellet as described for cells in 1*b* and add Brij 35 to 0.5% and DOC to 0.5%.

All of the remaining steps are carried out exactly as described for "Standard mRNA Immobilization," except that the deproteinization step is delayed until after detergents have been added.

Those skilled in the art will readily appreciate that DNA from subcellular fractions can likewise be selectively immobilized by leaving out detergents (using another method like homogenization to rupture the plasma membrane) and by including a heating step immediately prior to filtration, completely analogous to DNA immobilization, as previously discussed.

4) Data Handling from Molecular Hybridization.

Results from molecular hybridizations with immobilized mRNA or DNA can take any of several forms, including radioautographs, densitometer tracings, scintillation counts, etc. All these forms are familiar to those skilled in the art and are consistent with the present invention. For clarity, examples are illustrated below.

The first piece of data to emerge from a hybridization experiment using, for example, a $^{32}$P-labeled probe is typically a radioautograph. Radioautography can be conducted at −70° with an x-ray intensifying screen. The radioautograph serves to show that the probe interacts only with DNA- or mRNA-containing portions of the membrane, that the hybridization response properly diminishes as the mRNA or DNA source is diluted, that no lateral diffusion of the sample has occurred, etc. Additionally, crude comparisons of specific mRNA or DNA sequences amount can be made.

When exact quantitation is desired, individual dots can be excised and evaluated. For radioactive probes (e.g., $^{32}$P), this is economically done by placing a membrane square containing one dot in a 500 ul plastic tube (Eppendorf) which is in turn placed in a scintillation vial. The filter can then be counted dry on an $^3$H setting (50% efficiency), in water on an $^3$H setting (80% efficiency) or in scintillation fluid on a $^{32}$P setting (100% efficiency). The quantity of mRNA is then calculated from the relationship between probe radioactivity hybridized versus mRNA dilution, providing this relationship is linear. The most common nonlinear this relationship is linear. The most common nonlinear results are low hybridization values at high inputs of cellular material from interference by coimmobilized contaminants and positive values upon extrapolation to zero mRNA from impurities in the probe which interact with the membrane. Interference is minimized by effective proteolysis prior to chaotropic salt addition, sufficient washing of the mRNA filter with water and ethanol/water and routinely including the acetylation step. When it occurs it is easily corrected for by using the most dilute samples to calculate the hybridization signal. Direct probe membrane interactions ("background") are minimized by changing probe purification methods. One effective step is to formamide hybridization, either in dilute aqueous solutions (u<0.05) or in hybridization buffer. Background is compensated for by subtracting from all points the positive value observed at zero mRNA input.

Results can be expressed as units of probe hybridization per cell equivalent of mRNA immobilized. In the absence of a reference, this parameter is of minimal value because it fails to take into account variations in efficiency of mRNA immobilization probe characteristics, hybridization efficiency, counting efficiency, etc. A more useful value is units of probe hybridized per cell equivalent mRNA immobilized during one physiological condition compared to the same value obtained during other physiological conditions. With this latter value such things as the effect of chemicals, temperature, pH, etc., on level of expression of a given gene can be measured as can variations in expression during development, differentiation, aging, etc. However, this value does not take into account variations in immobilization efficiency and cannot be compared with values from a separate experiment because of possible differences in hybridization efficiency. Neither of the two values described above can be converted to number of molecules of a given mRNA per cell.

An internal mRNA reference can provide more information. Replicate immobilizations can be made: one to be hybridized to the test probe, the other to be hybridized to one or more reference probes. Results are then expressed as the ratio of hybridization values from a test probe to hybridization values from reference probe. One good reference would be an mRNA whose number/cell is known under a variety of conditions in the cells being studied. A second reference is the poly(A) tract of mRNA which is probably an indicator of total mRNA content. Detection of poly(A) by hybridization with radioactive poly(T) 9s somewhat difficult to use as a reference in that different hybridization conditions must be used (e.g., lower temperatures) than would be used with probes for specific mRNA. mRNA references all suffer from the need to use a different probe for the reference than would be used for test mRNA; therefore, differences in probe characteristics which results in different hybridization values can complicate measurements.

An internal DNA reference may provide more satisfactory information. By changing the immobilization conditions only slightly, DNA can be immobilized. Basically, cells are lysed by freeze-thaw rather than with detergents and the samples are filtered after an incubation at high temperature rather than being kept at ambient temperature. Thus, mRNA and DNA from the same number of the same cells can be immobilized on different spots of the same membrane and hybridized together with a given probe. One can then generate a ratio of probe hybridization to mRNA/probe hybridization to DNA. If the number of hybridizing sequences in DNA is known and if the efficiency of hybridization of the probe to mRNA versus DNA is known, the mRNA/DNA hybridization ratio translates immediately into the number of mRNA molecules per cell. Possible confusion arising from specific gene amplification or deletion is compensated for by hybridizing replicate mRNA/DNA immobilizations to other probes, for example probes which measure highly repeated DNA sequences.

A parallel test with positive and negative control biological samples having known quantities of a specific mRNA or DNA sequence provides satisfactory numerical information. Typically, such control samples are provided dissolved in chaotrope. These controls have the advantage that the same probe is employed as is used on the unknown sample. For best quantitation, an excess of probe over target nucleic acids should be used.

There are many ways to express results obtained from this invention. Different situations will demand different formats. An all-or-none phenomenon like virus infection may be assessed by visual inspection of a radioautograph (resulting from a hybridization of immobilized DNA or mRNA from a biological source to a viral-specific probe); whereas an increase in expression of a cellular gene may require numerical quantitation as described above.

5) Preparation of mRNA for Reverse Transcription or Translation mRNA filters to be used for reverse-transcriptions or translations are washed three times in RNAase-free dH$_2$O). Filters may then be used immediately for the reverse transcription or translation reactions or air dried and stored in zip-lock bags at 4° C.

Washed filters are placed in a heat resealable plastic bag or plastic test tube and thoroughly wetted with ribonuclease-free distilled water (dH$_2$O). Filters are then washed for 30–60 minutes at room temperature in ribonuclease-free dH$_2$O containing 09.2% BSA, 0.2% Ficoll (type 400), and 0.2% polyvinylpyrollidone. The solution is then removed and the filter is rinsed with ribonuclease-free dH$_2$O. The use of salt-containing solutions should be avoided in preparing mRNA filters for reverse-transcription or translation; unless the salts are volatile.

6) Reverse Transcription.

Transcription is the biological process wherein mRNA is synthesized (i.e., transcribed) from information supplied from a DNA template. Reverse transcription is the synthesis of a new DNA template from already existing mRNA. mRNA immobilized according to the present invention may be used to effect reverse transcription, the following being an exemplary description of a suitable procedure which is not, however, intended to be limiting.

In a separate plastic tube approximately 100 pmoles of lyophilized [alpha-$^{32}$P] TTP (sp. act.>2000 Ci/mM) is resuspended in 1000 mM Tris-HCl pH 8.3, 10 mMMgCl$_2$, 100 ug/ml oligo(dT)$_{12-8}$ (Sigma), 150 mM KCl, and 1 mM of each dNTP. This solution (0.1 ml/cm$^2$ of NC) is added to the mRNA filter, 1000 U/ml of AMV reverse transcriptase (Life Sciences, St. Petersburg, Fla.) is added and the filter is incubated at 42° C. for 1–3 hours with gentle shaking. The reaction is stopped by the addition of EDTA (pH 8.0) to 50 mM. The reverse transcription cocktail is removed from the bag and saved. $^{32}$P cDNA may be removed from the NC by placing the mRNA-cDNA filter in 5 mM sodium phosphate buffer (pH 78.0) at 100° for 30 seconds. The $^{32}$P cDNA may be analyzed by electrophoresis, used as a hybridization probe, or used in a cDNA cloning scheme.

7) In Vitro Translation.

Translation is the process whereby the information coded by mRNA is used to synthesize polypeptides. An exemplary non-limiting procedure whereby mRNA may be translated as follows.

In a plastic tube $^{35}$S or $^3$H labeled amino acids are lyophilized and resuspended with RNAase-free dH$_2$O (about 20 of the initial volume). A commercial rabbit reticulocyte lysate (Amersham) is added such that the lysate is 80% of the final volume. The mixture is added to the mRNA filter and incubated at 30° for 1–3 hours with gentle agitation. The reaction is terminated and the aminoacyl-tRNA complexes are hydrolyzed by placing the filter in a 37° C. water bath for 10 minutes followed by a 42° C. water bath for 10 minutes. The solution is removed and the labeled polypeptides may be analyzed by any number of means including electrophoresis into polyacrylamide.

8) Recovery of RNA from Membranes mRNA can be recovered from NC after immobilization in chaotropic salt solution by soaking the mRNA-NC in a hydrogen bond breaking solvent such as 100% formamide or dimethyl sulfoxide. An exemplary procedure is:

a) Release the RNA with formamide b) Precipitate the RNA from ethanol c) Remove "soluble" membrane components d) Precipitate the RNA from ethanol a) Release the RNA with formamide. This is accomplished by incubating mRNA-membrane in 1 ml of pure formamide/cm$^2$ of membrane at room temperature for 30 minute. The filter is removed mechanically. The solution consists of mRNA and filter material which has been dissolved in the formamide. This filter material is insoluble in ethanol and in aqueous solutions at or below 25°, but is soluble in aqueous solutions at or above 45°.

b) RNA precipition. Dilute the RNA with 5 volumes of cold 400 mM NH$_4$Ac, add to the resultant solution 2 volumes of cold ethanol, allow the precipitate to form in the cold (e.g., at −20° overnight or −70° for 30 minutes) and collect it by centrifugation at 10,000×g for 30 minutes at 0°. Discard the supernatant c) Removal of insoluble nitrocellulose. Dissolve the RNA pellet at 45° in 400 mM NH$_4$Ac, 50 mM Tris, pH 8 and 10 mMEDTA. Chill the solution to 0° and clarify by centrifugation at 10,000×g for 10 minutes. Discard the pellet.

d) Precipitation of RNA. Add 2 volumes of cold ethanol, allow the RNA precipitate to form in the cold and collect it by centrifugation as above. Discard the supernatant, dry the precipitate and dissolve the mRNA pellet in any convenient buffer.

The use of volatile NH$_4$Ac, rather than NaCl, is important in maintaining low salt concentrations at later steps.

The resulting mRNA preparation can be reverse transcribed into DNA or translated into protein. It remains unknown whether released RNA can be analyzed electrophoretically.

9) Recycling of mRNA-NC

After molecular hybridization, the probe can be removed from the membrane without severing the mRNA-membrane link. Such "recycled" mRNA-membrane can be used again for molecular hybridization or can be used as a template for DNA or protein synthesis on the membrane. To remove the probe the membrane is dipped for 30 seconds into a very dilute salt solution (e.g., 0.01×SSPE; 0.15 mM NaCitrate, 1.5 mM NaCl, 0.5 mM sodium phosphate, 0.1 mM EDTA, pH 7) maintained at 100°. The filter is then soaked briefly in prehybridization solution in preparation for rehybridization (see above) or is soaked in appropriate solutions in preparation for reverse transcription or translation (see above).

10) Kits for Immobilizing and Quantitating mRNA and DNA

An exemplary kit for immobilizing mRNA or DNA according to the present invention can contain at least one plastic vial (or other suitable receptacle or container) containing a detergent such as 0.5 ml of 10% Brig 35 and, if subcellular fractionation is to be performed, at least one plastic vial containing an additional detergent such as 0.5 ml of 10% sodium desoxycholate, at least one amber glass vial containing about 7 ml of supersaturated NaI (12.5 gm NaI dissolved in 5 ml of hot water, allowed to solidify at room temperature), one or more amber glass vials containing 100 ml of saturated NaI (12.2 molal in $h_2O$), one or more amber glass vials containing 10 ml of saturated NaI plus 1 Brij 58 and 4"×5" sheets of nitrocellulose. Note that in lieu of including salt solutions, the dry salt may equivalently be included and the user can make his or her own solutions, as desired. Solutions are advantageously pre prepared, however, particularly when analysis is to be performed on samples from sources for which efficacious chaotropic salt concentrations are known (i.e., no "trial runs" are needed to determine minimum or optimum salt concentrations). Depending on the sample to be analyzed, it may also be advantageous to include separate vials of at least one ribonuclease inhibitor (or solutions thereof), proteases (or solutions thereof), and detergents in amounts or concentrations sufficient, respectively, to inhibit ribonucleases, degrade proteins and improve immobilization selectivity.

Appropriate instructions for using the reagents may also be included. The instructions can consist of, for example: A. Introduction, B. An Overview of the Instructions for mRNA immobilization, C. complete Instructions for use, D. Optional Procedures, and an Appendix specifying dilution schedules. An exemplary text of instructions (c) for preparing four replicates of DNA and mRNA from whole cells follows:

MAXI QUICK-BLOT™

(four dilutions, four replicates)

Whole Cells—Divide into 2 aliquots of 90 ul each (Whole cell concentration may range from $10^1$ to $10^5$ cells/ul)

mRNA Samples

1. Add 10 ul of protease solution, mix.
2. Go on to Step 3.
3. Incubate at 37° for 30 minutes.
4. Add 5 ul of reagent A, vortex.
5. Add 5 ul of reagent B, vortex.
6. Add 100 ul of reagent C, mix.
7. Add 200 ul of reagent D, mix.
8. Prepare dilutions into reagent D according to Appendix 1, Schedule
9. Go on to Step 10.
10. Filter 50 ul aliquots through mRNC nitrocellulose, using S&S Minifold apparatus.
11. Soak membrane at room temperature in three changes of RNAase-free water, 5 minutes per change.
12. Soak membrane at room temperature in three changes of 70% ethanol/30% water, 5 minutes per change.
13. Soak membrane at room temperature in freshly prepared acetic anhydride solution for 10 minutes.
14. Air-dry membrane.
15. Cut membrane with S&S template (SRC 096/l), if desired.
16. Store dried filters refrigerated in a heat-sealable or zip-lock bag.

DNA Sample

1. Add 10 ul of protease solution, mix.
2. Freeze-thaw three times.
3. Incubate at 37° for 30 minutes.
4. Add 10 ul of RNase-free water.
5. Go on to step 6.
6. Add 100 ul of reagent C, mix.
7. Add 200 ul of reagent E, mix.
8. Prepare dilutions into reagent E according to Appendix 1, Schedule B.
9. Heat to 90°–100° for 10 minutes.
10. Filter 50 ul aliquots while hot through mRNC nitrocellulose, using S&S Minifold apparatus.
11. Soak membrane at room temperature in three changes of RNase-free water, 5 minutes per change.
12. Soak membrane at room temperature in three changes of 70 ethanol/30% water, 5 minutes per change.
13. Soak membrane at room temperature in freshly prepared acetic anhydride solution for 10 minutes.
14. Air-dry membrane.
15. Cut membrane with S&S template (SRC 096/l), if desired.
16. Store dried filter refrigerated in a heat-sealable or zip-lock bag.

Note:

Reagent A is 10% Brij 35.

Reagent B is 10% sodium desoxycholate.

Reagent C is supersaturated NaI.

Reagent D is supersaturated NaI containing 1% Brij 58.

Reagent E is saturated NaI.

The immobilizing filter (or sheet of filter material from which a filter can be quickly made as known in the art) and chaotropic salt represent the minimum components for inclusion in the kit of this invention. Other elements may also optionally be included, such as a suitable probe for quantitatively detecting a specific mRNA or DNA sequence of interest, detergents, proteases and so forth. Each of the individual components—chaotropic salt or solution thereof), detergent, protease, ribonuclease inhibitor, probe, etc.—is present in its own container (such as a vial). Particular combinations of vials can be unitarily packaged (e.g., in a suitable box or other container or package which may be custom designed to hold a certain number and kind or size of vial), depending on the particular biological source to be analyzed, or on other factors, and the kit contents can be varied to suit particular analytical requirements.

Clearly, many such variations are possible within the framework of the present invention. For example, as previously discussed, no detergents, other detergents, other membranes, and other chaotropic solutions can be employed (i.e., substituted as equivalents) in the kit with good results. The detergents, protease, dilution and soaking steps can be omitted. Operations other than molecular hybridization can be done on the immobilized DNA or mRNA.

Those skilled in the art will appreciate that the present invention also discloses how to prepare specialized kits (i.e., a kit designed to analyze only a particular part of biological source such as blood and/or to detect a specific predetermined mRNA or DNA sequence associated with a particular disease or condition). Such special kits can advantageously:

1. Specify the nature and amount of the most suitable mRNA source or DNA source;
2. Supply detailed information for preparing the source;
3. Contain those detergents, chaotropic salts and membranes most suitable for utilizing the invention on the source;
4. Contain a specific probe complementary to the mRNA or DNA sequence of interest;
5. Specify the most effective conditions for membrane washing, molecular hybridization and data handling pertinent to the mRNA and DNA; and 6. Provide information relating to possible results obtained by using the special kit to a pathological situation.

For example, a special kit may be constructed for the detection of hepatitis virus mRNA or DNA. For evaluating heavy drinkers at risk of hepatocarcinoma, such a kit can, for example, specify $10^6$ mononuclear blood cells for obtaining the mononuclear cells (see Example 1). The special kit may include Brij 58 as a detergent, sodium iodide as a chaotropic salt, and nylon membranes. The special kit may contain a probe consisting of a cloned hepatitis virus genome such as that used in Example 3. The probe can be supplied in a lyophilized state with instructions describing proper means for dissolving the probe. If the probe is furnished in an unlabeled state, instructions and/or reagents for labeling the probe may also be provided. Suitable labeling methods are familiar to those skilled in the art. The special kit may specify a "stringent" molecular hybridization conditions (e.g., high temperature) such as the conditions found to be advantageous in Example 3. The special kit may include items of result interpretation such as a statement that positive molecular hybridization results show the presence of hepatitis virus DNA in the individual's blood cells and demonstrate that the individual has been infected by the virus even if conventional immunological tests indicate that no virus is present.

The above-specialized kit is presented as exemplary, for illustrative purposes. Specialized kits can be constructed for evaluating the presence and quantitating any desired mRNA or DNA sequence. The advantageous of each and all such special kits is the ability to efficiently and selectively immobilize mRNA or DNA from an mRNA source or DNA source.

11) Molecular hybridization of solubilized sample nucleic acid

In another embodiment of this invention, previously disclosed in application Ser. No. 594,308, said application having been filed on Mar. 8, 1984, a biological sample may be evaluated by a method wherein the biological sample containing 1 or more nucleic acid sequences of interest is prepared by dissolving the sample in a chaotropic salt solution. The nucleic acid sequence of interest (the target nucleic acid sequence) is probed in the chaotropic medium representing the prepared sample utilizing a labeled nucleic acid probe which is complementary to the target nucleic acid sequence.

By the term "evaluated" is intended the detection and/or quantification of target nucleic acid. Accordingly, samples suspected of containing a nucleic acid sequence may be evaluated for the presence or absence of the sequence. Similarly, the sample may also be evaluated by quantifying the amount of target nucleic acid contained in the sample.

Where the sample is being evaluated for the detection of a suspected target nucleic acid sequence, the prepared biological sample may be incubated with a labeled nucleic acid probe containing a nucleic acid sequence which is complementary to the sequence being detected under conditions which will promote hybridization between the target nucleic acid sequence, if present, and the labeled nucleic acid probe. Subsequent to the incubation period, the sample may be tested for the presence or absence of hybridized probe.

Where the sample is to be evaluated in the sense of quantification of the target nucleic acid, quantification of hybridized probe utilizes techniques known to the art.

A collection of various methods for detecting hybridized duplexes can be found in the book "Nucleic Acid Hybridization" (Hames and Haggis, eds.; IRL Press, Washington, D.C., 1985) and in section 1f of "Detailed Discussions," above.

By the term "biological sample" is intended the same material as described above, i.e., separated cells, pieces of tissue, stool, body fluids (e.g., blood, lymph, urine, saliva, etc.), bacteria, viruses, yeast, and subfractions (such as separated nuclei or cytoplasm). See section 1a, "Detailed Discussions," this application.

By the term "solubilizing" is intended that the target nucleic acid be sufficiently separated from other cellular components as to enable the efficient hybridization of said target nucleic acid with labeled nucleic acid complementary thereto while still maintaining the primary structural integrity of the nucleic acids, insofar as possible. See Sections 1a, 1d, "Detailed Discussions," this application.

By the term "contacting" is intended that the biological sample and the chaotropic solution be juxtaposed in such a manner as to permit the dissolution of the sample in the chaotropic solution. Typically, the biological sample is introduced into a container of the chaotropic salt solution.

By the term "chaotropic salt" is intended a salt selected from the group consisting of sodium iodide, sodium perchlorate, potassium iodide, sodium thiocyanate, potassium thiocyanate, guanidine thiocyanate, sodium trichloroacetate, and sodium trifluoroacetate, in concentrations sufficient to achieve the "dissolution" of sample described in the SUMMARY OF THE INVENTION. Other alkali metal salts of the above anions may be used as well. Guanidine thiocyanate is the preferred chaotropic salt.

By the term "nucleic acid probe" is intended any nucleic acid sequence, DNA, or RNA, or modification thereof in labeled form, which will hybridize to at least a portion of the target nucleic acid sequence. The resulting "hybridized duplex" may be a DNA-RNA duplex, a DNA-DNA duplex, or an RNA-RNA duplex.

By the term "complementary" is intended that the target sequence and probe sequence demonstrate sufficient base-pair matching to enable duplex formation under hybridization conditions. It is not required, however, that the base-pair matchings be exact. See section 1f, "Detailed Discussions," this application. Generally speaking, each 10% mismatching between probe and target will retard hybridization rates by a factor of 2 and will lower the Tm of the hybridized duplex by 10° C. (Refer to "nucleic acid hybridization," ibid pp. 7, 8.)

By the term "conditions which promote molecular hybridization" is intended those conditions known to the art or disclosed in this application for promoting hybridization between two DNA sequences, to RNA sequences, or an RNA and a DNA sequence.

As is known to the art, where one intends to probe for target RNA sequence in the presence of double-stranded DNA sequence, the hybridization conditions must ordinarily be such that the double-stranded DNA sequences remain double-stranded. Similarly, where one intends to probe for a DNA sequence in the presence of RNA sequence, double-stranded DNA must be denatured and then probed under conditions wherein hybridization between probe and any RNA present is avoided or is not detected.

By the term "detecting" is intended both the actual detection and quantification of molecular hybridization. Typical methods known to the art include hydroxyapatite chromatography, enzymic digestion of unpaired probe, membrane filtration, electrophoresis, etc. (refer to "Nucleic Acid Hybridization," ibid. chapters 1–4).

In accordance with this aspect of the invention, the target nucleic acid is solubilized utilizing a chaotropic salt solution as described above and then incubated with a labeled nucleic acid probe. The labeled nucleic acid may be in immobilized or soluble form. The embodiment wherein the labeled nucleic acid probe is in insoluble form is termed "reverse-probing" for the purposes of this invention. Reverse-probing is described below in Example 4.

The embodiment wherein molecular hybridization is achieved under conditions of solution homogeneity, where both the target nucleic acid sequence and the nucleic acid probe are in solution is also introduced in Example 4 and expanded upon in other examples. The invention is typically as follows. A biological sample is first made ready for use. Body fluids are used as is or after fractionation into components such as plasma, cell-free filtrate, etc., which are done by methods which are standard in the art. Cells are made ready by pelleting them from a body fluid or laboratory Solution or by suspending such pellets in a laboratory solution, again using standard techniques. Samples of solid tissue are converted to single cell suspension enzymatically or are converted to a suspension or a paste-like consistency by grinding, pulverizing, blending, or homogenizing. These methods are also standard in the art.

The biological sample is then contacted with a chaotropic ion. Guanidine thiocyanate is the preferred chaotropic ion. Typically, the biological source is made approximately 5M in guanidine thiocyanate at room temperature. For solutions or suspensions this is accomplished by adding 0.4 volumes of said solution or suspension to about 1 volume of 7M guanidine thiocyanate and mixing to substantially dissolved solids. For cell pellets or tissue samples converted to a paste-like consistency, a solution of 5M guanidine thiocyanate is added and the resulting mixture is mixed until solids are substantially dissolved. Other chaotropes than saturated sodium iodide or guanidine thiocyanate have been used to prepare biological samples, such as 6M sodium trifluoroacetate, 5M sodium trichloroacetate, and 5M sodium perchlorate.

As is known in the art, other additives may be added to aid sample dissolution and/or preservation of molecular components as desired. Surfactants including ionic detergents typified by sodium dodecyl sulphate or non-ionic detergents typified by Brij 35 have been successfully used. The use of detergents and nuclease inhibitors in sodium iodide-containing solutions is known to the art. The use of hydrogen bond breakers and detergents to help dissolve cellular samples is well-known in the art as well.

A novel aspect of the present invention is that the act of dissolving a biological sample in a strong solution of chaotrope renders nucleic acids in said biological source available for probing using the process of molecular hybridization. After the biological source is substantially dissolved, molecular hybridization is achieved simply by adding a gene probe, and incubating the solution or suspension at ambient or a mildly elevated temperature, typically 20°–37° C. for a time ranging from a few minutes to several hours. Specific examples of liquid-liquid hybridization are provided below. Alternatively, the probe may be added as a part of the chaotropic solution.

The liquid-liquid hybridization assay of the present invention is suitable for DNA or RNA evaluation of a biological sample. Hybrids were formed between $^{32}$P-labeled RNA probes and nucleic acids in cell lysates. Animal cells or lysozyme-treated bacteria were harvested by centrifugation and dissolved in 5M GuSCN/0.1M EDTA with or without 1M NaCl at a rate of 1 ml of solvent per $10^7$ cells. Cells dissolved readily at room temperature after 2–3 minutes of agitation, yielding a clear moderately viscous, amber solution. Dissolved cells were stored at −70°, except when being thawed to remove aliquots for assays. The Isolution viscosity decreased after 1–2 freeze thaws.

TARGET DNA. Hybridization of RNA probes with target DNA was accomplished by gently heating the dissolved cells to 60° or above for 5 minutes to denature DNA, adding probe, incubating at room temperature or above and trapping probe RNA: target DNA hybrids on a nitrocellulose membrane as detailed in Example 10. Typically, the equivalent of $10^5$ peripheral blood lymphocytes were dissolved in 10 ul of 5M GuSCN/0.1M EDTA. Two and one-half microliters containing 5 ng of RNA probe diluted in 2×SSC/0.1M EDTA were added and hybridization was accomplished at 25° for 5 minutes. Hybrids were visualized by scintillation counting or radioautography.

RNA. Hybridization of RNA probes with target RNA was accomplished by adding probe to dissolved cells, incubating at room temperature or above, degrading unhybridized probe with RNAase, precipitating hybridized probe with TCA and collecting the precipitate on a nitrocellulose membrane as described in Example 15. Typically, the equivalent of $10^5$ peripheral blood lymphocytes is dissolved in 10 ul of 5M GuSCN/0.1M EDTA. Two and one-half microliters of 2×SSC/0.1M EDTA containing 5 mg of probe is added and hybridization is accomplished at 25° for 5 minutes. Hybrids are visualized by scintillation counting or radioautography.

Regarding handling of data from the liquid-liquid version of the present invention, substantially the same rules apply as were described above in section 4 of "Detailed Discussions," this application.

Several chaotropic salts have been successfully utilized for sample preparation (see Example 6) and two, NaI and GuSCN, have been tested for supporting molecular hybridization (see Example 11, FIG. 10). Both chaotropic salts worked well, giving better molecular hybridization results than the standard systems (formamide and phosphate), but GuSCN was preferred because it unexpectedly accelerated the rate of molecular hybridization over 100-fold, as compared to the NaI system.

12) Kits for molecular hybridization of solubilized sample nucleic acid

An exemplary kit for molecular hybridization of solubilized sample nucleic acid according to the present invention can contain at least dark plastic vial of solid GuSCN and solid tetrasodium EDTA to which $H_2O$ or a body fluid can be added to provide a solution of 5M GuSCN/0.1M EDTA. Should $H_{20}$ be added, the resulting solution can be added to a biological sample at a rate of 1 ml per $10^7$ cells or the equivalent to provide a solubilized biological sample. Alternatively, a premade solution of chaotrope can be provided. Said kit can also contain a probe for evaluating a given sequence in the biological sample, said probe provided in a quantity to perform about 20 tests (e.g., 100 ng of probe). Said probe can be provided ready to use (e.g., already labeled) or in a precursor form suitable for labeling by the user. The probe may also be a part of the chaotropic solution.

Said kit can also contain "positive control" and "negative control" biological samples dissolved in chaotrope, said biological samples possessing known quantities of specific nucleic acids and results of molecular hybridizations performed on said samples yielding numerical references for quantitating results on unknown test biological samples.

Said kit can also contain materials and devices for hybrid detection, for example filtration solutions, blocking agents, membranes, nuclease solutions, trichloracetic acid, hydroxyapatite, etc.

The present invention further is suitable for detecting and quantitating HIV nucleic acids in patients. One dilemma of evaluating HIV load in ARC-risk, ARC, or AIDS diagnosis is that direct tests of virus antigens or virus infectivity may be difficult or impossible in a percentage of cases because viremia is transient and opposed to varying degrees during the diseases by natural immune mechanisms. This difficulty will be exacerbated if patients are treated with or are induced to develop antiviral antibodies. Moreover, nonproductively infected cells (e.g., harboring latent or defective virus) could contribute to diseases without presenting viral antigens or rescuable infectious centers. However, the sensitivity, speed, versatility, and automatability of the present invention makes such detection and quantitation possible.

Having now generally described the invention, the same will be more fully understood by reference to the following examples which are provided herein for purposes of illustration only and are not intended to be limiting unless otherwise specified.

EXAMPLE 1 mRNA and DNA Immobilization with Molecular Hybridization

This example describes, in detail, the immobilization and quantitation of mRNA and DNA from human blood.

Fifteen ml of blood were collected into green-top Vacutainer tubes (containing Heparin as an anticoagulant) to which cyclohexamide and vanadyl nucleosides had been added to give final concentrations of 50 ug/ml and 10 mM, respectively. Red cells were allowed to settle out at 4° C. for 1–3 hours, then tubes were centrifuged at 800×g for 20 minutes. The leukocyte interface (buffy coat) was resuspended in Hank's salt containing 50 ug/ml of cyclohexamide and 10 mM vanadyl nucleosides (HCVX) and mononuclear cells were purified by centrifugation into a Ficoll-Hypaque density gradient (Boyum, A., *Scand. J. Clin. Lab. Invest.* 21 (Suppl. 97):77–89, 1968) for 20 minutes at 18900×g. Granulocytes pellet through Ficoll while mononuclear cells form an interface above the Ficoll. Mononuclear cells were washed with HCVX, pelleted, resuspended in HCVX and counted.

Cell concentration was adjusted to $2 \times 10^7$ cells/ml. For mRNA immobilization Brij-35 was added to 0.5% and mixed with the cells, then DOC was added to 0.5% and the suspension was kept on ice for 5 minutes. Subcellular fractions were prepared by centrifugation at 1400g for 20 minutes at 4° C. The resulting broken cells or subcellular fractions were incubated at 37° C. for 10–60 minutes in 1 mg/ml of self-digested Pronase. An equal volume of supersaturated NaI was added, serial dilutions in to 12.2 molal NaI were made, and aliquots of the solutions were filtered through an NC membrane using Minifold apparatus (Schleicher and Schuell). The NC membrane was moistened with H$_2$O, then soaked for 5 minutes or more in 6×SSC and placed on the Minifold over a sheet of cellulose paper. Solutions were pulled through the NC under vacuum.

For DNA immobilization from the same cells a similar immobilization protocol was used. The cells were subjected to three cycles of freezing and thawing, then were incubated at 37° C. for 10–60 minutes in 1 mg/ml of self-digested Pronase. An equal volume of supersaturated NaI was added, the solution was heated to 100° for 20 minutes, then serial dilutions into 12.2 molal NaI were made, and aliquots of the solution were filtered while hot through an NC membrane using a Minifold apparatus (Schleicher and Schuell). The NC membrane was moistened with H$_2$O, then soaked for 5 minutes or more in 6×SSC and placed on the Minifold over a sheet of cellulose paper. Solutions were pulled through the NC under vacuum.

After filtration, the RNA-membrane was soaked in three changes of H$_2$O then in three changes of 70 ethanol/30 H$_2$O to remove excess NaI; each soak was about 5 minutes at room temperature. Finally, the membrane was soaked for 10 minutes at room temperature in acetic anhydride solution to acetylate basic proteins.

The membrane could be used immediately for molecular hybridization. Filters were sealed in "seal-a-meal" bags with 1 ml/cm$^2$ NC of PR (0.9M NaCl, 0.09M Na Cit, ).2% polyvinylpyrollidone, 0.2% Ficoll, 1% Na dodecyl Sp$_4$, 50 ug/ml of poly(A), 50 ug/ml of low molecular weight DNA and 10 mM vanadyl nucleosides) and shaken overnight at 37° C. PR was removed and replaced with 0.1 ml/cm$^2$ NC of HB (50% formamide, 0.9M NaCl, 0.09M Na Cit, 0.05M Na phosphate, 1% sodium dodecylsulfate (NaDodSO$_4$), pH 7.0) containing 10$^6$ cpm/ml radioactive probe. The sack was resealed and shaken at 42° C. for 17–24 hours in an environmental shaker. After hybridization, the membrane was removed and incubated at 37° C. with shaking with three 30-minute changes of PO (PR containing 0.2% bovine serum albumin). Finally, the RNA-NC was incubated for 15 minutes at 60° C. in 0.1×SSC containing 1% NaDodSO$_4$ and radioautographed at −70° C. using Kodak BB5 film with Dupont Cronex Hi-Speed intensifying screen.

Figure 1:
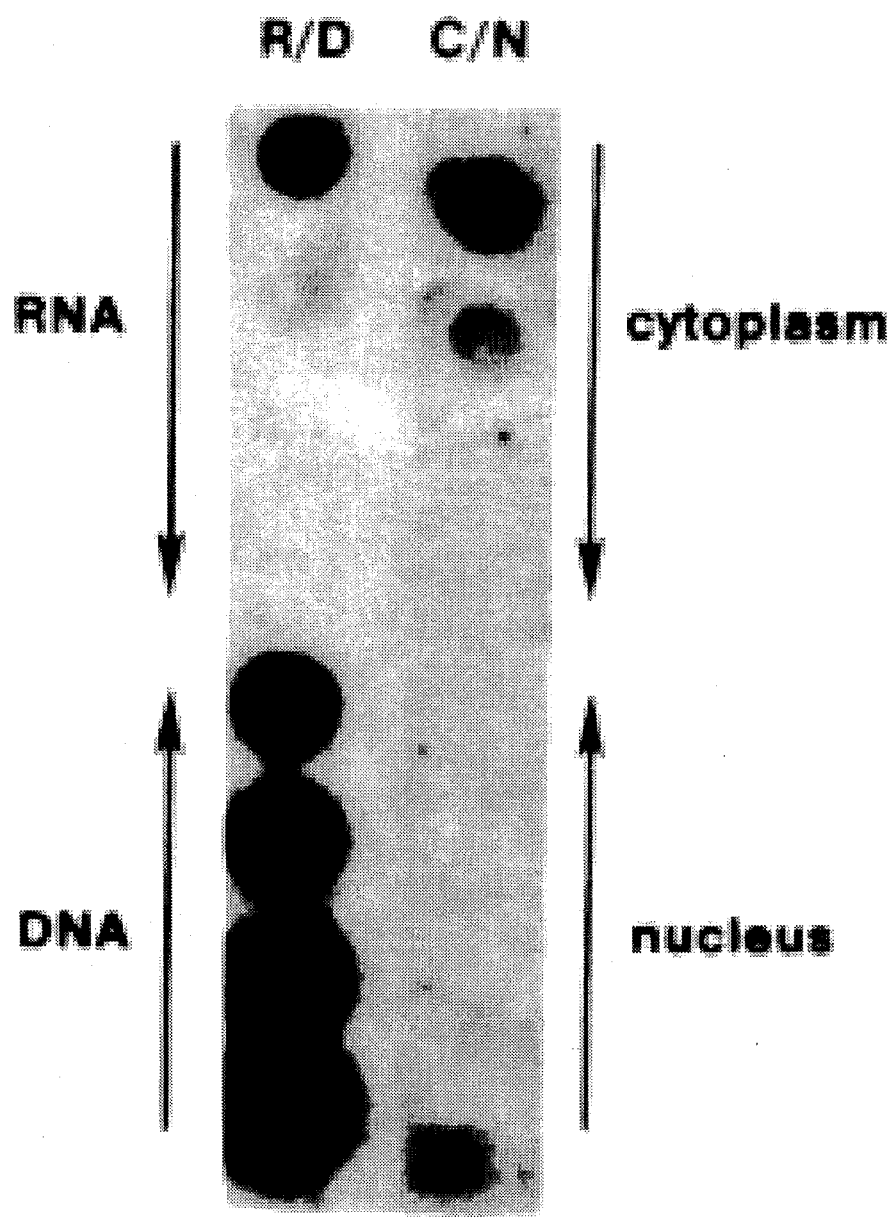
FIG. 1 is a radioautograph showing molecular hybridization of c-myc oncogene probe to mRNA and DNA immobilized from human blood leukocytes.

FIG. 1 presents typical molecular hybridization results from an immobilization experiment. mRNA or DNA have been immobilized from mononuclear cells obtained from blood of a normal human volunteer.

Further referring to FIG. 1 nucleic acids were immobilized as described herein. mRNA and DNA were immobilized from whole cells (R/D row). RNA was immobilized on the top four dots from progressively greater dilutions, top toward middle. DNA was immobilized on the bottom four dots from progressively greater dilutions, bottom toward middle. mRNA was also immobilized from ocytoplasmic and nuclear fractions of the same cells (C/N row). mRNA was immobilized on the top four dots from a cytoplasmic fraction prepared as described in the text. The direction of dilution is top toward middle. mRNA was immobilized on the bottom four dots from a nuclear fraction prepared as described in the text. The direction of dilution is bottom toward middle. Molecular hybridization was carried out with 10$^6$ cpm/ml of nick translated myc oncogene probe at 42° in the 50 formamide system detailed by Bresser et al. (*DNA* 2:243–254, 1983). Radioautography was at −70° for 20 hours with an intensifying screen.

To generate FIG. 1, four undiluted preparations in NaI were prepared:

Standard mRNA immobilization from 10$^7$ whole cells/ml

Standard DNA immobilization from 10$^7$ whole cells/ml

Cytoplasmic mRNA immobilization form the equivalent of 10$^7$ cells/ml

Nuclear mRNA immobilization from the equivalent of 10$^7$ cells/ml

Four-fold dilutions in NaI were prepared from each of these preparations, then 1080 ul aliquots were filtered through NC in the orientations depicted in the legend to FIG. 1. Hybridization to $^{32}$P DNA probes and radioautography were carried out to provide the result depicted in FIG. 1. Results of the R/D row shows expression of the myc oncogene at a level below one molecule per gene, on the average, while the C/N row shows that most of the mRNA transcripts are cytoplasmic. These conclusions assume that immobilized mRNA and DNA hybridize with equal efficiency, which is reasonable under these conditions and that all cells express the myc gene equally, which is probably unreasonable. Nevertheless, mvc gene expression is detectable in the cytoplasm of normal blood cells.

EXAMPLE 2

Data Handling for "Standard Immobilization"

Figure 2:
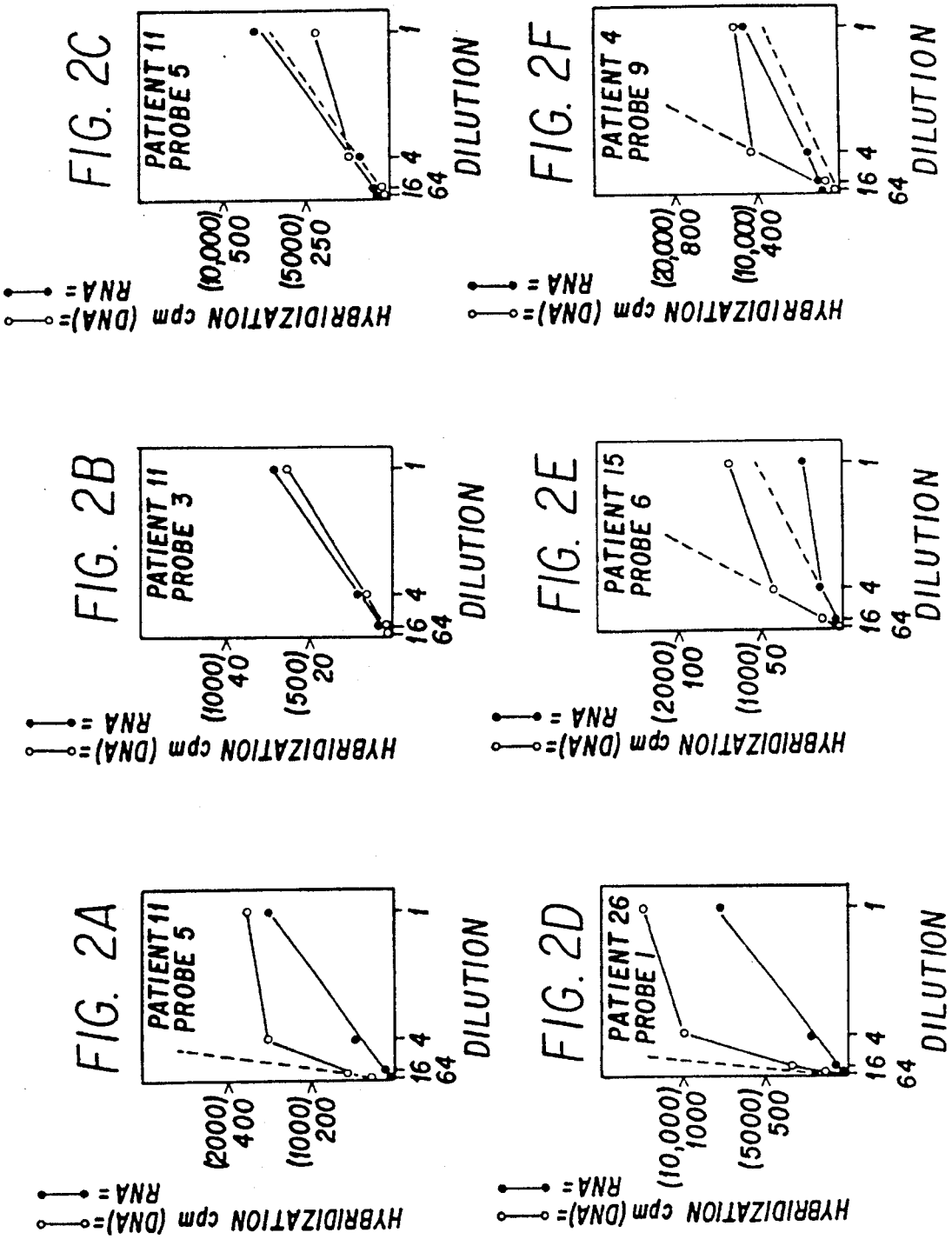
FIGS. 2A–2F are a series of graphs illustrating quantitation of immobilized DNA and mRNA using a DNA reference.

FIG. 2 displays typical results from a large experiment examining expression of some twenty genes in blood cells from leukemia and myeloproliferative disorder patients and normal controls. mRNA and DNA were immobilized from dilutions of mononuclear blood cells, using orientation described for rows R/D of FIG. 1. Twenty-four identical R/D rows were prepared from each cell sample. After filters were prepared, they were thoroughly dried and stored in zip-lock bags in the cold. As probes became available, filters were extracted from the filter bank and analyzed by molecular hybridization and radioautography. Individual dots were then cut and counted by liquid scintillation. Probe radioactivity was plotted versus amount of immobilized material (1=mRNA or DNA from about $5 \times 10^5$ cells). The hybridization signal to mRNA immobilized from a given amount of cells divided by the hybridization signal to DNA immobilized from the same number of cells yielded a mRNA/DNA molecular hybridization parameter, which in theory is the number of mRNA molecules produced per gene.

FIGS. 2A–2F are presented to illustrate the relationship between the number of cells from which mRNA or DNA was immobilized and the resultant molecular hybridization signal. In most cases the relationship was linear, as expected. Deviations from linearity arising from unspecific "background" of probe (FIG. 2F) or coimmobilization of interfering molecules (FIG. 2E) were evaluated. Occasionally, linear relationships were obtained with a proportionality constant below 1. This arose from an excess of immobilized material (insufficient probe). The mRNA/DNA hybridization ratio is a measure of levels of gene expression, using DNA as a reference and assuming genomic stability.

Results like those of FIGS. 2A–2F were used to calculate levels of expression of a variety of genes in human normal and leukemic blood cells, using the mRNA/DNA hybridization parameter. These results showed a 2–10 fold elevation in the expression of several oncogenes and of several highly repeated DNA sequences in leukemia blood cells.

Figure 3:
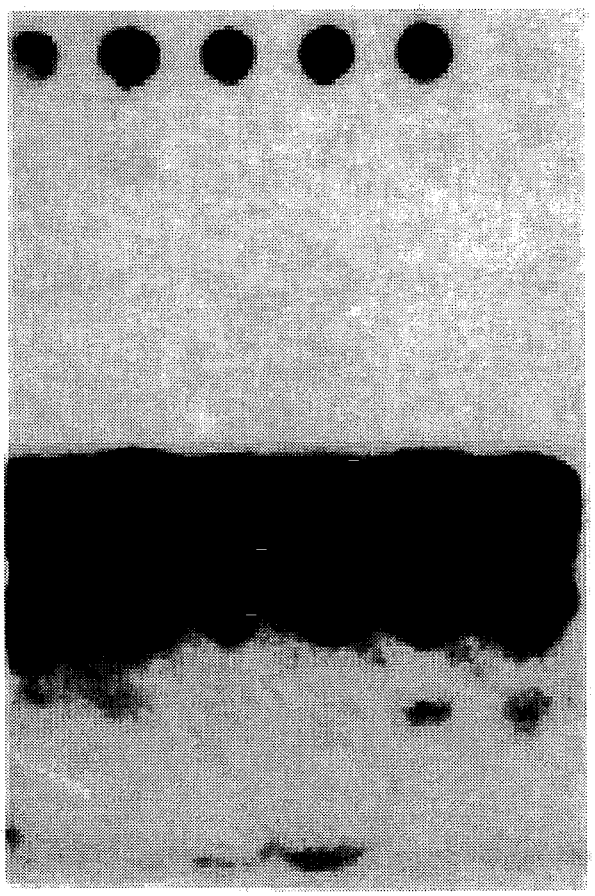
FIG. 3 is a radioautograph showing mRNA quantitation by radioautograph using poly(A) content as a reference.
Figure 4A:
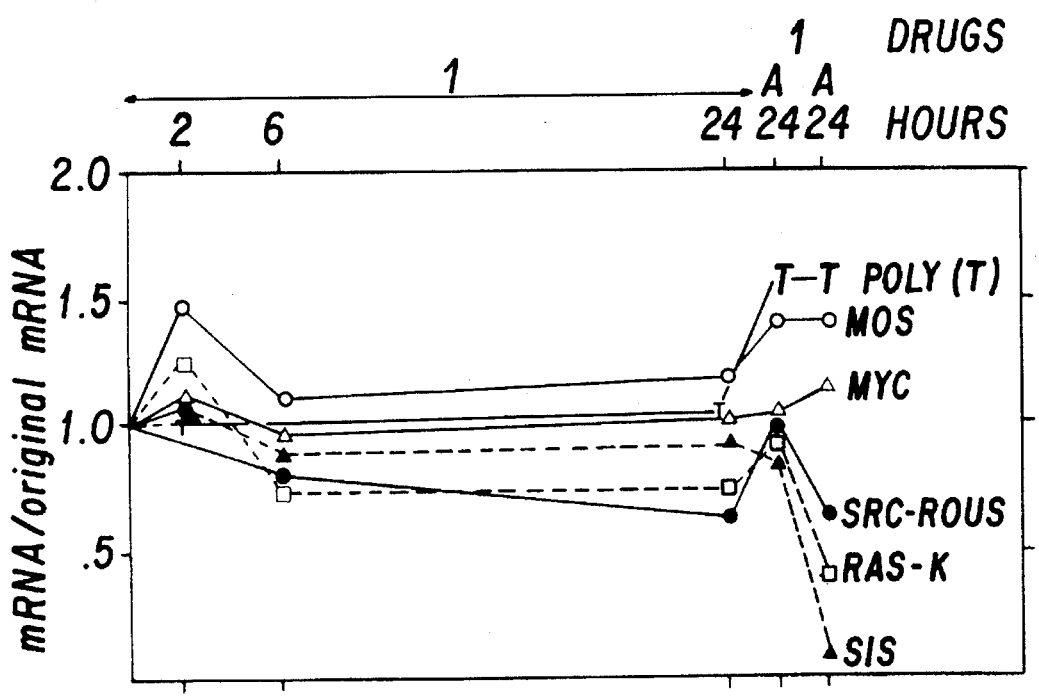
FIGS. 4A and 4B are a graphical illustrations showing mRNA quantitation by scintillation counting using poly(A) content as a reference.
Figure 4B:
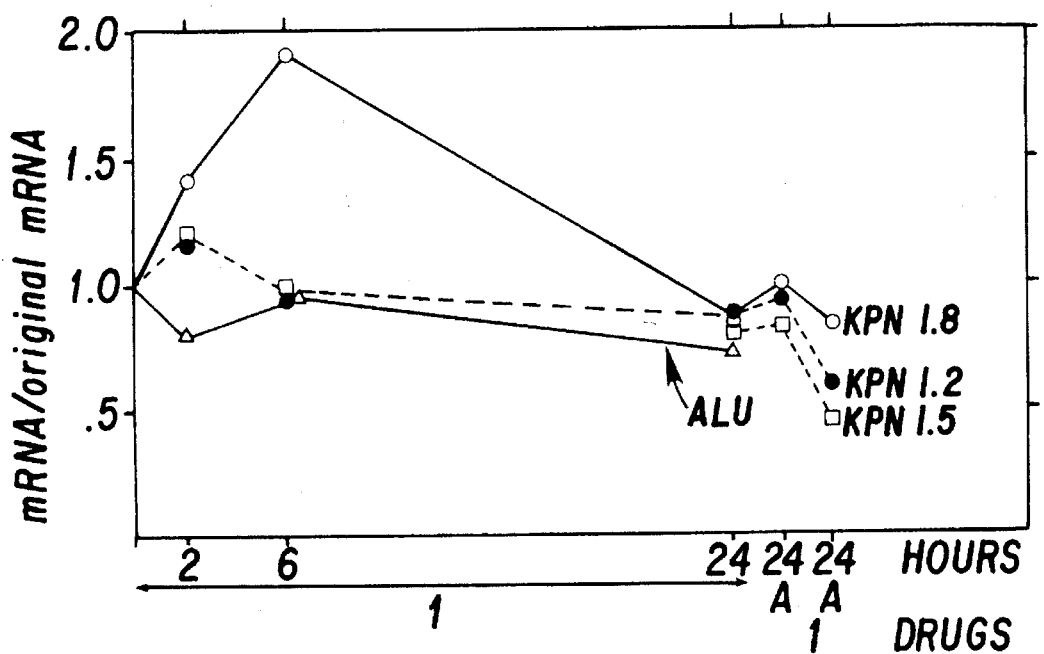

FIGS. 3 and 4A–4B illustrate a change in levels of expression of particular genes in response to drug treatment, using immobilized poly(A) content, the untreated control and other mRNAs as references. RT4 human bladder carcinoma cells were exposed to various drugs for up to 24 hours. mRNA from these cells was immobilized in replicate and probed with various oncoges and with poly(T), the latter a measure of Poly(A) content in the immobilized mRNA. Results were expressed radioautographically (FIG. 3), then individual dots were cut and counted and results were expressed quantitatively (FIGS 4A and 4B).

To arrive at FIG. 3, RT4 human bladder carcinoma cells were grown in the presence of no drug (C), in the presence of drug I for 2, 6, or 24 hours (I2, I6, I24), in the presence of drug A for 24 hours (A24), or in the presence of a combination of drugs I and A for 24 hours (IA24). mRNA was immobilized from $10^6$ cells and from three 4-fold dilutions, arranged in descending order of greater dilution. Sixteen filters were made and were hybridized in 50 formamide for 17 hours with $10^6$ cpm/ml of various probes, including probes corresponding to the sis oncogene (sis), the Ableson leukemia virus oncogene (abl), and Harvey sarcoma virus oncogene (ras-H), the Kirsten sarcoma virus oncogene (ras-K), and Moloney sarcoma virus oncogene (mos), the Rous sarcoma virus oncogene (src), the human myc oncogene (myc), polythymidylic acid (poly T), and three cloned members of the LINES family of human repeated sequences (KIpn 1.8, Kpn 1.5, Kpn 1.2). See Bresser et al. (*DNA* 2:243–254, 1983); *Proc. Natl. Acad. Sci. USA*, in press, 1983) for a description of the probes. Poly T, sis, and src probes were hybridized at 37° the remainder at 42°.

After hybridization, results were displayed radioautographically.

Referring to FIGS. 4A and 4B, after radioautography, the filters from FIG. 3 were cut and counted. The relationship between cell equivalents of mRNA immobilized and hybridization signal was determined and the hybridization signal at a fixed mRNA input was calculated for all samples. Values for drug-treated samples were normalized to the control value. The result from normalization to poly(T) or to an unregulated mRNA yielded the same conclusion, i.e., that sis and ras-K oncogene are regulated by the combination of drugs I and A.

It is obvious from FIGS. 4A and 4B that sis oncogene mRNA is decreased by an exposure to the combination of drugs and that its reduction is not reflective of a general decrease in mRNA content. FIGS. 4A and 4B confirm the qualitative result of FIG. 3 and shows further that ras-K oncogene mRNA is also reduced.

EXAMPLE 3

Detection of Hepatitis Virus DNA or RNA in Platelets, Leukocytes, or Other Blood Products or Other Human Tissues FIG. 5 presents typical results obtained from immobilization tests of virus nucleic acids in human blood platelets. Blood was collected in heparin-containing tubes. The heparinized blood was centrifuged at about 500×g for 20 minutes. The pellet contained leukocytes and erythrycytes which were further purified by centrifugation in Ficoll-Hypague. The supernatant, containing platelets and cell-free plasma, was layered over a 25 to 35% sucrose gradient and centrifuged at about 50,000×g for approximately 17 hours. The top two-thirds of the gradient was collected by centrifugation, resuspended at 1 mg of protein/ml and prepared for immobilization. A variety of methods have been used to prepare blood products. As long as DNA and RNA were not substantially degraded during the preparation, the method of blood fractionation and the purity of cells, cell-free materials, or subcellular extracts was not an important factor in the assay procedure.

Plasma, suspended platelets, suspended cells, subcellular fractions, or nucleic acid-containing components purified therefrom were processed according to the mRNA or DNA immobilizations previously discussed. For mRNA immobilization purified platelets were deproteinized with 200 ul/ml of protease K for 30 minutes at 37°, made 0 5 in Brij 35 and DOC, made saturated with respect to NaI diluted into saturated NaI, and filtered through NC at room temperature. For DNA immobilization plasma or purified platelets were deproteinized with 200 ul/ml of protease KL for 30 minutes at 37°, frozen-thawed three times, made saturated with respect to NaI, incubated at 95° for 20 minutes, and filtered through NC while still hot. Nucleic acid-containing NC filters were soaked in $H_2O$, $EtOH/H_2O$ and dilute acetic anhydride solution as described earlier. Washed filters were incubated with a radioactive hepatitis virus DNA probe under the conditions of molecular hybridization described previously, except that a temperature of 54° C. was employed, and radioautographed to produce the result shown in FIG. 5. Dark areas of exposure indicate a positive hybridization and show the presence of hepatitis virus nucleic acids in the platelet preparation. A variety of other viral probes were used to survey the platelet samples (Table I). Other blood product from the same individual were also analyzed with the same radioactive probes (not shown). It is apparent from the results presented in FIG. 5 and Table 1 (see following page) that a significant number of blood samples are contaminated with the virus and that the present invention can detect the virus contamination.

| Filter |      | HBV |     | mt  |     | poly (I) |     | Herp II |     | VZ  |     |
|--------|------|-----|-----|-----|-----|----------|-----|---------|-----|-----|-----|
| No.    | Dx   | RNA | DNA | RNA | DNA | RNA      | DNA | RNA     | DNA | RNA | DNA |
| 182    | ANNL | 0   | +   | +   | ++  | +        | 0   | +       | +   | 0   | ±   |
| 274    | CML  | ±   | +   | +   | +++ | 0        | 0   | 0       | ±   | 0   | 0   |
| 284    | ET   | 0   | +   |     |     |          |     | 0       | +   | 0   | ±   |
| 291    | CML  | 0   | +   | +   | +++ | ±        | 0   |         |     |     | +   |
| 293    | CML  | 0   | +   | ++  | ++  |          |     | 0       | 0   | 0   | 0   |
| 294    | ET   | 0   | +   | +   | +++ | 0        | ±   | ±       | +   | 0   | 0   |
| 295    | CML  | 0   | +   | +   | +++ | 0        | 0   | 0       | ±   |     |     |
| 296    | CML  | 0   | +   | ±   | +++ | 0        | 0   | 0       | 0   | 0   | 0   |
| 297    | MPD  | 0   | +   | ++  | +++ | 0        | 0   | 0       | ±   | 0   | 0   |
| 70     | normal | 0 | +   | +   | +++ | ++       | ++  | ++      | ++  | +   | +   |
| 67     | normal | 0 | ±   | ++  | ++  | +        | +   | +       | +   | 0   | +   |
| 73     | normal | 0 | ±   | +   | ++  | 0        | 0   | 0       | +   | 0   | 0   |
| 83     | normal | 0 | ±   | 0   | +++ | ++       | ++  | +       | +++ | 0   | +   |
| 85     | normal | 0 | ±   | ±   | +   | +        | +   | ±       | +   | 0   | ±   |
| 272    | CML  | ±   | ±   | +   | +++ | 0        | 0   | 0       | ±   |     |     |
| 288    | ET   | 0   | ±   | +   | ++  | 0        | 0   |         |     | 0   | 0   |
| 68     | normal | 0 | 0   | −   | ++  | +        | +   | ±       | ++  | 0   | ±   |
| 72     | normal | 0 | 0   | +   | ++  | 0        | 0   | ±       | +   | 0   | 0   |
| 76     | normal | 0 | 0   | +   | ++  | +        | 0   | 0       | 0   | 0   | 0   |
| 80     | normal | 0 | 0   | +   | ++  | +        | +   | 0       | ±   | 0   | ±   |
| 90     | normal | 0 | 0   | ±   | ++  |          |     | 0       | 0   | 0   | 0   |
| 96     | normal | 0 | 0   | +   | ++  | +        | +   | 0       | 0   |     |     |
| 275    | CML  | 0   | 0   | ++  | +++ | +        | 0   | 0       | 0   | 0   | 0   |
| 276    | normal | 0 | 0   | +   | +++ | 0        | 0   | 0       | 0   | 0   | 0   |
| 277    | CML  | 0   | 0   | ±   | ++  | 0        | 0   | 0       | +   | 0   | 0   |
| 278    | normal | 0 | 0   | 0   | ++  | 0        | 0   | 0       | 0   | 0   | 0   |
| 279    | CML  | 0   | 0   | ±   | ++  | 0        | 0   | 0       | ±   | 0   | 0   |
| 280    | ET   | 0   | 0   | +   | ++  | 0        | 0   | 0       | ±   | 0   | 0   |
| 287    | CML  | 0   | 0   | +   | +++ | 0        | 0   | 0       | 0   | 0   | 0   |
| others normals | | 0 | 0 | 0 | + | Filters no. 71, 79, 82, 84, 86, 87, 88, 91, 92, 93, 94, 95, 97, 100, 101, 102, 105, 106, 107, 108, | | | | | |
| CML    |      | 0   | 0   | 0   | +   | Filters no. 273, 289 | | | | | |

Other blood products were treated in an identical manner. Platelets or other blood products were also immobilized according to the procedure for "mRNA immobilization from subcellular fractions" with equally positive molecular hybridization results.

This immobilization test has been used to detect viral contamination in samples of blood from the American Red Cross, in fresh blood from leukemia patients and in fresh blood from AIDS/Kaposis sarcoma patients. Contamination was detected by immobilization from samples thought to be virus-free by immunological tests. The present invention can in principle be used to detect contamination of any human, animal, or plant tissue by any virus, bacterium, mold fungus, etc., using the various methods for immobilization of mRNA or DNA previously described, as long as a suitable nucleic acid probe is available. Specific diseases, biological sources and probes which have been tested are listed in Table 2.

TABLE 2

Biological sources from which RNA and DNA have each been immobilized for various diseases and quantitated by molecular hybridization.

| Disease | Biological Source | Probe |
|---------|-------------------|-------|
| 1. Acute lymphatic leukemia | 1. Blood cells | 1. myc oncogene |
|         |                   | 2. abl oncogene |
|         |                   | 3. H-ras oncogene |
|         |                   | 4. K-ras oncogene |
|         |                   | 5. N-ras oncogene |
|         |                   | 6. B-lym-1 oncogene |
|         |                   | 7. sis oncogene |
|         |                   | 8. mos oncogene |
|         |                   | 9. src oncogene |
|         |                   | 10. hepatitis virus DNA (HBV) |
|         |                   | 11. cytomegalo virus DNA |
|         |                   | 12. herpes simplex II virus DNA (HERP II) |
|         |                   | 13. varicella zoster virus DNA (VZ) |
|         |                   | 14. human reverse transcriptase gene |

TABLE 2-continued

Biological sources from which RNA and DNA have each been immobilized for various diseases and quantitated by molecular hybridization.

| Disease | Biological Source | Probe |
|---|---|---|
| | | 15. human ltr mitochondrial DNA (MT) |
| | | 16. Alu repeated DNA |
| | | 17. Kpn repeated DNA |
| | | 18. Xba repeated DNA |
| | 2. blood platelets | 1–18 above |
| | 3. granulocytes | 1–18 above |
| | 4. serum | 1–18 above |
| | 5. cell-free plasma | 1–18 above |
| 2. Acute myelogenous leukemia (ANNL) | 1–5 above | 1–18 above |
| 3. Chronic myelogenous leukemia (CML) | 1–5 above | 1–18 above |
| 4. Polycythemia Vera (MPD) | 1–5 above | 1–18 above |
| 5. Hematologically normal individuals | 1–5 above | 1–18 above |
| 6. Essential thrombocythemia (ET) | 1, 2 and 5 above | 1–18 above |
| 7. Myelofibrosis | 1, 2 | 1–18 above |
| 8. AIDS | 1, 2, 5 | 1–18 above |
| 9. Kaposis cell sarcoma | 1, 2, 5 | 1–18 above |
| 10. Hepatitis | 1, 5 | 1–18 above |
| | 6. whole blood | 10–13 above |
| 11. Renal cancer | 8. tumor | 2, 3, 4, 7, 8, 16, 17 |
| 12. Lymphoma | 9. tumor | 1, 2, 7, 8, 16 |

Note: acronyms are in parentheses

It is expected that variations to be used in this vast and rapidly changing field in the areas of cell collection, cell preparation, subcellular fractionation, molecular hybridization, data display and data handling and we consider all forms of the above areas to be included within the scope of the invention as long as the methods to achieve the above processes are compatible with the immobilization procedure as outlined in the claims. Furthermore, it is expected that modifications in certain aspects of the immobilization procedure itself can be made, for example, in which chaotropic salts or detergents are used, in which methods of cell rupture are used, in which filter supports are used, in which filtering conditions are used, in which wash solutions are used, etc. and these modifications are within the scope of the invention as long as the principles of immobilization discussed herein are retained; namely, the use of a chaotropic salt to simultaneously dissolve nucleic acids in complex mixtures and promote nucleic acid binding to a solid or semisolid support, the controlled use of detergents and filtering conditions (e.g., temperature) to promote selective nucleic acid binding to said solid support and the use of a solid support which will efficiently and selectively retain the nucleic acids with or without subsequent "fixing" steps (e.g., baking and with or without subsequent washing steps).

EXAMPLE 4

Reverse Probing in Chaotropic Salt Solution Using An Immobilized Probe

The term "Reverse Probing" is herein intended to mean a process whereby cells are dissolved directly in a strong solution of a chaotropic salt, heated to denature DNA and destroy DNA or, alternatively not heated, then incubated with a probe-containing membrane under molecular hybridization conditions and under conditions where direct interactions between dissolved nucleic acids and the membrane minimized. This process favors hybridization between the immobilized probe and cellular nucleic acids which are complementary to the immobilized probe. When cells are heated, cellular DNA hybridizes with the immobilized probe; when cells are not heated, cellular RNA hybridizes with the immobilized probe. Reverse Probing utilizes the chemical principles of chaotropic salts which are central to the immobilization process of this invention.

In the foregoing specific embodiments and examples, nucleic acids from cells, viruses, bacteria, etc. were immobilized on a solid support in NaI, then hybridized to a pure radioactive, fluorescent or otherwise tagged probe which was dissolved in an appropriate solution for promoting molecular hybridization. Reverse probing represents a different configuration. In reverse probing, probe can be immobilized onto NC, nylon or another type of membrane, using the present invention or another technique, then hybridization can be carried out by dissolving cells, bacteria, yeast, viruses, etc. or subcellular fractions thereof in a chaotropic salt such as NaI in the presence of additives such as detergents, proteins, oligonucleotides, etc. which reduce direct interaction between DNA or mRNA and the membrane and incubating the resultant mixture with said probe-containing filter. Hybrid formation can be detected by any of several means.

Figure 6A:
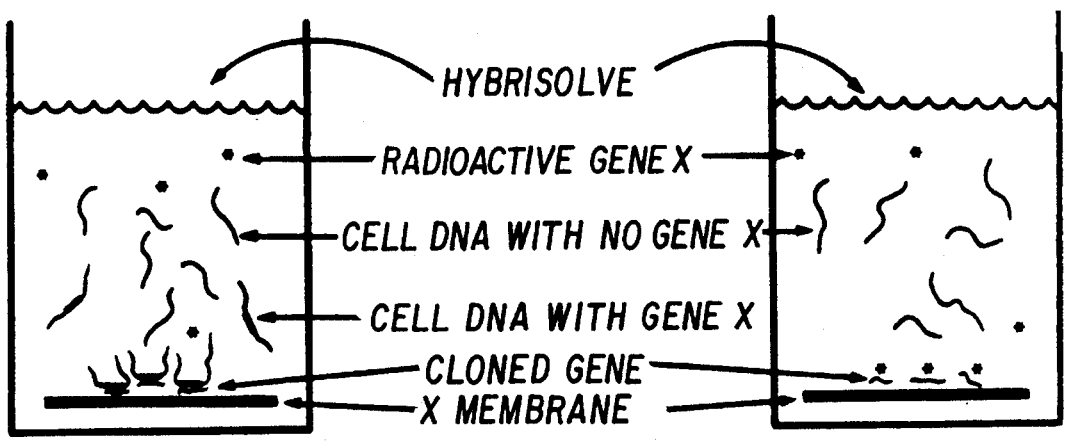
FIGS. 6A and 6B are diagrammatic illustrations schematically showing competitive reverse probing.
Figure 6B:
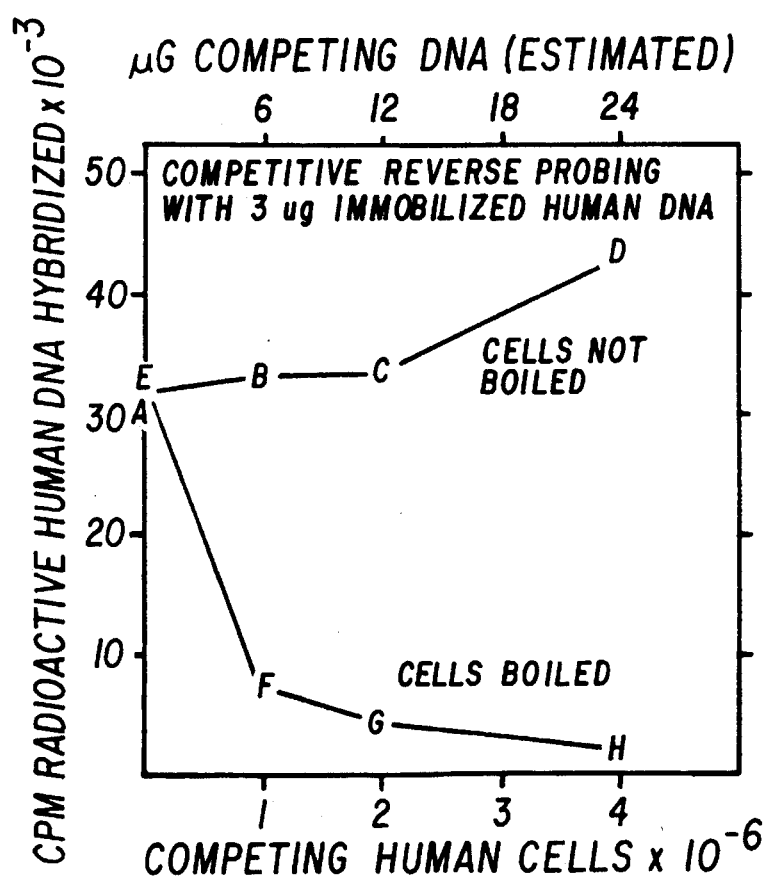
Figure 7:
FIG. 7 is a graphical illustration of the use of competitive reverse probing in measuring DNA sequences in cells.

For example, by including in the solution a tagged probe which is complementary to the immobilized probe, hybrid formation between dissolved cellular DNA, RNA and the tagged or immobilized probe (DNA or RNA) can be measured by reduction (competition) in hybridization between the tagged probe and its immobilized complement (FIGS. 6A and 6B). We call this "Competitive Reverse Probing." FIG. 7 presents an experiment to illustrate this principle, showing measurement of human repeated DNA in $10^6$, $2\times10^6$, or $4\times10^6$ of blood cells. NC membranes containing 3 micrograms of human repeated DNA were prepared by the present invention. A radioactive probe of human repeated DNA was prepared by nick-translation. Mononuclear blood cells were dissolved in NaI containing 1% Brij 58 and then duplicate 1 ml aliquots of NaI/Brij 58 containing 0, $10^6$, $\times10^6$, or $4\times10^6$ cells were prepared. To each aliquot was added $10^6$ cpm of radioactive human DNA (about $10^{-2}$ micrograms). One set of solutions was then boiled for 20 min. to denature DNA. A DNA-containing membrane was added to each solution. Hybridization was effected by incubation for 17 hr at 37°, then reacted nucleic acids were washed away from the filters. The filters were radioautographed then radioactivity was quantitated by scintillation counting. Both results are presented in FIG. 7. It can be seen that in the boiled samples significant competition occurred to the extent that it can be calculated that $10^6$ human cells contains 2–3 micrograms of DNA. Since $10^6$ human cells contains 6 micrograms of DNA of which some 40% is repeated DNA, this result is in excellent agreement with that expected.

Many variation are possible. Specific DNA sequences can be measured by varying the probes. Probes consisting of cloned hepatitis virus DNA permit detection and quantitation of hepatitis virus genomes or mRNA in cells. Immobilization of 1 picogram of probe permits detection of $10^6$ viral genomes. Using other viral probes permits detection of other viral genomes. Eliminating the boiling step and/or preparation of subcellular fractions permits the detection of RNA rather than DNA. In this case, the tagged probe should be single stranded and of the same sequence as the RNA and the probe containing membrane should be pretreated with prehybridization solution. Viral RNAs can be detected and quantitated with this process using viral probes. Cellular RNAs can be detected and quantitated using cloned gene probes such as the myc gene probe (Example 1) but, of course, not limited to that gene probe. DNA or RNA probes can be used. Other membranes that NC can be used as long as 1) probe-membrane complexes can be prepared and 2) hybridization can occur with the immobilized probe in the absence of direct dissolved nucleic-acid membrane interactions during molecular hybridization.

Direct visualization, rather than competitive hybridization is also possible. The experiment described above was repeated, omitting the radioactive probe. Instead of radioautographing the result of molecular hybridization, the membranes were dipped in a solution containing 0.5 ug/ml of ethidium bromide. The filters were then visualized under UV light to detect double stranded nucleic acids on the membrane. No such structures were detected when cells were omitted. Fluorescence was obtained in all cases where cells were boiled, showing directly that hybridization had occurred between the dissolved denatured cellular DNA and the immobilized probe. We call this "Litmus-like Reverse Probing."

All of the variations described above for Competitive Reverse Probing are also possible for Litmuslike Reverse Probing. In addition, many other methods are possible for detecting hybrid structures, including but not limited to, the use of specific antibodies, avidin-biotin complexes, radioactive detection systems, intercalators, etc.

Competitive Reverse Probing and Litmuslike Reverse Probing succeed because of the immobilization principles which are central to this patent application. Chaotropic salts can be used to dissolve cells, denature nucleic acids, prevent nuclease activity and promote specific nucleic acid hybridization. NaI is included in the chaotropic series and is used as the prototype chaotropic salt for the immobilization process. Guanidine thiocyanate has also been used with equal success and presumably other chaotropic salts such as sodium perchlorate, sodium trichloroacetate, sodium trifluoroacetate, etc. will also be useful. Detergents minimize DNA-membrane interactions, a critical aspect of Reverse Probing techniques as it is for the standard immobilization methods (See Specific Embodiment 1c). We expect that other features of the present invention, such as selectivity for mRNA will also contribute to the success of the Reverse Probing variation, for example, when using synthetic RNA probes.

EXAMPLE 5

Applications of the present immobilization technology

Examples 1-4 dealt primarily with the value of immobilization coupled with molecular hybridization in obtaining precise measurements of the quantity of specific mRNA immobilized from a given number of cells. The present invention also lends itself to procedures for determinations of mRNA structure, for cloning copies of mRNA populations in cells as well as for purifying, analyzing and cloning individual mRNA species. The state of the art with these procedures is outlined below.

mRNA Structure #1: Modified S1 Nuclease Assay

Figure 8:
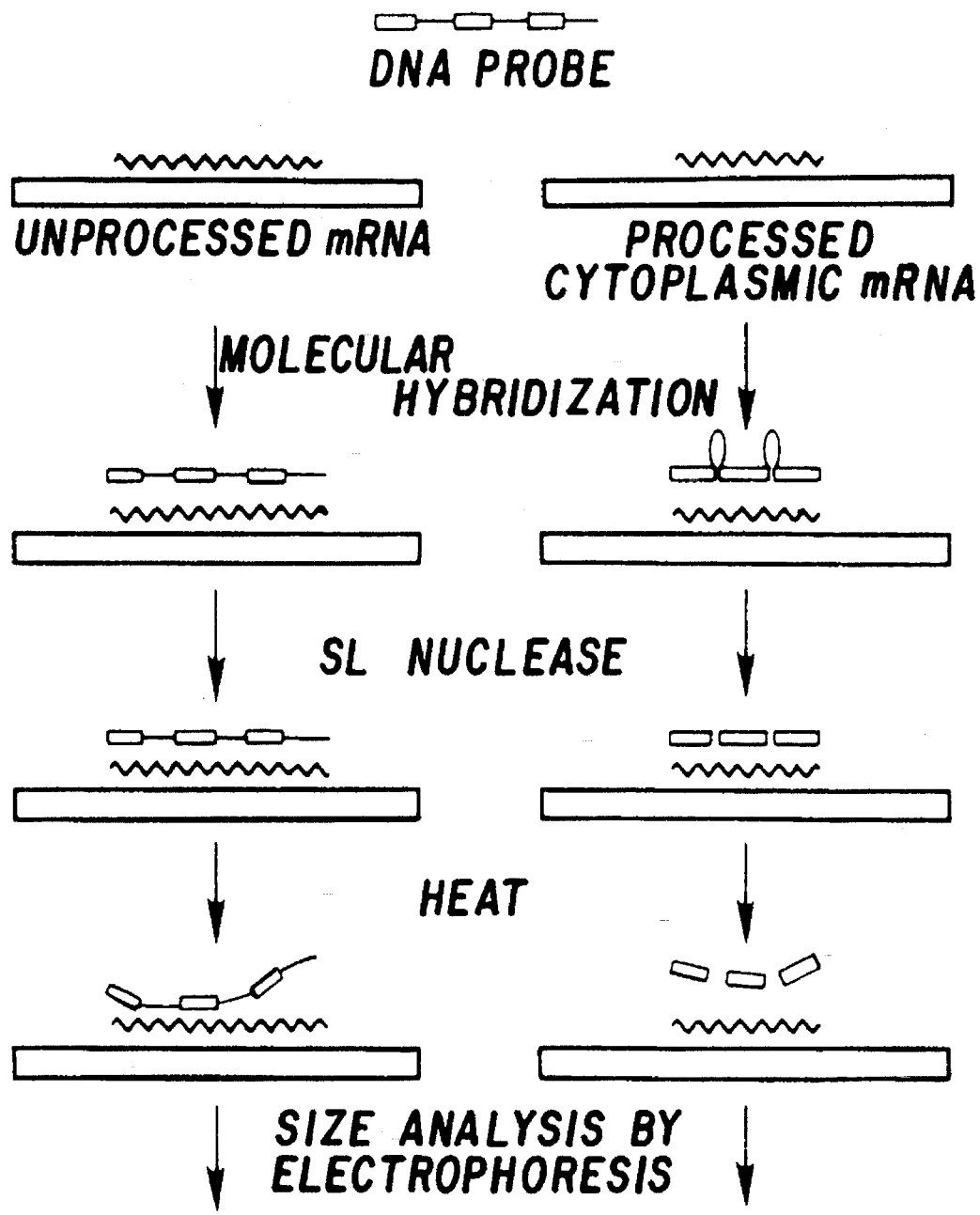
FIG. 8 is a schematic illustration of a process for determining the structure of an immobilized RNA.

The structure of an immobilized mRNA can be determined by measuring the size of the probe which has been hybridized to an immobilized mRNA, digested with S1 nuclease, and released from the filter (FIG. 8). The experiment has been successfully accomplished by hybridizing long single strands of labeled human DNA to immobilized nuclear RNA of leukemic leukocytes, digesting unhybridized probe to nucleotides with S1 nuclease, releasing S1-resistant probe from the filter and analyzing it by electrophoresis into a polyacrylamide gel.

mRNA immobilization and hybridization was carried out as previously described above. The dot containing the DNA-mRNA hybrid was excised and placed in a solution containing 1000 U/ml of S1 nuclease and was incubated at 45° for 5-10 min. In this experiment undigested probe remained on the filter. Undigested probe can be released from the filter if the S1 nuclease contains ribonuclease or when hybrids are formed with immobilized DNA.

After digestion by S1 the filter dot was removed from the solution, rinsed with cold 0.01×SSPE then plunged for 15 sec. in boiling 0.01×SSPE. The released probe was fractionated by electrophoresis into polyacrylamide and results were displayed by radioautography.

There are no apparent pitfalls in this method which are not inherent in the original Berk-Sharp S1 nuclease assay (Berk and Sharp, Cell 12:721-726).

mRNA Structure #2: Modified Northern Transfer

In principle, mRNA can be released from one membrane with pure formamide, fractionated by electrophoresis into polyacrylamide then transferred to another membrane for hybridization with a radioactive probe. In practice, mRNA has been released from NC, has been reverse transcribed and translated (Bresser et al., *Proc. Nat. Acad. Sci.*, 1983) and has been reapplied to NC for molecular hybridization (J. Bresser, unpublished observations), but has not yet been successfully fractionated by electrophoresis into agarose. mRNA has been immobilized and released as described above. The released mRNA has been. fractionated by electrophoresis into polyacrylamide as described (Bresser et al., *Proc. Nat. Acad. Sci.*, 1983), then the gel was radioautographed. In all instances so far examined the mRNA after release from NC exhibited a lower electrophoretic mobility than prior to immobilization. The reason for this is under investigation.

After electrophoresis, mRNA can be transferred to NC either by Thomas' method (*Proc. Nat. Acad. Sci. USA* 77:5201-5205) using NaCl or by using NaI (Bresser et al., *Proc. Nat. Acad. Sci.*, 1983). Less convection occurs using NaCl, producing a sharper image on NC. mRNA transferred in NaI is biologically active and can be reverse transcribed or translated.

Cloning Copies of mRNA Populations in cells

The construction of "mRNA" libraries from defined cell populations has become an important research tool. Since mRNA immobilized from small numbers of cells can be reverse transcribed into full-length cDNA (Bresser et al., *Proc. Nat. Acad. Sci.*, 1983), a rapid cloning procedure is possible. A problem existed in low efficiency of transcription of immobilized mRNA, but the efficiency of reverse transcription has been increased significantly by (I) eliminating the EtOH and acetic anhydride soaks which can be part of the "mRNA immobilization"; (II) eliminating salt during mRNA-filter prewashes; and (III) using $NH^4Ac$ during precipitation. Second strand synthesis on immobilized mRNA has not been proven, but is indicated from the fact that cDNA is released from the filter when Actinomycin D is not included in the synthesis mixture (J. Bresser, unpublished observations).

Cloning of Purified mRNA by Immobilization Technology

Cloning of specific mRNAs from different cells provides a reagent for explaining exactly the differences in the regulation of the relevant mRNAs. The outline for this procedure is:

Fractionate mRNA electrophoretically in polyacrylamide.

Transfer the mRNA to NC in NaI.

Locate the relevant mRNA species by molecular hybridization.

Melt off the hybridized probe.

Reverse transcribe the relevant mRNA.

Clone the cDNA and screen recombinants.

The method is compatible with any method of mRNA purification. Clearly, the simpler the method of mRNA purification the more powerful the overall method will be. Ideally, the mRNA purification outlined above under "mRNA structure #2: Modified Northern Transfer" will yield suitable mRNA populations for this experiment.

The transfer of mRNA from polyacrylamide to NC must be done in NaI (Bresser et al., *Proc. Nat. Acad. Sci.*, in press, 1983) to preserve biological activity. The procedure for this is as follows: Polyacrylamide gels were soaked in saturated NaI for 30–60 min. The gel was overlaid with a sheet of NC which had been soaked in water, then in 1M NaCl, then in saturated NaI. The NC was overlaid with absorbent paper towels. Transfer was allowed to proceed until an amount of NaI solution equivalent to ten times the volume of the gel has passed through the gel. The NC was peeled from the polyacrylamide and soaked in $H_2O$.

Once the total cell mRNA has been transferred to NC the relevant mRNA species can be detected by molecular hybridization. The mRNA-containing band can then be cut precisely from the membrane and the probe can be removed if necessary by dipping the membrane in boiling 0.01× SSPE. Reverse transcription and cloning can follow the procedures outlined in the previous section. Overall, this approach provides an extremely rapid and efficient means of cloning DNA copies of specific mRNAs in instances where mRNA enrichment is useful.

EXAMPLE 6

Immobilizations using various chaotropic salts

K562 cells were washed with Hanks salts containing 50 ug/ml of cyclohexamide and 10 mM vandayl nucleosides and resuspended at $10^7$ cells/ml in the same buffer. Aliquots of 1 ml were distributed in individual Eppendorf centrifuge tubes and centrifuged at 3000 RPM for 10 min. to pellet the cells. Each individual pellet was suspended in a 5M salt solution. The salts used were sodium chloride (NaCl), potassium chloride (KCl), potassium bromide (KBr) (B), potassium acetate (KAc), potassium iodide (KI), (GSCN), guanidine hydrochloride (GH), sodium perchlorate ($NaClO_4$), sodium trifluoroacetate ($NaCF_3COO$) and sodium trichloroacetate ($NaCCl_3COO$). Solutions of NaCl, KCl, KAc, and KBr produced turbid nonviscous cell suspensions. Such turbidity is caused by light scattering from undissolved particles (such as whole cells) in the solutions. Therefore, these salts do not dissolve cells. Solutions of KI, NaI, GSCN, $NaClO_4$, $NaCF_3COO$ and $NaCCl_3COO$ produced clear (nonturbid), slightly viscous solutions representing dissolved cells with freed double-stranded DNA. Heating these solutions to 90°, eliminated the viscosity by denaturing the DNA. Heating the suspensions of 90° caused clumping of cellular material. Thus NaCl, KCl, CAc, GH, and KBr are nonchaotropic salts. The other salts are chaotropic.

One-tenth of one milliliter of each solution was filtered through nitrocellulose and nylon membranes to immobilize DNA. Unheated solutions were filtered at room temperature, 20°–22° Centigrade. Heated solutions were filtered while hot, above 50°. Filtration proceeded slowly or not at all in the cases of nonchaotropic salts, and rapidly in the cases of the chaotropic salts. Membranes were washed three times in 20×SSC (3M NaCl, 0.3M Na Citrate, then were soaked in prehybridization solution and then hybridized using an abl oncogene probe which was radioactive. After hybridization, the membranes were washed, radioautographed, then individual dots were excised and counted as described in Example 5. Immobilizations of DNA from cells heated in solutions of chaotropic salts and of mRNA from cells in unheated solutions of chaotropic salts produced an intense molecular hybridization signal, while attempted mRNA or DNA immobilization from cells in solutions of nonchaotropic salts gave a much less intense hybridization signal. The reason for this low signal with nonchaotropic salts was several-fold: only part of the sample filtered through the membranes before they became clogged, proteins still attached to the DNA or mRNA hindered immobilization (Bresser, J. Doering, G., and Gillespie, D., *DNA* 2:243–254, 1983), proteins coimmobilizing and posthybridization steps (Gillespie, D. and Spiegelman, S., *J. Mol. Biol.* 12:829–842, 1965 compared with Bresser, J., Doering, G. and Gillespie, D., *DNA* 2:243–254, 1983), etc. This experiment shows that salts of the chaotropic series are useful in the present invention's DNA immobilization, while nonchaotropic salts are not.

The experiment was repeated with a 3:2 mixture of the above-mentioned salt solutions and DMSO. The same nonchaotropic-chaotropic differences noted above without DMSO were also seen with DMSO. No differences were seen comparing results obtained with DMSO to those obtained without DMSO, except that DMSO solutions were less viscous.

The experiment was repeated, including 1% Brij 58 in all solutions and avoiding any heating above room temperature. These conditions encourage mRNA immobilization rather than DNA immobilization. Cells suspended in nonchaotropic salts plus Brij 58 remained turbid and nonviscous, probably reflecting intact, undissolved nucleii. Chaotropic salts plus Brij 58 again produced clear, slightly viscous solutions representing dissolved cells with freed, double-stranded DNA. Cells suspended in nonchaotropic salts plus Brij 58 filtered slowly or not at all, while cells dissolved in chaotropic salts filtered rapidly. After hybridization to the radioactive abl probe, mRNA immobilized from cells dissolved in chaotropic salts gave an intense molecular hybridization signal, probably for the reasons cited above for DNA immobilization. This experiment shows that all salts of the chaotropic series suffice mRNA immobilization, while nonchaotropic salts do not.

This experiment was repeated with a 3:2 mixture of the above-mentioned salt solutions and DMSO. The same nonchaotropic-chaotropic differences noted above without DMSO were also seen with DMSO. No differences were seen comparing results obtained without DMSO to those obtained with DMSO, except that DMSO solutions were less viscous.

EXAMPLE 7

Chaotropic behavior of various salts was demonstrated using the definition set forth in "SUMMARY OF THE INVENTION." $2 \times 10^6$ K562 human leukemia cells, at a concentration equivalent to 2 mg/ml, were pelleted from culture medium and suspended in 5% glycerol in water as a control and in various salt solutions. The concentration of each salt was 5 molar. Chaotropic behavior was demonstrated if the cells suspended (or dissolved) in the various salt solutions showed a decrease in optical density (read at 600 millimicrons) by a factor of about 2 relative to that shown by the glycerol/water control. Non-chaotropic behavior is demonstrated by little if any change (or a change in the wrong direction, i.e., toward even higher optical density) in optical density. The results are set forth in Table 3.

TABLE 3

Chaotropicity of Various salts 2 mg cells/ml

| Number | Salt | Optical Density$^{60}$ |
|---|---|---|
| 1 | 5% glycerol in water (control) | 1.26 |
| 2 | culture medium | 1.51 |
| 3 | NaCl | 1.44 |
| 4 | sodium acetate | 1.45 |
| 5 | potassium acetate | 1.46 |
| 6 | potassium bromide | 1.45 |
| 7 | guanidine hydrochloride | 1.42 |
| 8 | NaI | 0.70 |
| 9 | NaClO$_4$ | 0.65 |
| 10 | KI | 0.70 |
| 11 | NaSCN | 0.46 |
| 12 | KSCN | 0.60 |
| 13 | guanidine SCN | 0.47 |
| 14 | sodium trichloroacetate | 0.34 |
| 15 | sodium trifluoracetate | 0.66 |

Based on the above, it will be readily appreciated that culture medium and salts 3–7 are not chaotropic. Salts 8–15 are chaotropic.

EXAMPLE 8

Kit and use thereof for selectively immobilizing mRNA and/or DNA directly from biological source.

A kit containing a vial of 10% Brij 35 in water, a vial of aqueous 10% sodium desoxycholate, a vial of 7 ml supersaturated NaI, a vial of 7 ml saturated NaI containing 1% Brij 58, and a vial of 7 ml saturated NaI was given to a laboratory technician, along with a culture of K562 human leukemia cells in order to detect the presence of DNA and mRNA sequences corresponding to a specific gene, the abl oncogene. K562 cells reportedly contain this gene and express it (Collins and Groudine, PNAS 80:4813–4817, 1983). The technician harvested K562 cells, suspended them at $10^7$ cells/ml in Hank's salts containing 50 ug/ml of cyclohexamide and 10mM vanadyl nucleosides, prepared 90 ul aliquots and treated the cells according to the above protocol for immobilizing mRNA or DNA. Four four-fold dilutions of dissolved cells were prepared in saturated NaI. The membranes were then soaked as indicated in the protocol set forth in the Detailed Discussion. The membranes were then soaked in the prehybridization solution described in this invention and hybridized with a $^{32}$P-labeled abl probe (pBR322 plasmid containing the Bgl Ii fragment of the lambda AM-1 clone of Abelson murine leukemia virus DNA labeled to about $10^8$ cpm/ug of DNA. Hybridization was in 5 ml of 50% formamide, 3×SSC, 0.1% SDS and 0.05M NaPO$_4$, pH 7.0, and radioautographed for 24 hr. at −70° with an intensifying screen. Under the conditions employed hybridization was seen with DNA immobilized from four dilutions of cells, corresponding to $4 \times 10^5$, $1 \times 10^5$, $2.5 \times 10^4$ and $6 \times 10^3$ cells per filtration while hybridization with mRNA was observed with the two largest numbers of cells used. Using longer times of hybridization or more labeled probe or longer radioautography times would have increased the sensitivity of the experiment and decreased the number of cells necessary to visualize a hybridization signal.

EXAMPLE 9

This example demonstrates the minimum steps needed to immobilize mRNA or DNA from a biological source—dissolution in a chaotropic salt solution followed by filtration through an immobilizing membrane.

Blood (5 cc) was collected from a normal donor and a small amount of heparin (less than one milligram) was added to prevent coagulation. Separately, 0.2 ml of 5 Molar salt solution was added to each of two series of test tubes and 0.05 ml of blood was added to each tube. One series of test tubes was used to test sodium chloride solution. One series of test tubes was used to test a known chaotropic salt, guanidine thiocyanate. Viscosity and turbity were then measured on each tube. To tubes to be used for evaluating DNA immobilization, $^{32}$P-labelled DNA was added. To tubes to be used for evaluating mRNA immobilization, $^{32}$P-labelled mRNA was added. The tubes to be used to determine DNA immobilization were heated to 90° C. for 20 minutes, and their viscosity and turbidity were then again determined. Each tube (sample) was then filtered through separate nitrocellulose membranes and the radioactivity of each membrane was then recorded with a Geiger counter. (See Table 4.)

TABLE 4

| Salt | Radioactivity (Milli Roentgens) |
|---|---|
| NaCl, heated (DNA evaluation) | less than 2 |
| NaCl, unheated (mRNA evaluation) | less than 2 |
| guanidinium SCN, heated (DNA Eval) | greater than 6 |
| guanidinium SCN, unheated (mRNA eval) | greater than 6 |
| Control $^{32}$P-labelled mRNA | greater than 6 |

Using sodium chloride, all (unheated) tubes remained turbid and relatively non-viscous, indicating that little if any dissolution had taken place. When sodium chloride tubes were heated, a precipitate formed. When sodium chloride tube contents were filtered, a pile of debris collected on the filter. The debris was washed off the filter prior to measuring filter radioactivity.

Using guanidine thiocyanate to dissolve blood, each tube solution was clear, though the solutions were tinged green. The solutions were relatively non-viscous. On heating, no precipitate formed. Filtration rates were reasonably rapid.

The Geiger counter readings indicated that at least three times as much nucleic acid of interest was immobilized from quanidine thiocyanate solutions as from sodium chloride solutions.

As control, $^{32}$P-labeled mRNA or DNA, in an amount equivalent to the amount added to each blood sample, was pipetted into 10% trichloracetic acid and filtered through NC. The Geiger counter reading was equivalent to that for the spiked blood samples, indicating the mRNA and DNA immobilization is quantitative.

EXAMPLE 10

An Experiment was Conducted to Determine the Speed and Sensitivity of the Invention in Detecting Target DNA Sequences. Target DNA SP64 plasmid DNA linearized with Eco R1, was diluted into 5M GuSCN/0.1M EDTA pH 7.0. Aliquots of 10 ul of the DNA dilutions were prepared in duplicate in 500 ul Eppendorf tubes. The tubes were capped, heated to 60° for 5 min., cooled to room temperature and mixed with 5 ul of an RNA probe dissolved in 2×SSC.

RNA Probe Preparation

The RNA probe was synthesized on supercoiled SP64 DNA, using SP6 RNA polymerase as specified by the manufacturer, promega Biotech. One microgram of DNA and 30 units of RNA polymerase were incubated for 1 hr. at 37° C. in 50 ul of a solution specified by Promega Biotech plus nucleoside triphosphates as follows: 500 uMATP, CTP and UTP plus 5 uM GTP and 200 uC $^{32}$P GTP (3000 C/m mol). After incubation at 37° DNAase 1 (3 Units from Promega Biotech) was added and incubation was continued at 37° C. for 15 min. Diethyloxydiformate (5 ul; Eastman Chemical; also known as diethylpyrocarbonate) was added and the emulsion was vigorously agitated for 5 sec. The volume was adjusted to 200 ul with TE buffer and unreacted nucleotides were removed by spun chromatography through Sephadex G50 as outlined by Maniatis et al., *Molecular Cloning*, published by Cold Spring Harbor (1982). The flow-through was made 0.4M in NaCl, heated 20 min to 100° and filtered through 2 layers of nitrocellulose (BA85, Schleicher and Schuell). The filtrate was diluted to $10^6$ cpm/ul with 2×SSC and stored at −20°. For long-term storage the probe was precipitated from 2 vols of ethanol, collected by centrifugation at 12,000×g for 15 min, dissolved in 100% formamide and kept at −20°. The probe was diluted fivefold in 2×SSC before use (concentration=2·$10^5$ dpm/ul; ca. 2 ng/ul or 5 ng/hybridization reaction). The probe represented 600 nt of the 3,000 nt SP64 DNA.

Molecular Hybridization

Immediately after the probe was added, the solution was transferred to a 37° bath and held there for 2 hr to allow molecular hybridization between the RNA probe and the SP64 target DNA.

Hybrid Detection

After hybridization, 200 ul of 2×SSC/0.1M EDTA ph7/50 ug per ml of polyadenylic acid were mixed in and the resultant solution was filtered through nitrocellulose (BA85, Schleicher and Schuell) at a rate of about 1 ml/min. The nitrocellulose had been wet in $H_2O$ and soaked briefly in 2×SSC prior to filtration. The bulk of unreacted RNA probe flowed through the membrane while DNA and associated RNA probe became membrane-bound.

After filtration the membrane was soaked for 30 min at 55° in 50 ml of 2×SSC/20 ug per ml of ribonuclease A/20 units per ml of ribonuclease T1. This step removes adventitiously bound probe, leaving only hybridized probe associated with the membrane. Radioactivity on the membrane was estimated by radioautography with x-ray film (FIG. 9A), and quantified by scintillation counting (FIG. 9B).

As FIGS. 9A–9D show, the amount of RNA probe associated with the membrane was a direct function of the amount of target DNA. The smallest amount of DNA giving an increased radioactivity signal ("positive hybridization") in this experiment was 0.3 picograms of DNA. This corresponds to the detection of about 300,000 gene-size DNA molecules (ca. 1000 nucleotides long), in a 3 hr assay. These speed and sensitivity parameters are within the requirements of most situations where gene diagnosis will be initially used. Since the probe only comprised ⅕ the complexity (length) of the target and since only one of the two target strands is detected, 0.03 pg (30 fentograms) of complementary target sequence was measured in this experiment).

Figure 9A:
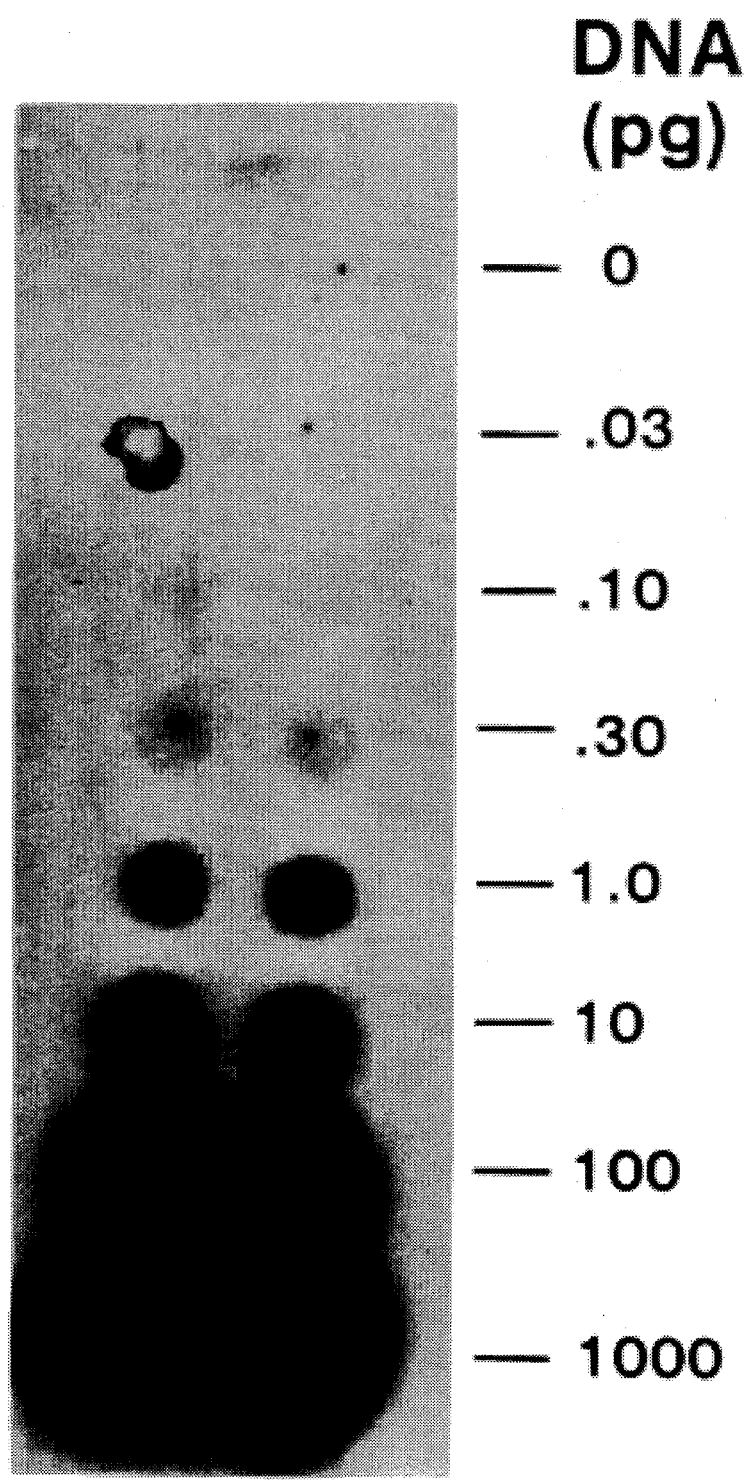
FIGS. 9A–9D represent illustrations of the sensitivity of the invention under various conditions.
Figure 9B:
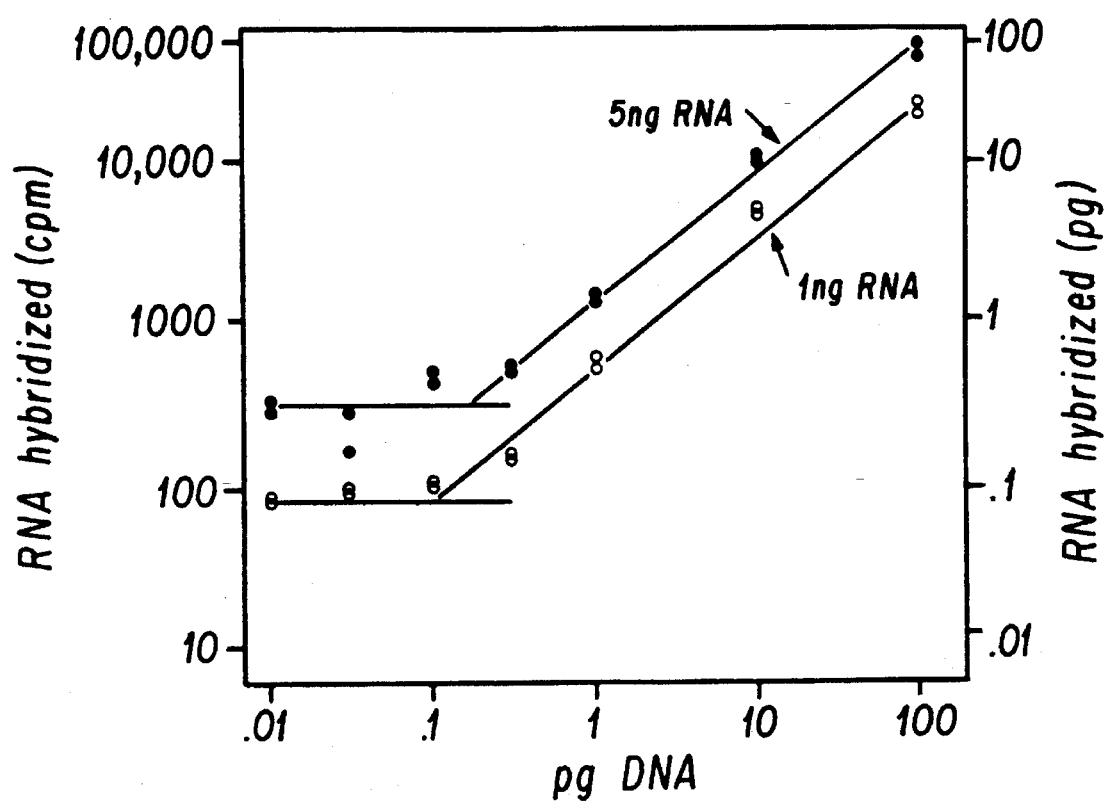

FIG. 9B is a quantitative represented of results like those illustrated in FIG. 9A. Note that with 5 ng of probe, the quantity of probe hybridized equals exactly the quantity of complementary target DNA present; that is, hybridization is 100% efficient with regard to saturating target sites.

The experiment was repeated in a setting more comparable to gene diagnosis. Cells were first dissolved in 5M GuSCN/0.1M EDTA ph 7.0 at a rate of $10^7$ cells/ml. This was done as follows: Five milliliters of blood were drawn into tubes containing heparin. Mononuclear cells were prepared by centrifugation into Ficoll-Hypaque using methods which are standard in the art. The mononuclear cells were diluted with PBS, counted in a hemocytometer, pelleted by centrifugation and 1 ml of 5·M GuSCN/0.1M EDTA ph 7.0 was added for each $10^7$ cells pelleted. The cells substantially dissolved after 1–2 min of gentle agitation.

Figures 9C, 9D:
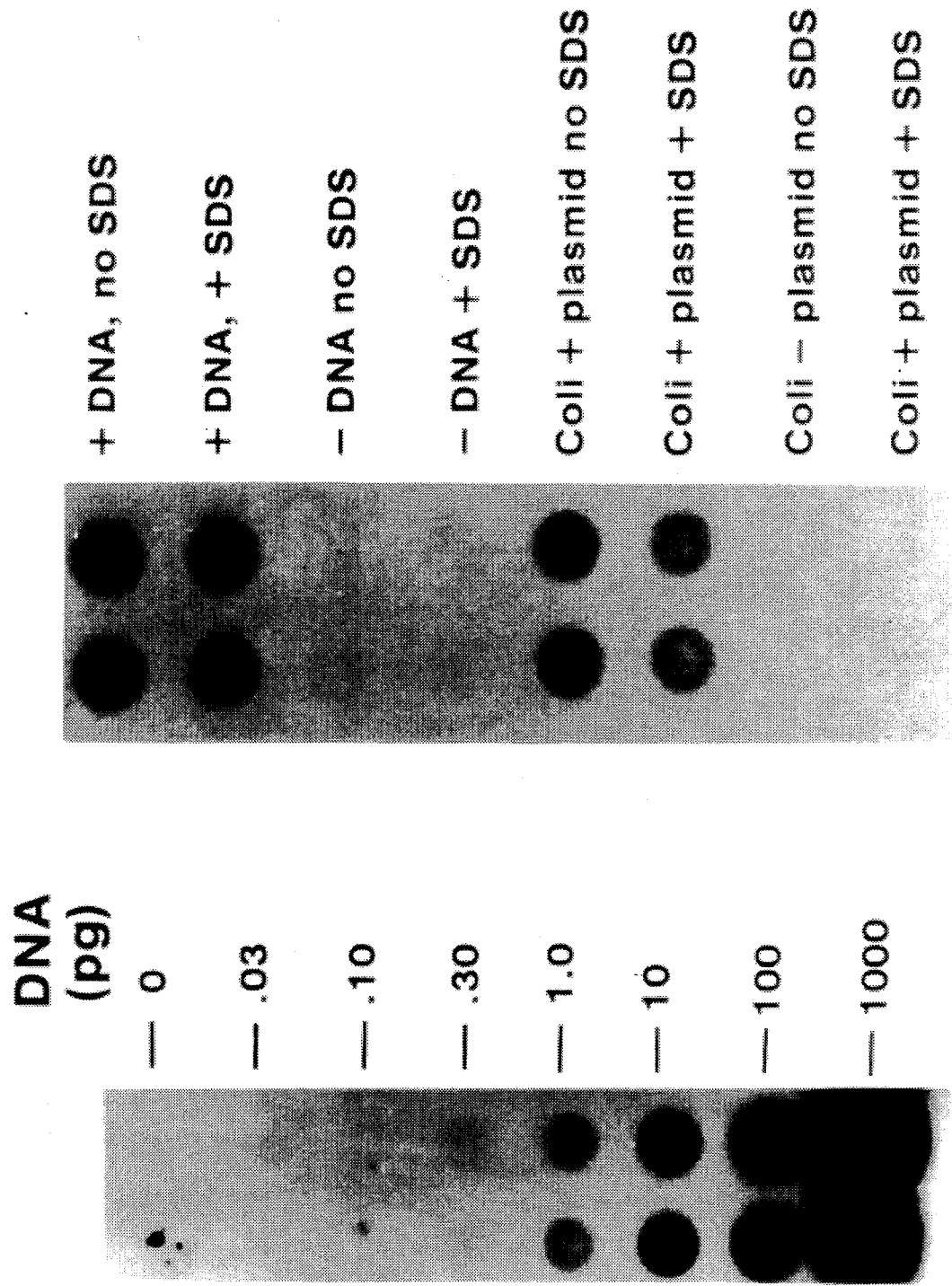

SP64 plasmid DNA linearized with Eco R1 was diluted into the solution of dissolved cells. Aliquots of 10 ul the DNA dilutions were prepared in duplicate in 500 ul Eppendorf tubes. The tubes were capped, heated to 60° for 5 min, cooled to room temperature and immediately mixed with 5 ul of the RNA probe described above Incubation at 37°, dilution into 2×SSC/0.1M EDTA pH7.0/50 ug per ml of polyadenylic acid, filtration, nuclease treatment, filming and scintillation counting were performed as described above. As can be seen in FIG. 9C, substantially the same sensitivity of target DNA quantitation was achieved in the presence of dissolved cells as in their absence. This result established that the present invention can be successfully used for gene diagnosis on a clinical sample.

The experiment was repeated to learn whether the invention could be used on a body fluid, rather than a single-cell suspension. First, a solution of 7M GuSCN/0.14M EDTA was prepared by mixing 16.6 gms of solid GuSCN (Flukka Chemicals.) with 5.6 ml of 0.5M EDTA. The volume was adjusted to 25 ml and solids were dissolved by gentle heating. One-half milliliter aliquots were dispensed while the solution was warm. The solution solidified upon cooling to room temperature.

Two-tenths of a milliliter of whole, heparinized blood were added to one 0.5 aliquot of 7 MGuSCN/0.14M EDTA and the system was gently shaken at room temperature until solids were substantially dissolved, typically 1–2 min.

SP64 plasmid DNA linearized with Eco R1 was diluted into the solution of dissolved blood and probed as described above, except that 1) the probe was prepared in 5M GuSCN so that the system was maintained at 5M GuSCN during hybridization, 2) hybridization was done at 23° and 3) hybrids were diluted into 200 ul of 2×SSC/0.1M EDTA, pH 7/50 ug/ml of polyadenylic acid and filtered through BA85 NC as above. Substantially the same sensitivity of target DNA quantitation was achieved in the presence of dissolved blood with dissolved cells or pure GuSCN/EDTA solution.

The experiment was repeated to learn whether the invention could be used on a solid tissue. A biopsy of lung cancer was obtained as a leftover piece from a pathology study. The tissue specimen was weighed and then was laid upon a stainless steel box filled with liquid nitrogen. After the tissue had frozen, it was pulverized with a pestle cooled in liquid nitrogen. The powder was transferred into a tube and 5M GuSCN/0.1M EDTA pH7 was added at a rate of 1 ml per 10 mg of powder. After gentle agitation for 1–2 min the powder was substantially dissolved.

SP64 DNA linearized with Eco R1 was diluted into the solution of dissolved tissue and probed as described for 5M GuSCN lacking tissue. Substantially the same sensitivity of target DNA quantitation was achieved in the presence of dissolved tissue as with dissolved blood or dissolved cells or with pure GuSCN/EDTA solution (data not shown).

The experiment was repeated to learn whether the invention could be used on intact bacteria. *E. coli* carrying the SP64 plasmid was incubated with 2 mg/ml of lysozyme at 25° for 5 minutes, then was made 5M GuSCN/0.1M EDTA as described above for whole blood and heated 5 minutes at 60°. Hybrids were formed in 15 ul 3M GuSCN/0.06M EDTA with 10 mg of RNA probe. Hybridization was for 5 minutes at 25°. Results were determined radioautographically (FIG. 9D) and by scintillation counting. The sensitivity of detection of intracellular plasmid was compared with that of an equivalent amount of purified, linearized DNA. the detection of intracellular plasmid (2569 cpm hybridized) was about half as efficient as the detection of purified DNA (5177 cpm hybridized). The inefficiency probably resulted from incomplete hybrid capture on nitrocellulose, since other detection methods, using oligodeoxynucleotide probes have consistently shown measurements of intracellular plasmid to be 90–115% as effective as marked DNA detection (M. Collins, personal communication). SDS was included in some samples to aid bacterial lysis but was found to be unnecessary and, in fact, hindered hybrid immobilization. Incubation at 105° can be used in place of the lysozyme pretreatment.

The above experiment illustrates the speed with which the invention can be employed. This speed is also illustrated by the experiment described below.

The experiment was repeated to learn whether the invention could be used on intact cells to measure HIV virus RNA. One hundred thousand infected or uninfected lymphocytes were dissolved in 10 ul of 5M GuSCN/0.1M EDTA/1M NaCl and heated to 60° C. for 5 minutes. Hybridization of the dissolved cells with 10 ng of an RNA probe corresponding to the PstI-EcoRi gagpol fragment of HIV virus was conducted in 12.5 ul of 4M GuSCN/0.08M EDTA/0.8M NaCl for 5 minutes at 25°C. Hybridization was quantitated by scintillation counting. Results were as follows: Culture C (Infected)=5555 cpm hybridized, Culture D (infected)=3585 cpm hybridized, Culture E (uninfected)= 1031 cpm hybridized and Culture F (uninfected)=1044 cpm hybridized. Since other experiments showed the reaction to be kinetically complete, since the probe had a specific activity of $10^3$ cpm/pg and since the complexity of the target was 1500 nucleotides, the result shows an average of 13 copies per cell of virus genes in culture C and 7.5 copies per cell of virus genes in culture D. Thus, this experiment illustrates the speed, simplicity and quantitative nature of the invention.

Overall, this Example illustrates several advantageous features of the invention. In addition to speed, simplicity and quantitation as mentioned above, the experiments of this Example demonstrate the versatility of the invention when employed on a wide variety of clinical samples.

It will moreover be obvious to those skilled in the art that the relatively small number of manipulations and the mild temperatures employed mean that the invention is well suited to automation.

All of these features combine synergistically to provide a clinical applicability not anticipated in the prior art.

It should be noted that the practice of the invention is independent of the nature of the probe and the means of hybrid detection. For example, probes complementary to a different fragment of the viral genome may be used. Further, double-stranded probes or oligonucleotide probes have been used instead of single-stranded probes with similar or equal efficacy. Probes labeled with biotin have been used, and others labeled with enzymes, metals or antigens might have been used instead of a radioactive probe. Photon emission resulting from an energy transfer process or some other method might have been used instead of filtration to measure the extent of hybridization. The essence of the invention with respect to this Example 10 is the efficient solubilization of DNA from a biological sample and its denaturation essentially immediately permitting its hybridization with a DNA or RNA probe.

EXAMPLE 11

An experiment was conducted to show the efficiency of liquid-liquid hybridization in GuSCN, NaI and formamide.

An RNA probe was prepared as described in Example 10. Twenty-five pg of RNA probe was hybridized with linearized, denatured SP64 DNA (see Example 10) in 15 ul of hybridization solution. 1 Hybridization solutions consisted of various concentrations of GuSCN or NaI in $H_2O$ (2M, 3M, 4M or 5M) or 50% formamide, 0.9 m NaCl/0.09M NaCitrate/0.014M NaPhosphate, pH 6.8. Hybridization was conducted for 2 hours at 25°, 37°, 45° or 55°.

To measure hybridization with target DNA excess, RNA-DNA hybrids formed in 15 ul with 200 ng of DNA target were filtered as described in Example 10 through nitrocellulose and radioautographed. In 5M GuSCN lacking EDTA, in 2–3m NaI or in 50% formamide/0.9M NaCl hybridization of a trace of RNA probe (25 pg/15 ul) to an excess of DNA target (200 ng/15 ul) proceeded efficiently, under optimal conditions converting 90% of RNA chains to RNA-DNA hybrid structures. Routinely, 40–50% of input radioactivity could be converted to hybrids which resisted RNAase treatment in 0.3M NaCl at 23°.

In experiments with only a modest excess of target DNA (10 ng in 15 ul) the extent of hybridization of 25 pg of RNA probe proceeded less efficiently in 2 hours at suboptimal conditions, but at the $T_{opt}$ in 3–5M GuSCN over 90% of probe RNA chains were captured in hybrid complexes with DNA (FIG. 10A). The hybridization efficiency in GuSCN was 50–100 times that observed in 50% formamide/0.9M NaCl at 42° C. in parallel experiments (FIG. 10B). Hybridizations in concentrated NaI proceeded inefficiently (FIG. 10C).

Optimal conditions varied with varying GuSCN concentration (FIG. 10B) lower optimal temperatures were correlated with higher GuSCN concentrations as expected. The temperature optimum in 3M GuSCN was over 55° while in 5M GuSCN the $T_{opt}$ was around 37°. Nevertheless, even with low quantities of probe, the hybridization reaction approached completion in 2 hours over a wide range of conditions (FIG. 10B).

EXAMPLE 12

Experiments were conducted to determine the speed of molecular hybridization in GuSCN An RNA probe was prepared as described in Example 10. RNA probe was hybridized with linearized, denatured SP64 DNA (see Example 10) in 15 ul of hybridization solution. Hybridization solution consisted of various concentrations of GuSCN in 0.1M EDTA, pH 7.0. Hybridizations were conducted at various temperatures for various lengths of time.

Based on direct comparisons with hybrids formed at 37° in 50% formamide in probe excess (e.g., Example 11), hybridization in GuSCN was accelerated some 100-fold. Similarly rapid kinetics were obtained at lower probe concentrations (FIGS. 11A and 11B). Using 1.3 ng/ml of probe, and 0.25 ng/ml of complementary target DNA hybridizations in 3 or 4M GuSCN were essentially over in 5–10 hours. The time of half-completion was about 3 hours, corresponding to a $C_ot_{1/2}$ of 0.03×10 instead of the $2×10^{-3}$ expected for nucleic acids of complexity 1 kb. This amounts to a 70-fold calculated acceleration over Britten and Kohne standard conditions (Science 161:529, 1968). No further acceleration was obtained with 1M NaCl. The hybridization rate was essentially constant at 23° over a wide range of GuSCN concentrations (FIG. 11C).

High concentrations of chaotropes during hybridization lower the hybridization $T_{opt}$ and accelerate the hybridization reaction. $T_{opt}$ values will probably vary with each chaotrope as specified by Hamaguchi and Geiduschek (*J. Am. Chem. Soc.* 84:1329, 1962). In practice, GuSCN was preferred over NaI because the hybridization efficiency with GuSCN was always superior and because the hybridization rate accelerations were greater.

RNA-DNA hybridizations can be performed at room temperature in 3–6M GuSCN. The $t_{1/2}$ for hybridizations using nanograms of RNA and complementary target DNA per milliliter is about 4 hours. Hybridizations driven with 100 ng of probe per milliliter are 75% or more complete in 5 minutes at room temperature.

EXAMPLE 13

Use of the invention for virus DNA Diagnosis on Whole Blood Samples

Blood was collected into evacuated tubes containing heparin from two individuals with active hepatitis and hepatitis B virus DNA sequences in mononuclear cells as well as from two normal, virus-free volunteers. Five microliters of whole unclotted blood were mixed in a conical-bottom 0.5 ml plastic tube with five microliters of liquified supersaturated NaI. Five microliters of a solution containing 10 ng tricine, pH 7, 0/0.1 mM dithiothreitol and 100 ng of a single-stranded, $^{32}$P-labeled, RNA probe consisting of the whole Hepatitis B virus genome was added and the solution was thoroughly mixed. The probe was prepared as specified in Example 10 but using a recombinant SP64 DNA template into which had been cloned the whole Hepatitis B virus genome. The solution was incubated at 90° for 5 minutes to denature sample DNA. Some tubes were transferred to a 37° water bath and incubated there for 4 hrs to permit molecular hybridization. After hybridization, the solution was expelled into a tube containing 350 microliters of 2×SSC/0.1M EDTA/50 ug/ml of poly (A). Hybridized probe molecules were trapped on a nitrocellulose membrane by filtration under mild vacuum (see Example 10). Some membranes were incubated for 30 min at 37° in 0.4M NaCl/0.05M tris, pH 7.2/20 g per ml RNAase A to destroy residual, unhybridized RNA probe. All membranes were soaked for 15 min in 0.4M NaCl/0.05M tris, pH 7 at room temperature. The extent of hybridization was assessed by radioautography using x-ray film and quantitated by analyzing radioactivity on the membrane in a scintillation counter using conventional techniques. As can be seen in Table 5 a greater hybridization signal was obtained with blood from individuals with hepatitis, compared to the unafflicted controls, as long as the 4 hr incubation to promote molecular hybridization was included.

TABLE 5

| Source of Blood | no INC 37° | | 4 hr 37° | |
|---|---|---|---|---|
| | −RNAase | +RNAase | −RNAase | +RNAase |
| normal #1 | 286 | 45 | 416 | 39 |
| normal #2 | 203 | 34 | 387 | 47 |
| Hepatitis #1 | 277 | 67 | 1098 | 386 |
| Hepatitis #2 | 308 | 29 | 1469 | 593 |

Detection of viral DNA sequences in blood of hepatitis patients, using the invention. See text of Example 13 for details. Each number is the average of three determinations, measured by scintillation counting.

Alternatively, a single-stranded DNA probe consisting of the whole hepatitis virus genome was substituted for the RNA probe and the hybridization procedure was carried out as described above. After molecular hybridization the sample was diluted into 1 ml of a solution containing 0.05M tris-HCl, pH 7.0/0.4M NaCl/0.1M ZnCl$_2$/10 U of S1 nuclease and incubated at 45 for 30 min to destroy unhybridized probe as described by the manufacturer, Worthington Biochemicals. Hybridized probe was collected by denaturation and filtration through nitrocellulose (Nygaard and Hall, 1964).

In all of these experimental situations, hybrid formation using blood from the patients with acute active hepatitis and hepatitis virus DNA sequences in mononuclear blood cells was compared with hybrid formation using blood obtained from the virus-negative, normal controls. In every experimental situation, more membrane-bound radioactivity (e.g., molecular hybridization) was obtained with blood from the individuals with hepatitis.

EXAMPLE 14

Use of the Invention for Bacterial DNA Diagnosis on Stool Samples

A stool sample was obtained from a child with diarrhea. To an aliquot was added the bacterium, Campylobacter, at a rate of $10^4$ organisms per milliliter of stool. Stool sample was added to 0.5 gm GuSCN to give 1 ml of solution at 5M GuSCN. The sample was incubated at 105° for 5 minutes. Ten microliters of the stool sample was thoroughly mixed with 2.5 ul of a solution containing 10 ng of a single-stranded, $^{32}$P-labeled RNA probe consisting of a transcript of 10 Kb of the Campylobacter genome. The samples were incubated at 23° for 30 min to allow molecular hybridization and hybrids were detected as described in Example 10. The stool aliquot to which Campylobacter had been added yielded significantly more molecular hybridization than the stool aliquot lacking Campylobacter.

EXAMPLE 15

Use of the invention for detecting HIV Viral RNA in small numbers of cells

Uninfected and HIV infected cells were dissolved in 5M GuSCN/0.1M EDTA at a rate of $10^7$ cells/ml. HIV infected cells were serially diluted into 5M GuSCN/0.1M EDTA or into the uninfected cells dissolved in 5M GuSCN/0.1M EDTA. To 10 ul aliquots, 2.5 ul containing 100 pg of the gag-pol RNA probe described in Example 10 was added. Hybridization was conducted at 25° for 48 hours.

After hybridization, 200 ul 2×SSC/0.1M EDTA/10 ug Poly(A)/4 ug RNAase A/4U RNAase T1 were added and unhybridized probe was digested during a 30 minute incubation at 25°. The solution was chilled, made 10% in TCA and hybridized probe was collected on a nitrocellulose membrane using procedures which are standard in the art. Radioactivity was determined by scintillation counting.

It can be seen from FIG. 12 that the quantity of probe hybridized was a linear function of the number of infected cells from 100 to 10,000 cells, whether they were diluted into 5M GuSCN or into infected cells dissolved in 5M GuSCN. As few as 10 cells gave positive hybridization values.

EXAMPLE 16

Use of the invention to quantify HIV viral RNA in cells

HIV-infected cells were dissolved in 5M GuSCN/0.1M EDTA at a rate of $10^7$ cells/ml. To ten microliters of cells was added 5 ul of a solution containing various amounts of the gag-pol RNA probe described in Example 10. Hybridization was conducted at 25° for 17 hours. Hybrids were processed as described in Example 15.

It can be seen from FIG. 13 that hybridization using infected cells increased rapidly with increasing probe then "plateaued," thereafter increasing at essentially the same rate as when using uninfected cells. The maximum amount of hybridization, less the plateau is the "saturation" value, i.e., the value of amount of probe hybridized when all target RNA sites are occupied. Since at probe excess, the efficiency of saturating target sites in 3M GuSCN in 100% (FIG. 9B of Example 10), the ug of probe hybridized equals the ug of target RNA present in the sample. Therefore, the results of FIG. 12 show 200 and 150 pg of target RNA per $10^5$ cells of culture C and D, respectively. Since the probe has a complexity of 1.5 nucleotides, there are 3,250 and 3,000 molecules of viral RNA per cell in culture C and D, respectively.

This example illustrates the power of the invention for quantifying the number of target RNA molecules in a clinical sample.

EXAMPLE 17

Measurement of HIV Nucleic Acids in Patients

The present invention was performed on a series of 10 patients with ARC and AIDS who were treated with Ampligen. This mismatched dsRNA molecule is both an antiviral and an immune enhancer and, in particular, a potent inhibitor of HIV infection in vitro. Before therapy, all 10 patients in this study demonstrated circulating antibodies against HIV which reacted with the major viral proteins including p24. Additionally, the 10 patients were HIV-positive by the coculture assay on two or three occasions preceding Ampligen treatment.

The number of RNA molecules per 250,000 cells was measured by molecular hybridization with a $^{32}$P RNA probe complementary to the 5' end of the gag gene and most of the pol gene of HIV (see Example 10). Mononuclear cells purified from heparinized blood by Ficoll gradient centrifugation were then harvested by centrifugation and dissolved in 5M GuSCN/0.1M EDTA/10 mM DTT at a concentration of $10^7$ cell/ml (see Example 10). Under these conditions, lymphocytes essentially dissolve and target RNA is liberated in a form directly suitable for efficient molecular hybridization. RNA probe was added directly to GuSCN-dissolved cells and molecular hybridization was conducted at 26° C. for 44 hours in 4M GuSCN. RNA-RNA hybrids were purified by the RNAase/TCA method described in Example 15.

FIGS. 14A–D, 15A–C and 16A–C are graphical illustrations depicting changes caused by chemotherapy in AIDS virus RNA present in blood cells of ten patients with AIDS or ARC (AIDS-related complex), using the present invention. Results are contrasted with coculture and direct serum antigen measurements.

Hybridizations were performed with 25 pg of probe and 250,000 cells in 4M GuSCN at 26° C. Hybridization values were converted to number of target RNA molecules after subtracting negative controls. Negative controls equaled 0.1–0.2% of input probe. One cpm=1500–3600 HIV RNA molecules, depending on the specific activity of the probe.

Prior to Ampligen therapy, HIV RNA could be detected in blood cells of nine of the ten patients by direct molecular hybridization (filled symbols on ordinate, FIGS. 14A–D, 15A–C and 16A–C). The tenth patient (Fari, FIG. 14D) appeared to be hybridization-negative after subtraction of an unusually high negative control value and may have been a false negative for this reason. HIV RNA values were generally around 100,000 molecules per 250,000 mononuclear blood cells, corresponding to about one infected cell in $10^4$ blood mononuclear cells. Since hybridizations were conducted with low amounts of probe, these are minimum HIV RNA values. Serum HIV antigen was detected in only 5 of the 10 patients prior to treatment (Gibm, Bror, Edwd, Tawi, Fowi) (half-filled symbols of FIGS. 14A–D, 15A–C and 16A–C).

HIV RNA in circulating blood cells measured by molecular hybridization became undetectable in all patients at the first time point taken after beginning Ampligen therapy. Two apparently positive hybridization results at eight weeks were associated with unusually low negative controls and proved to be negative on retesting. The present example shows that HIV RNA in circulating blood cells may be directly quantitated in the presence of a chaotropic solution by use of direct molecular hybridization.

EXAMPLE 18

Measurement of rRNA in bacteria

The present invention can be used to measure bacterial rRNA in a specimen without purifying rRNA. This example illustrates the measurement of a non-mRNA species.

E. coli is cultured in L broth, collected by centrifugation and mixed with 5M GuSCN/0.1M EDTA/10 mM dithiothreitol (GED) at a rate of $10^6$ cells/ml. Ten microliters of aliquots of these cells or dilutions in GED are mixed with 2.5 ul of a solution containing $2 \times 10^5$ cpm (2 ng) of a $^{32}$P labeled RNA probe complementary to E. coli rRNA. The mixtures are incubated at 26° C. for 5 hours, then are processed by the RNAase/TCA assay described in Example 15. With this procedure a hybridization signal will increase with increasing numbers of E. coli, being in the range of 10 cpm per bacterium, resulting in a hybridization signal of 100,000 cpm with the undiluted sample.

In contrast, essentially no hybridization (200–500 cpm) will occur with probes which are not complementary with E. coli RNA.

It will be obvious to those skilled in the art that, provided a suitable probe is available, the present invention can be used to detect and quantitate any species of RNA, not only the genomic RNA, mRNA, and rRNA depicted in these examples. It will also be obvious from Examples 1–18 that within rather wide limits changes such as the kind of chaotrope, concentration of chaotrope, temperature and time of hybridization and other steps, quantity of probe, quantity of specimen, nature and quantity of ribonucleases, type of membrane (NC, mixed ester, nylon), method of hybrid purification, etc., can be made without markedly affecting the utility of the invention.

What is claimed is:

1. A method for detecting the presence of or quantitating an amount of RNA containing a specific nucleotide sequence of differing nucleotides in a biological sample comprising cells containing said RNA, comprising the steps of:
   (a) solubilizing the cells of the sample and said RNA contained therein by contacting said biological sample with a chaotropic salt selected from the group consisting of guanidine thiocyanate, alkali metal perchlorates, alkali metal iodides, alkali metal trifluoroacetates, alkali metal trichloroacetates, and alkali metal thiocyanates, whereby a solution of solubilized cells and RNA is produced;
   (b) incubating the solution of the solubilized cells and RNA produced in (a) at a temperature in the range of 20° C. to 40° C. with at least one nucleic acid probe in solution, said at least one nucleic acid probe being complementary and sequence specific to said specific nucleotide sequence of differing nucleotides of the solubilized RNA under conditions which cause molecular hybridization between said at least one nucleic acid probe in solution and said solubilized RNA, said molecular hybridization occurring in the absence of formamide; and
   (c) detecting said molecular hybridization occurring in (b).

2. The method of claim 1 wherein said chaotropic salt is guanidine thiocyanate.

3. The method of claim 1, wherein said at least one nucleic acid probe hybridizes to at least a fragment of HIV viral RNA.

4. A method according to claim 1 wherein the RNA detected or quantitated is ribosomal RNA.

5. A method according to claim 1 wherein the RNA detected or quantitated is genomic RNA.

6. A method for detecting the presence of or quantitating the amount of DNA in a biological sample comprising cells, comprising the steps of
   (a) solubilizing the cells of the sample and the DNA contained therein by contacting said biological sample with a chaotropic salt selected from the group consisting of guanidine thiocyanate, alkali metal perchlorates, alkali metal iodides, alkali metal trifluoroacetates, alkali metal trichloroacetates, and alkali metal thiocyanates, whereby a solution of solubilized cells and DNA is produced;
   (b) heating the solution of the solubilized cells and DNA produced in (a) to a temperature of at least 45° C. and maintaining the temperature for a period of time sufficient to denature the DNA thereby producing a solution of solubilized cells and single-stranded DNA;
   (c) incubating the solution of the solubilized cells and single-stranded DNA produced in (b) at a temperature in the range of 20° C. to 40° C. with at least one nucleic acid probe in solution, said at least one nucleic acid probe being complementary to at least a portion of said solubilized single-stranded DNA under conditions which cause molecular hybridization between said at least one nucleic acid probe in solution and said solubilized single-stranded DNA, said molecular hybridization occurring in the absence of formamide; and
   (d) detecting said molecular hybridization occurring in (c).

7. The method of claim 6 wherein said chaotropic salt is guanidine thiocyanate.

8. A method for detecting the presence of or quantitating an amount of RNA containing a specific nucleotide sequence of differing nucleotides in a biological sample comprising cells containing said RNA, comprising the steps of:
   (a) solubilizing the cells of the sample and said RNA contained therein by contacting said biological sample with a chaotropic salt selected from the group consisting of guanidine thiocyanate, alkali metal perchlorates, alkali metal iodides, alkali metal trifluoroacetates, alkali metal trichloroacetates, and alkali metal thiocyanates, whereby a solution of solubilized cells and RNA is produced;
   (b) incubating the solution of the solubilized cells and RNA produced in (a) at a temperature in the range of 20° C. to 40° C. with at least one immobilized nucleic acid probe, said at least one nucleic acid probe being complementary and sequence specific to said specific nucleotide sequence of differing nucleotides of the solubilized RNA under conditions which cause molecular hybridization between said at least one immobilized nucleic acid probe and said solubilized RNA, said molecular hybridization occurring in the absence of formamide; and
   (c) detecting said molecular hybridization occurring in (b).

9. The method of claim 8 wherein said nucleic acid probe is immobilized by:
   a) first contacting said probe with an immobilizing material; and
   b) then blocking the remaining active sites on said immobilizing material.

10. The method of claim 8 wherein said at least one nucleic acid probe hybridizes to at least a fragment of HIV viral RNA.

11. The method of claim 8 wherein said chaotropic salt is guanidine thiocyanate.

12. A method according to claim 8 wherein the RNA detected or quantitated is ribosomal RNA.

13. A method according to claim 8 wherein the RNA detected or quantitated is genomic RNA.

14. A method for detecting the presence of or quantitating the amount of DNA in a biological sample comprising cells, comprising the steps of:
   (a) solubilizing the cells of the sample and the DNA contained therein by contacting said biological sample with a chaotropic salt selected from the group consisting of guanidine thiocyanate, alkali metal perchlorates, alkali metal iodides, alkali metal trifluoroacetates, alkali metal trichloroacetates, and alkali metal thiocyanates, whereby a solution of solubilized cells and DNA is produced;
   (b) heating the solution of the solubilized cells and DNA produced in (a) to a temperature of at least 45° C. and maintaining the temperature for a period of time sufficient to denature the DNA thereby producing a solution of cells and solubilized single-stranded DNA;
   (c) incubating the solution of the solubilized cells and single-stranded DNA produced in (b) at a temperature in the range of 20° C. to 40° C. with at least one immobilized nucleic acid probe, said at least one nucleic acid probe being complementary to at least a portion of said solubilized single-stranded DNA under conditions which cause molecular hybridization between said at least one immobilized nucleic acid probe and said solubilized single-stranded DNA, said molecular hybridization occurring in the absence of formamide; and (d) detecting said molecular hybridization occurring in (c).

15. The method of claim 14 wherein said nucleic acid probe is immobilized by:
 a) first contacting said probe with an immobilizing material; and
 b) then blocking the remaining active sites on said immobilizing material.

16. The method of claim 14, wherein said chaotropic salt is guanidine thiocyanate.

* * * * *